United States Patent
Babb et al.

(10) Patent No.: US 10,787,522 B2
(45) Date of Patent: Sep. 29, 2020

(54) $V_L$ ANTIGEN BINDING PROTEINS EXHIBITING DISTINCT BINDING CHARACTERISTICS

(71) Applicant: Regeneron Pharmaceuticals, Inc., Tarrytown, NY (US)

(72) Inventors: Robert Babb, River Edge, NJ (US); Ashique Rafique, Yonkers, NY (US); Tammy T. Huang, Cross River, NY (US); Ergang Shi, Ossining, NY (US); Lynn Macdonald, Harrison, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 3 days.

(21) Appl. No.: 15/925,501

(22) Filed: Mar. 19, 2018

(65) Prior Publication Data

US 2018/0273641 A1  Sep. 27, 2018

Related U.S. Application Data

(62) Division of application No. 14/664,750, filed on Mar. 20, 2015, now abandoned.

(60) Provisional application No. 61/968,896, filed on Mar. 21, 2014, provisional application No. 62/079,078, filed on Nov. 13, 2014, provisional application No. 62/088,117, filed on Dec. 5, 2014.

(51) Int. Cl.
| | |
|---|---|
| *C07K 16/26* | (2006.01) |
| *C07K 16/44* | (2006.01) |
| *C07K 16/00* | (2006.01) |
| *A01K 67/027* | (2006.01) |
| *C12N 15/85* | (2006.01) |
| *G01N 33/68* | (2006.01) |

(52) U.S. Cl.
CPC .......... *C07K 16/44* (2013.01); *A01K 67/0275* (2013.01); *A01K 67/0278* (2013.01); *C07K 16/00* (2013.01); *C12N 15/8509* (2013.01); *G01N 33/6854* (2013.01); *A01K 2217/072* (2013.01); *A01K 2227/105* (2013.01); *A01K 2267/01* (2013.01); *C07K 2317/20* (2013.01); *C07K 2317/21* (2013.01); *C07K 2317/515* (2013.01); *C07K 2317/569* (2013.01); *C07K 2317/62* (2013.01); *C07K 2317/92* (2013.01)

(58) Field of Classification Search
CPC .... C07K 16/26; C07K 16/461; C07K 16/462; C07K 2317/21; C07K 2317/15; C07K 2317/92; C07K 16/00; C07K 2317/569; C07K 2317/515; C07K 2317/20; C12N 15/8509; C12N 2800/30; C12N 2800/204; A01K 67/0278; A01K 67/0275; A01K 2227/105; A01K 2217/072; A01K 2207/15; A01K 2267/01; G01N 33/6854; A61K 2217/15

See application file for complete search history.

(56) References Cited

U.S. PATENT DOCUMENTS

| | | |
|---|---|---|
| 4,977,081 A | 12/1990 | Raybould et al. |
| 5,545,806 A | 8/1996 | Lonberg et al. |
| 5,545,807 A | 8/1996 | Surani et al. |
| 5,770,429 A | 6/1998 | Lonberg et al. |
| 5,800,988 A | 9/1998 | Casterman et al. |
| 5,840,526 A | 11/1998 | Casterman et al. |
| 5,874,541 A | 2/1999 | Casterman et al. |
| 5,939,598 A | 8/1999 | Kucherlapti et al. |
| 5,942,435 A | 8/1999 | Wheeler |
| 6,005,079 A | 12/1999 | Casterman et al. |
| 6,015,695 A | 1/2000 | Casterman et al. |
| 6,075,181 A | 6/2000 | Kucherlapati et al. |
| 6,150,584 A | 11/2000 | Kucherlapati et al. |
| 6,162,963 A | 12/2000 | Kucherlapati et al. |
| 6,255,458 B1 * | 7/2001 | Lonberg ............. A01K 67/0275 435/326 |
| 6,461,818 B1 | 10/2002 | Bradley et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,657,103 B1 | 12/2003 | Kucherlapati et al. |
| 6,673,986 B1 | 1/2004 | Kucherlapati et al. |
| 6,765,087 B1 | 7/2004 | Casterman et al. |
| 6,774,279 B2 | 8/2004 | Dymecki |
| 6,998,514 B2 | 2/2006 | Bruggemann |
| 7,064,244 B2 | 6/2006 | Jakobovits et al. |
| 7,105,348 B2 | 9/2006 | Murphy et al. |
| 7,183,076 B2 | 2/2007 | Arathoon et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,582,298 B2 | 9/2009 | Stevens et al. |
| 7,910,798 B2 | 3/2011 | Tanamachi et al. |
| 7,919,257 B2 | 4/2011 | Hoogenboom et al. |
| 7,932,431 B2 | 4/2011 | Bruggemann |

(Continued)

FOREIGN PATENT DOCUMENTS

| | | |
|---|---|---|
| CN | 1203922 A | 1/1999 |
| EP | 0583980 A1 | 8/1993 |

(Continued)

OTHER PUBLICATIONS

Rudikoff et al., Proc. Natl. Acad. Sci. USA vol. 79 p. 1979 (Year: 1982).*

(Continued)

*Primary Examiner* — Phuong Huynh
(74) *Attorney, Agent, or Firm* — Rita Wu; Elysa Goldberg; FisherBroyles, LLP

(57) ABSTRACT

Methods for making, identifying, isolating and/or making binding proteins that contain an immunoglobulin light chain variable domain, including a somatically hypermutated light chain variable domain, fused with a heavy chain constant region, are provided. Exemplary binding proteins specific to small molecules are also provided.

20 Claims, 7 Drawing Sheets

(56) References Cited

U.S. PATENT DOCUMENTS

| | | |
|---|---|---|
| 8,158,419 B2 | 4/2012 | Lonberg et al. |
| 8,502,018 B2 | 8/2013 | Murphy et al. |
| 8,568,992 B2 | 10/2013 | Walker et al. |
| 8,586,713 B2 | 11/2013 | Davis et al. |
| 8,629,317 B2 | 1/2014 | Cogne et al. |
| 8,642,835 B2 | 2/2014 | Macdonald et al. |
| 8,697,940 B2 | 4/2014 | Macdonald et al. |
| 9,365,655 B2 | 6/2016 | Craig et al. |
| 9,516,868 B2 | 12/2016 | Macdonald et al. |
| 9,686,970 B2 | 6/2017 | Macdonald et al. |
| 10,251,377 B2 | 4/2019 | Clube |
| 2002/0026036 A1 | 2/2002 | Shitara et al. |
| 2002/0088016 A1 | 7/2002 | Bruggemann |
| 2002/0106628 A1 | 8/2002 | Economides et al. |
| 2002/0106629 A1 | 8/2002 | Murphy et al. |
| 2003/0108925 A1 | 6/2003 | Dix et al. |
| 2003/0109021 A1 | 6/2003 | Wu et al. |
| 2003/0217373 A1 | 11/2003 | Green et al. |
| 2004/0018626 A1 | 1/2004 | Murphy et al. |
| 2004/0101920 A1 | 5/2004 | Radziejewski et al. |
| 2005/0060763 A1 | 3/2005 | Bruggeman et al. |
| 2005/0246782 A1 | 11/2005 | Etches et al. |
| 2006/0015949 A1 | 1/2006 | Lonberg et al. |
| 2006/0015957 A1 | 1/2006 | Lonberg et al. |
| 2006/0015958 A1 | 1/2006 | Kuroiwa et al. |
| 2006/0026696 A1 | 2/2006 | Buelow et al. |
| 2006/0083747 A1 | 4/2006 | Winter |
| 2006/0106203 A1 | 5/2006 | Winter |
| 2006/0199204 A1 | 9/2006 | Dix et al. |
| 2006/0257406 A1 | 11/2006 | Winter |
| 2006/0280734 A1 | 12/2006 | Winter |
| 2007/0209083 A1 | 9/2007 | Thiam et al. |
| 2007/0275466 A1 | 11/2007 | Economides et al. |
| 2007/0280945 A1 | 12/2007 | Stevens et al. |
| 2008/0267982 A1 | 10/2008 | Kiselev et al. |
| 2009/0258392 A1 | 10/2009 | Gallo et al. |
| 2009/0271880 A1 | 10/2009 | Grosveld et al. |
| 2010/0069614 A1 | 3/2010 | Houtzager et al. |
| 2010/0122358 A1 | 5/2010 | Bruggemann |
| 2010/0146647 A1 | 6/2010 | Logtenberg et al. |
| 2010/0196367 A1 | 8/2010 | Day |
| 2010/0254988 A1 | 10/2010 | Bossenmaier et al. |
| 2010/0254989 A1 | 10/2010 | Bossenmaier et al. |
| 2010/0298542 A1 | 11/2010 | Igawa et al. |
| 2010/0331527 A1 | 12/2010 | Davis et al. |
| 2011/0123527 A1 | 5/2011 | Shizuya et al. |
| 2011/0138489 A1 | 6/2011 | Tanamachi et al. |
| 2011/0145937 A1 | 6/2011 | Macdonald et al. |
| 2011/0195454 A1 | 8/2011 | McWhirter et al. |
| 2011/0236378 A1 | 9/2011 | Green et al. |
| 2011/0283376 A1 | 11/2011 | Murphy et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0272344 A1 | 10/2012 | Tanamachi et al. |
| 2012/0322108 A1 | 12/2012 | Macdonald et al. |
| 2013/0045492 A1 | 2/2013 | Babb et al. |
| 2013/0096287 A1 | 4/2013 | Macdonald et al. |
| 2013/0145484 A1 | 6/2013 | Logtenberg et al. |
| 2013/0185821 A1 | 7/2013 | Babb et al. |
| 2013/0198879 A1 | 8/2013 | McWhirter et al. |
| 2013/0212719 A1 | 8/2013 | Macdonald et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0263293 A1 | 10/2013 | Bradley et al. |
| 2013/0302836 A1 | 11/2013 | McWhirter et al. |
| 2013/0318643 A1 | 11/2013 | Bradley et al. |
| 2013/0323235 A1 | 12/2013 | Craig et al. |
| 2014/0213773 A1 | 7/2014 | Macdonald et al. |
| 2014/0243504 A1 | 8/2014 | Davis et al. |
| 2014/0283150 A1 | 9/2014 | Bradley et al. |
| 2014/0310828 A1 | 10/2014 | Lee et al. |
| 2015/0133641 A1 | 5/2015 | Germaschewski et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2015/0266976 A1 | 9/2015 | Babb et al. |
| 2015/0289489 A1 | 10/2015 | Macdonald et al. |
| 2017/0094955 A1 | 4/2017 | Macdonald et al. |
| 2017/0223939 A1 | 8/2017 | Macdonald et al. |
| 2017/0226231 A1 | 8/2017 | Macdonald et al. |
| 2018/0244804 A1 | 8/2018 | Macdonald et al. |

FOREIGN PATENT DOCUMENTS

| | | |
|---|---|---|
| EP | 0491057 B1 | 12/1998 |
| EP | 2050764 A1 | 4/2009 |
| EP | 1589107 B1 | 12/2009 |
| KR | 1020050042792 A | 5/2005 |
| WO | 1990/004036 A1 | 4/1990 |
| WO | 1991/000906 A1 | 1/1991 |
| WO | 1994/012215 A1 | 9/1994 |
| WO | 1994/025585 A1 | 11/1994 |
| WO | 1996/034103 A1 | 10/1996 |
| WO | 1997/016537 A1 | 5/1997 |
| WO | 1998/024893 A2 | 6/1998 |
| WO | 2000/026373 A1 | 5/2000 |
| WO | 2000/073323 A2 | 12/2000 |
| WO | 2001/053353 A2 | 7/2001 |
| WO | 2002/012437 A2 | 2/2002 |
| WO | 2002/046237 A2 | 6/2002 |
| WO | 2002/066630 A1 | 8/2002 |
| WO | 2002/085944 A2 | 10/2002 |
| WO | 2002/085945 A2 | 10/2002 |
| WO | 2003/002609 A2 | 1/2003 |
| WO | 2003/047336 A1 | 6/2003 |
| WO | 2004/049794 A2 | 6/2004 |
| WO | 2004/058820 A2 | 7/2004 |
| WO | 2004/058822 A2 | 7/2004 |
| WO | 2005/007696 A2 | 1/2005 |
| WO | 2005/019463 A1 | 3/2005 |
| WO | 2005/028510 A2 | 3/2005 |
| WO | 2005/038001 A2 | 4/2005 |
| WO | 2006/008548 A2 | 1/2006 |
| WO | 2006/047367 A2 | 5/2006 |
| WO | 2007/096779 A2 | 8/2007 |
| WO | 2007/117410 A2 | 10/2007 |
| WO | 2008/027986 A2 | 3/2008 |
| WO | 2008/054606 A2 | 5/2008 |
| WO | 2008/076379 A2 | 6/2008 |
| WO | 2008/151081 A1 | 12/2008 |
| WO | 2009/013620 A2 | 1/2009 |
| WO | 2009/018386 A1 | 2/2009 |
| WO | 2009/026660 A1 | 3/2009 |
| WO | 2009/097006 A2 | 8/2009 |
| WO | 2009/143472 A2 | 11/2009 |
| WO | 2009/157771 A2 | 12/2009 |
| WO | 2010/039900 A2 | 4/2010 |
| WO | 2011/004192 A1 | 1/2011 |
| WO | 2011/072204 A1 | 6/2011 |
| WO | 2011/158009 A1 | 12/2011 |
| WO | 2011/163311 A1 | 12/2011 |
| WO | 2011/163314 A1 | 12/2011 |
| WO | 2012/018764 A1 | 2/2012 |
| WO | 2012/063048 A1 | 5/2012 |
| WO | 2012/116926 A1 | 9/2012 |
| WO | 2012/116927 A1 | 9/2012 |
| WO | 2012/141798 A1 | 10/2012 |
| WO | 2013/022782 A1 | 2/2013 |
| WO | 2013/041844 A2 | 3/2013 |
| WO | 2013/041845 A2 | 3/2013 |
| WO | 2013/041846 A2 | 3/2013 |
| WO | 2013/045916 A1 | 4/2013 |
| WO | 2013/061078 A1 | 5/2013 |
| WO | 2013/061098 A2 | 5/2013 |
| WO | 2013/079953 A1 | 6/2013 |

(56) References Cited

FOREIGN PATENT DOCUMENTS

| WO | 2013/096142 A1 | 6/2013 |
|---|---|---|
| WO | 2013/116609 A1 | 8/2013 |
| WO | 2015/143406 A2 | 9/2015 |
| WO | 2015/143414 A2 | 9/2015 |
| WO | 2013/149678 A1 | 9/2016 |

OTHER PUBLICATIONS

Almagro and Fransson (2008) "Humanization of antibodies," Frontiers in Bioscience, 13:1619-1633.
Bispecific monoclonal antibody, From Wikipedia, the free encyclopedia, pp. 1-5; downloaded on Mar. 19, 2019, https://en.wikipedia.org/wiki/Bispecific monoclonal antibody.
Cao, et al. (2009) Isolation and Culture of Primary Bovine Embryonic Stem Cell Colonies by a Novel Method, Journal of Experimental Zoology, 311A:368-376.
Giraldo and Montoliu (2001) "Size matters: use of YACs, BACs and PACs in transgenic animals," Transgenic Research, 18:83-103.
Goldman et al. (2004) "Transgenic animals in medicine: Integration and expression of foreign genes, theoretical and applied aspects," Med. Sci. Monit., 10(11):RA274-285.
Houdebine et al. "Methods to Generate Transgenic Animals," Genetic Engineering in Livestock, New Applications and Interdisciplinary Perspectives, Engelhard M, et al., 2009, XVI, 146, pp. 31-47.
Jensen, et al. (2007) One Step Generation of Fully Chimeric Antibodies Using Cγ1- and Cκ Mutant Mice, J. Immunother., 30(3):338-349.
Roussel et al. (1999) "The structure of an entire noncovalent immunoglobulin kappa light-chain dimer (Bence-Jones protein) reveals a weak and unusual constant domains association," Eur. J. Biochem., 260:192-199.
Tian et al. (2016) "Induction of HIV Neutralizing Antibody Lineages in Mice with Diverse Precursor Repertoires," Cell, 166:1471-1484.
Vettermann and Schlissel (2010) "Allelic eclusion of immunoglobulin genes: models and mechanisms," Immunological Reviews, 237:22-42.
Yarilin A.A. "Osnovy immunologii", M.: Meditsina, 1999, p. 172-174 (with English translation).
Statement of Relatedness under MPEP 2001.06 with Respect to U.S. Appl. No. 15/925,501, dated Sep. 12, 2019.
Adams et al. (2005) "A genome-wide, end-sequenced 129Sv BAC library resource for targeting vector construction," Genomics, 86(6):753-758.
Adderson et al. (1991) "Restricted Ig H Chain V Gene Usage in the Human Antibody Response to Haemophilus influenzae Type b Capsular Polysaccharide," The Journal of Immunology, 147:1667-1674.
Adderson et al. (1993) "Restricted Immunoglobulin VH Usage and VDJ Combinations in the Human Response to Haemophilus influenzae Type b Capsular Polysaccharide," J. Clin. Invest., 91:2734-2743.
Almagro et al. (2004) "Identification of differences in the specificity-determining residues of antibodies that recognize antigens of different size: implications for the rational design of antibody repertoires," Journal of Molecular Recognition, 17(2):132-143.
Altschul et al. (1990) "Basic local alignment search tool," J. Mol. Biol., 215(3): 403-410.
Altschul et al. Methods in Enzymology.
Altschul et al. (1997) "Gapped BLAST and PSI-BLAST: a new generation of protein database search programs," Nucleic Acids Res. 25:3389-3402.
Amit and Itskovitz-Eldor (2009) "Embryonic Stem Cells: Isolation, Characterization and Culture," Adv. Biochem. Eng. Biotechnol, 114:173-184.
Andris-Widhopf et al. (2000) "Methods for the generation of chicken monoclonal antibody fragments by phage display," J. Immunol. Methods 242:159-181.

Astellas Negotiates $295M License Extension to Regeneron's VelocImmune mAb Platform, Genetic Engineering & Biotechnology News, Jul. 28, 2010, 2 pages.
Auerbach et al. (2000) "Establishment and Chimera Analysis of 129/SvEv- and C57BL/6-Derived Mouse Embryonic Stem Cell Lines," BioTechniques, 29(5):1024-1028, 1030, 1032.
Austin et al. (2004) "The Knockout Mouse Project," Nature Genetics, 36(9):921-924.
Author Not Known (2007) "Breeding Strategies for Maintaining Colonies of Laboratory Mice," A Jackson Laboratory Resource Manual, pp. 1-29.
Azzazy and Highsmith (2002) "Phage display technology: clinical applications and recent innovations," Clin. Biochem. 35:425-445.
Baird and Myszka (2001) "Current and emerging commercial optical biosensors," J. Molecular Recognition, 14:261-268.
Bando et al. (2004) "Characterization of VH gene expressed in PBL from children with atopic diseases: detection of homologous VH1-69 derived transcripts from three unrelated patients," Immunology Letters, 94:99-106.
Bankovich et al. (2007) "Structural Insight into Pre-B Cell Receptor Function," Science, 316(5822):291-294.
Baseggio et al. (2010) "CD5 expression identifies a subset of splenic marginal zone lymphomas with higher lymphocytosis: a clinico-pathological, cytogenetic and molecular study of 24 cases," Haematologica, 95(4):604-612.
Bates et al. (2007) "Chromosomal position of a VH gene segment determines its activation and inactivation as a substrate for V(D)J recombination," Journal of Experimental Medicine, 204(13):3247-3256.
Berberian et al. (1991) "A VH Clonal Deficit in Human Immunodeficiency VirUS Positive Individuals Reflects a B-Cell Maturational Arrest," Blood, 78(1):175-179.
Blankenstein et al. (1987) "Immunoglobulin $V_H$ region genes of the mouse are oranized in overlapping clusters," Eur. J. Immunol., 17:1351-1357.
Brevini et al. (2010) "No shortcuts to pig embryonic stem cells," Theriogenology 74(4):544-550.
Brezinschek et al. (1995) "Analysis of the Heavy Chain Repertoire of Human Peripheral B Cells Using Single-Cell Polymerase Chain Reaction," Journal of Immunology, 155:190-202.
Brodeur et al. (1984) "The immunoglobulin heavy chain variable region (Igh-V) locus in the mouse I. One hundred IgH-V genes comprise seven families of homologous genes," Eur. J. Immunol., 14:922-930.
Brouwers et al. (2015) "Unexpected Phenotypes in Mouse Models Carrying the Human Growth Hormone Minigene to Enhance Transgene Expression," Journal of Steroids & Hormonal Science, 6(2):1-2.
Bruchez et al. (1998) "Semiconductor Nanocrystals as Fluorescent Biological Labels," Science 281: 2013-2016.
Brüggemann et al. (1989) "A repertoire of monoclonal antibodies with human heavy chains from transgenic mice," Proceedings of the National of Academy of Science USA, 86:6709-6713.
Brüggemann and Neuberger (1996) "Strategies for expressing human antibody repertoires in transgenic mice," Review Immunology Today, 192(17):391-397.
Brüggemann (2001) "Human Antibody Expression in Transgenic Mice," Archivum Immunologiae et Therapiae Experimentalis, 49:203-208.
Brüggemann (2004) "Human Monoclonal Antibodies from Translocus Mice," Molecular Biology of B Cells, Eds. Honjo, T. and Neuberger, M.S., New York, NY: Academic Press, pp. 547-561.
Burton (1995) "Phage display," Immunotechnology 1:87-94.
Butler, (1998) "Immunoglobulin diversity, B-cell and antibody repertoire development in large farm animals," Rev. Sco. Tech. Off. Int. Epiz., 17(1):43-70.
Carbonari et al. (2005) "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174:6532-6539.
Cavelier et al. (1997) "B lineage-restricted rearrangement of a human Ig kappa transgene," Eur J. Immunol. 27(7):1626-1631.

(56) References Cited

OTHER PUBLICATIONS

Chan et al. (2001) "VH1-69 gene is preferentially used by hepatitis C virUS associated B cell lymphomas and by normal B cells responding to the E2 viral antigen," Blood, 97(4):1023-1026.

Chang et al. (1984) "Immunologic memory to phosphocholine. IV. Hybridomas representative of Group I (T15-like) and Group II (non-T15-like) antibodies utilize distinct VH genes," J. Immunol., 132(3):1550-1555.

Chang et al. (1985) "Novel Arrangement of Immunoglobulin Variable Domains X-Ray Crystallographic Analysis of the Lambda-Chain Dimer Bence-Jones Protein LOC," Biochemistry, American Chemical Society, 24(18):4890-4897.

Charles et al. (2011) "A flow cytometry-based strategy to identify and express IgM from VH1-69+ clonal peripheral B cells," Journal of Immunological Methods, 363:210-220.

Cheval et al. (2012) Of Mice and Men: Divergence of Gene Expression Patterns in Kidney, PLoS One, 7(10):e46876 (12 pages).

Cho, Chunghee, (2012) "Testicular and epididymal ADAMs: experssion and function during fertilization," Nature Reviews Urology, 9:550-560.

Choi et al. (2004) "Characterization and comparative genomic analysis of intronless Adams with testicular gene expression," Genomics, 83(4):636-646.

Choi et al. (2011) "Expression of the metabotropic glutamate receptor 5 (mGluR5) induces melanoma in transgenic mice," PNAS, 108(37):15219-15224.

Choi et al. (2013) "Identification and characterizaion of promoter and regulatory regions for mouse Adam2 gene expression," Molecular Biology Reports, 40:787-796.

Clark and Whitelaw, (2003) "A future for transgenic livestock, National Reviews Genetics," 4(10):825-833.

Cocea et al. (1999) "A targeted deletion of a region upstream from the Jkppa cluster impairs kappa chain rearrangement in cis in mice and in the 103/bcl2 cell line," J. Exp. Med., 189(9):1443-1450.

Combriato et al. (2002) "Regulation of Human Igl Light Chain Gene Expression," The Journal of Immunology, 168:1259-1266.

Davidkova et al. (1997) "Selective Usage of VH Genes in Adult Human B Lymphocyte Repertoires," Scand. J. Immunol., 45:62-73.

Deegan (1976) "Bence Jones Proteins: Nature, Metabolism, Detection and Significance," Annals of Clinical and Laboratory Science, 6(1):38-46.

De Genst et al. (2006) Antibody repertoire development in camelids. Dev. Comp. Immunol, 30:187-198.

Dennis (2002) "Welfare issues of genetically modified animals," ILAR Journal, 43(2):100-109.

Edmundson et al. (1993) "Priniciples and Pitfalls in Designing Site-Directed Peptide Ligands," Proteins: Structure, Function, and Genetics, Wiley-Liss, Inc., 16:246-267.

Edwards et al. (2008) "The ADAM metalloproteinases, Molecular Aspects of Medicine," 29(5):258-289.

Enever et al. (2009) "Next generation immunotherapeutics—honing the magic bullet. Current Opinion in Biotechnology," 20:405-411.

Featherstone, K et al. (2010) "The mouse immunoglobulin heavy chain V-D intergenic sequence contains insulators that may regulate ordered V(D)J recombination," J. Biol. Chem., 285(13): 9327-9338.

Female Science Professor https://science-professor.blogspot.com/2009/04/photoshooters.html; posted Apr. 17, 2009; last accessed May 26, 2017.

Festing et al. (1999) "Revised nomenclature for strain 129 mice," Mamm. Genome 10:836.

Gallo et al. (2000) "The human immunoglobulin loci introduced into mice: V (D) and J gene segment usage similar to that of adult humans," Eur. J. Immunol., 30(2):534-540.

Gama Sosa et al. (2010) "Animal transgenesis: an overview," Brain Structure & Function, 214(2-3):91-109.

Gavilondo and Larrick (2002) BioTechniques 29:128-145.

Gavish et al. (1977) "Comparison of the fine specificity of anti-dinitrophenyl-combining site composed of either VL dimer or VL and VH of protein 315," Biochemistry, 16(14):3154-3159.

Gen Bank accession No. NT_114985, p. 1, first referenced Dec. 1, 2005, last updated Feb. 9, 2015.

Giallourakis et al. (2010) "Elements between the IgH variable (V) and diversity (D) clusters influence antisense transcription and lineage-specific V(D)K recombination," PNAS, 107(51):22207-22212.

Goni et al. (1985) "Sequence similarities and cross-idiotypic specificity of L chains among human monoclonal IgMk with anti-gamma-globulin activity," J. Immunol, 135(6):4073-9.

Gonnet et al. (1992) Exhaustive Matching of the Entire Protein Sequence Database, Science 256:1443-45.

Gorman et al. (1996) "The Ig(kappa) enhancer influences the ratio of Ig(kappa) versus Ig(lambda) B lymphocytes," Immunity, 5(3):241-252.

Grawunder et al. (1995) "Induction of sterile transcription from the kappa L chain gene locus in V(D)J recombinase-deficient progenitor B cells," International Immunology, 7(12):1915-1925.

Green, L.et al. (1994) "Antigen-specific human monoclonal antibodies from mice engineered with human Ig heavy and light chain YACs," Nature Genetics, 7(1):13-21.

Gunther et al. (2007) "SuperHapten: a comprehensive database for small immunogenic compounds," Nucleic Acid Research, 35:D906-D910.

Haines and Brodeur (1998) Accessibility changes across the mouse lgh-V locus during B cell development, Eur. J. Immunol., 28:4228-4235.

Han et al. (2009) "Comprehensive analysis of reproductive ADAMs: relationship of ADAM4 and ADAM6; with an ADAM complex required for fertilization in mice," Biology of Reproduction, 80(5):1001-1008.

Harding and Lonberg (1995) "Class switching in human immunoglobulin transgenic Mice," Ann. N Y Acad. Sci., 764:536-546.

Helms and Wetzel (1995) "Destabilizing loop swaps in the CDRs of an immunoglobulin $V_L$ domain," Protein Science, 4:2073-2081.

Hendricks et al. (2010) "Organization of the variable region of the immunoglobulin heavy-chain gene locus of the rat," Immunogenetics, 62(7):479-486.

Hirabayashi et al. (1995) "Kinetic analysis of the interactions of recombinant human VpreB and Ig V domains," J. Immunol., 155:1218-1228.

Hoiruchi and Blobel (2005) Studies from Adam Knockout Mice, in Hooper and Lendeckel, The ADAM Family of proteases, Netherlands 2005, Springer (37 pages).

Hoogenboom (1997) "Designing and optimizing library selection strategies for generating high-affinity antibodies," TIB Tech. 15:62-70.

Hoogenboom and Chames (2000) "Antibodies isolated from an animal (e.g., a mouse) that is transgenic for human immunoglobulin genes," Immunology Today 21:371-378.

House mouse (Mus musculus) IGH locus on chromosome 12 (12F2) strain C57BL/6 pp. 1-5; dowloaded Aug. 26, 2016.

Huang et al. (1993) "A Majority of Ig H Chain cDNA of Normal Human Adult Blood Lymphocytes Resembles cDNA for Fegal Ig and Natural Autoantibodies," The Journal of Immunology, 151(10):5290-5300.

Huang et al. (1994) "Comparison of Crystal Structures of Two Homologous Proteins: Structural Origin of Altered Domain Interactions in Immunoglobulin Light-Chain Dimers," Biochemistry, 33:14848-14857.

Hussack et al. (2012) "A VL single-domain antibody library shows a high-propensity to yield non-aggregating binders," Protein Engineering, Design & Selection, 25(6):313-318.

Ill et al. (1997) "Design and construction of a hybrid immunoglobulin domain with properties of both heavy and light chain variable regions," Protein Engineering, 10(8):949-957.

Janssens et al. (2006) "Generation of heavy-chain-only antibodies in mice," Proc. Nat'l. Acad. Sci., 103(41):15130-15135.

Johnson et al. (1997) "Ig VH1 Genes Expressed in B Cell Chronic Lymphocytic Leukemia Exhibit Distinctive Molecular Features," The Journal of Immunology, 158:235-246.

Johnston et al. (2006) "Complete Sequence Assembly and Characterization of the C57BL/6 Mouse Ig Heavy Chain V Region[1]," J. Immunol., 176:4221-4234.

(56) References Cited

OTHER PUBLICATIONS

Kaartinen et al. (1988) "Combinatorial association of V genes: One VH gene codes for three non-cross-reactive monoclonal antibodies each specific for a different antigen (phOXAZOLONE, NP or GAT)," Mol. Immunol., 25(9):859-865.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kantor et al. (1997) "An Unbiased Analysis of VH-D-JH Sequences from B-1a, B-1b, and Conventional B Cells," The Journal of Immunology, 158: 1175-1186.
Kaushik et al. (2002) "Novel insight into antibody diversification from cattle," Veterinary Immunology and Immunopathology, 87(3-4):347-350.
Kellermann and Green (2002) "Antibody discovery: the use of transgenic mice to generate human monoclonal antibodies for therapeutics," Current Opinion in Biotechnology 13:593-597.
Kim et al. (2006) "Expression and relationship of male reproductive ADAMs in mouse," Biology of Reproduction, 74(4):744-750.
Kingzette et al.(1998) "Trans-chromosomal recombination within the Ig heavy chain switch region in B lymphocytes," PNSA, 95(20):11840-11845.
Klebig, (1995) "Ectopic Expression of the Agouti Gene in Transgenic Mice Causes Obesity," Features fo Type II Diabetes, and Yellow Fur, PNAS 92:4728-4732.
Kobayashi and Oyama (2011) "Antibody engineering toward high-sensitivity high-throughput immunosensing of small molecules," The Royal Society of Chemistry, Analyst, 136:642-651 (DOI: 10.1039/c0an00603c).
Kong et al. (2009) "Transgene expression is associated with copy number and cytomegalovirus promoter methylation in transgenic pigs," PLoS One 4(8):1-10.
Korhonen, J.M, https://jmkorhonen.net/2012/06/25/is-it-ok-to-record-conferencepresentations-reconsidering-fair-use-and-electronic-note-taking; posted Jun. 25, 2012; last accessed May 26, 2017.
Kunert et al. (2004) "Characterization of Molecular Features, Antigen-Binding, and in Vitro Properties of IgG and IgM Variants of 4E10, an Anti-HIV Type 1 Neutralizing Monoclonal Antibody," Aids ReSearch and Human Retroviruses, 20(7):755-762.
Kuroiwa et al. (2002) "Cloned transchromosomic calves producing human immunoglobulin," Nat. Biotechnol., 20(9):889-894.
Kuroiwa et al. (2004) "Sequential targeting of the genes encoding immunoglobulin-µ and prion protein in cattle," Nature Genetics, 36:775-780.
Lavial and Pain, (2010) "Chicken embryonic stem cells as a non-mammalian embryonic stem cell model" Develop. Groth Diff., 52(1):101-114.
Leclercq et al. (1989) "A novel germ-like JK transcript starting immediately upstream of JK1," Nucleic Acids Research, 17(17):6809-6819.
Lee et al. (2014) "Complete humanization of the mouse immunoglobulin loci enables efficient therapeutic antibody discovery," Nature Biotechnology, 32(4):356.
Lefranc, (2001) "Nomeclature of the human immunoglobulin lambda (IGL) genes," Experimental and Clinical Immunogenetics, S. Karger Basel C.H., 18(4):242-254.
Lefranc, (2000) "Nomoclature of the Human Immunoglobulin Genes Current Protocols in Immunology," Supplement 40:1.1P.1-A.1P.37.
Lefranc, (2004) Molecular Biology of B Cells. London: Elsevier Academic Press, Ed. Honjo, Chapter 4 pp. 37-59.
Leitzgen et al. (1997) "Assembly of Immunoglobulin Light Chains as a Prerequisite for Secretion," Journal Biological Chemistry., 272(5):3117-3123.
Lin et al. (1990) "Research of Immune Globulin in Mice," Guangzhou Medical Journal, 1:49-50 and English translation.
Little et al. (2000) "Of mice and men: hybridoma and recombinant antibodies.," Immunology Today 21:364-370.
Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).
Lonberg, (2005) "Human antibodies from transgenic animals, Nature Biotechnology," 23(9):1117-1125.
Lovell-Badge (2007) "Many ways to pluripotency," Nature Biotechnology, 25:1114-1116.
MacDonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 2 pages original (pp. 3-11 are p. 2 of the original, enlarged).
MacDonald et al. (2014) "Precise and in situ genetic humanization of 6 Mb of mouse immunoglobulin genes," PNAS, 111(14):5147-5152.
Mageed et al. (2001) "Rearrangement of the human heavy chain variable region gene V3-23 in transgenic mice generates antibodies reactive with a range of antigens on the basis of VhCDR3 and residues intrinsic to the heavy chain variable region," Clin Exp Immunol, 123:1-8.
Mahmoud et al. (2011) "Limiting CDR-H3 Diversity Abrogates the Antibody Response to the Bacterial Polysaccharide α 1→3 Dextran," The Journal of Immunology, 187: 879-886.
Mahmoudi et al. "V region gene analysis of human IgM hybridoma monoclonal anti-Sm antibodies," Lupus, 6:578-589, 1997.
Manis et al. (2002) "Mechanism and control of class-switch recombination," TRENDS in Immunology, 23(1):31-39.
Marasca et al. (2001) "Immunoglobulin Gene Mutations and Frequent Use of VH1-69 and VH4-34 Segments in Hepatitis C VirUS Positive and Hepatitis C VirUS Negative Nodal Marginal Zone B-Cell Lymphoma," American Journal of Pathology, 159(1): 253-261.
Martin and Van Ness, (1989) "Identification of a Germ Line Transcript from the Unrearranged Kappa Gene in Human B Cells," Molecular and Cellular Biology, 9(10):4560-4562.
Martin and Van Ness, (1990) "Initiation and Processing ofTwo Kappa Immunoglobulin Germ Line Transcripts in Mouse B cells," Molecular and Cellular Biology, 10(5):1950-1958.
McGoldrick et al. (2013) "Rodent models of amyotrophic lateral sclerosis," Biochimica et Biophysica Acta, 1832:1421-1436.
Mei et al. (1991) "Vasoactive intestinal peptide hydrolysis by antibody light chains," J. Biol. Chem., 266(24):15571-4.
Melton (2002) Chapter 8: Gene-Targeting Strategies, Methods in Molecular Biology, Transgenesis Techniques, 2nd Edition, Principles and Protocols, 180:19 pages.
Miklos et al. (2000) "Salivary gland mucosa-associated lymphoid tissue lymphoma immunoglobulin VH genes show frequent use of V1-69 with distinctive CDR3 features," Blood, 95:3878-3884.
Miller et al. (2003) "Design, Constructio, and In Vitro Analyses of Multivalent Antibodies," J. Immunol., 170:4854-4861.
Mills et al. (1997) "Enhancer complexes located downstream of both human immunoglobulin Calpha genes, Journal of Experimental Medicine," 186(6):845-858.
Mirzabekov et al. (1996) Nucleic Acids Res 24(15): 2998-3004.
Montaño and Morrison, (2002) "Influence of the Isotype of the Light Chain on the Properties of IgG," Journal of Immunology, 168:224-231.
Moran, (2013) "Mouse platforms jostle for slice of humanized antibody market," Nature Biotechnology, 31(4):267-268.
Morrison et al. (1998) "Variable region domain exchange influences the functional properties of igG," J. Immunol., 160:2802-2808.
Mortari et al. (1993) "Human Cord Blood Antibody Repertoire," The Journal of Immunology, 150(4):1348-1357.
Muñoz et al. (2008) "Conventional pluripotency markers are unspecific for bovine embryonic-derived cell-lines," Theriogenology, 69(9):1159-1164.
Muller et al. (1993) "B-Cell Abnormalities in AIDS: Stable and Clonally-Restricted Antibody Response in HIV-1 Infection," Scand. J. Immunol., 38:327-334.

(56) References Cited

OTHER PUBLICATIONS

Murphy and Silha (2000) "Unexpected and unexplained phenotypes in transgenic models," Growth Hormone & IGF Research, 10:233-235.
Murphy, A., "VelocImmune: Immunoglobulin Variable Region Humanized Mice, Recombinant Antibodies for Immunotherapy," Ed. Little, M., New York, NY: Cambridge University Press, Chapter 8, pp. 100-107 (2009).
Murphy Slide Deck, Slide Presentation dated Nov. 3, 2009, "BAC-based Modifications of the Mouse Genome: The Big and the Backward," slides 1-57.
Murphy (2012) Kenneth, Janeway's Immunobiology 8th Edition. New York: Garland Science, Printed in USA., Chapter 5, Sections 5-1 to 5-4, pp. 157-162.
Myszka (1999) "Improving biosensor analysis," J. Mol. Recogn. 12:279-284.
Nagle, Regeneron helps make Sanofi VelocImmune to its "weak pipeline". <http://www.outsourcing-pharma.com> Published Dec. 3, 2007.
News in Brief Article. Big Pharma views for mice, Nature Biotechnology Jun. 2007;25(6):613.
Nicholson et al. (1999) "Antibody Repertoires of four- and Five-Feature Translocus Mice Carrying Human Immunoglobulin Heavy Chain and kappa and lambda light chain Yeast Artificial Chromosomes," Journal of Immunology, 163(12):6898-6906.
Niemann et al. (2005) "Transgenic farm animals: present and future, Review of Science Technology," 24(1):285-298.
Nishimura et al. (2004) "Possible Function of the ADAM1a/ADAM2 Fertilin Complex in the Appearance of ADAM 3 on the Sperm Surface," The Journal of Biological Chemistry, 279(33):34957-34962.
Nitschke et al. (2001) "Deletion of the DQ52 element with the Ig heavy chain locus leads to a selective reduction in VDJ recombination and altered D gene usage," J. Immunol., 166:2540-52.
Novotny et al. (1985) "Structural Invariants of Antigen Binding: Comparison of Immunoglobulin VL-VH and VL-VL Domain Dimers," Proc. Nat. Acad. Sci., 82:4592-4596.
Oberdoerffer et al. (2003) "Unidirectional Cre-mediated genetic inversion in mice using the mutant loxP pair lox66/Iox71," Nucleic Acids Research, 31(22)(e140):1-7.
Oddo et al. (2003) "Triple-Transgenic Model of Alzheimer's Disease with Plaques and Tangles: Intracellular A and Synaptic Dysfunction," Neuron, 39:409-421.
Paris and Stout, (2010) "Equine embryos and embryonic stem cells: defining reliable markers of pluripotency," Theriogenology, 74(4):516-524.
Parng et al. (1996) "Gene conversion contributes to the Ig light chain diversity in cattle," The Journal of Immunology, 157(12):5478-5486.
Pasqualini and ARAP (2004) "Hybridoma-free generation of monoclonal antibodies," Proceedings of the National Academy of Sciences USA, 101(1):257-259.
Pereira et al. (1998) "Cardiolipin binding a light chain from lupus-prone mice," Biochemistry, 37:1430-7.
Perez et al. (2010) "Primary cutaneous B-cell lymphoma is associated with somatically hypermutated immunoglobulin variable genes and frequent use of VH1-69 and VH4-59 segments," British Journal of Dermatology, 162:611-618.
Petitte et al. (2004) "Avian pluripotent stem cells," Mech. of Develop., 121(9):1159-1168.
Pettersson et al. (1990) "A second B cell-specific enhancer 3' of the immunoglobulin heavy-chain locus," Nature, 344(6262):165-168.
Popov et al. (1999) "A Human Immunoglobulin lambda locus is Similarly Well Expressed in Mice and Humans," J. Exp. Med., 189(10):1611-1619.
Pos et al. (2008) "VH1-69 germline encoded antibodies directed towards ADAMTSI3 in patients with acquired thrombotic thrombocytopenic purpura," Journal of Thrombosis & Haemostasis, 7:421-428.

Poueymirou et al (2007) "F0 generation mice fully derived from gene-targeted embryonic stem cells allowing immediate phenotypic analyses," Nat Biotechnol 25, 91-99.
Qi et al. (2005) "A new transgenic rat model of hepatic steatosis and the metabolic syndrome," Hypertension, 45(5):1004-1011.
Ramírez-Solis et al. (1995) "Chromosome engineering in mice," Nature, 378(6558):720-724.
Ramsden et al. (1994) "Conservation of sequence in recombination signal sequence spacers," Nucleic Acids Res., 22(10):1785-1796.
Ravetch et al. (1981) "Structure of the human immunoglobulin mu locus: characterization of embryonic and rearranged J and D genes," Cell, 27:583-591.
Ray (1991) "Ectopic expression of a c-kitW42 minigene in transgenic mice: recapitulation of W phenotypes and evidence for c-kit function in melanoblast progenitors," Genes Dev., 5(12A): 2265-2273.
Reineke (2004) "Antibody Epitope Mapping Using Arrays of Synthetic Peptides," Methods Mol Biol 248:443-463.
Ren e al. (2004) "Silencing of the immunoglobulin heavy chain locus by removal of all eight constant-region genes in a 200-kb region," Genomics, 84:686-695.
Rich et al. (2000) "Advances in surface plasmon resonance biosensor analysis," Curr. Opin. Biotechnol. 11:54-61.
Ristevski (2005) "Making better transgenic models: conditional, temporal, and spatial approaches," Molecular Biotechnology, 29(2):153-163.
Rocca-Serra et al. (1983) "Two monoclonal antibodies against different antigens using the VH germ-line gene," Nature 304:353-5.
Rodriguez et al. (2000) "High-efficiency deleter mice show that FLPe is an alternative to Cre-loxP," Nature Genetics, 25:139-140.
Roebroek et al. (2003) "Chapter 10: Knockin Approaches," Methods in Molecular Biology, Transgenic Mouse Methods and Protocols, 209:16 pages.
Rojas et al. (2002) "Phage antibody fragments library combining a single human light chain variable region with immune mouse heavy chain variable regions," Biotechnol., 94(3):287-298.
Rudikoff et al. (1982) "Single amino acid substitution altering antigen-binding specificity," PNAS 79:1979-1983.
Sapparapu et al. (2009) "Antigen-specific proteolysis by hybrid antibodies containing promiscuous proteolytic light chains paired with an antigen-binding heavy chain," J. Biol. Chem., 284(36):24622-24633.
Sasso et al. (1993) "A Fetally Expressed Immunoglobulin $V_{H}1$ Gene Belongs to a Complex Set of Alleles," Journal of Clinical Investigation, 91:2358-2367.
Sasso et al. (1996) "Expression of the Immunoglobulin VH Gene 51p1 Is Proportional to Its Germline Gene Copy Number" Journal of Clinical Investigation, 97(9):2074-2080.
Sasso et al., (1990) "Prevalence and Polymorphism of Human $V_{h}3$ Genes," Journal of Immunology, 145(8):2751-2757.
Schelonka et al. (2005) "A Single $D_H$ Gene Segment Creates Its Own Unique CDR-H3 Repertoire and Is Sufficient for B cell Development and Immune Functions," Journal of Immunology, 175:6624-6632.
Schlissel and Baltimore (1989) "Activation of Immunoglobulin Kappa Gene Rearrangement Correlates with Induction of Germline Kappa Gene Transcription," Cell, 58:1001-1007.
Schultz et al. (2012) "Humanized mice for immune system investigation: progress, promise and challenges," Nature Reviews Immunology, 12:786-798.
Schulze et al. (2006) "Derivation, Maintenance, and Characterization of Rat Embryonic Stem Cells in Vitro," Methods in Molecular Biology, 329:45-58.
Schwartz and Cantor (1984) "Separation of Yeast Chromosome-Sized DNAs by Pulsed Field Gradient Gel Electrophoresis," Cell, 37:67-75.
Science Magazine Careers http://www.sciencemag.org/careers/2007/03/mastering-your-phdmaking-most-conference, last accessed Nov. 15, 2016.
Scott (2007) "Mice with a human touch," Nature Biotechnology, 25(10):1075-7.

(56) References Cited

OTHER PUBLICATIONS

Seals and Courtneidge (2003) "The ADAMs family of metalloproteases: multidomain; proteins with multiple functions," Genes and Development, 17(1):7-30.
Sen and Baltimore (1986) "Multiple nuclear factors interact with the immunoglobulin enhancer sequences," Cell, 46(5):705-716.
Sepulveda et al. (2003) "Binders Based on Dimerised Immunoglobulin VH Domains," J. Mol. Biol., 333:355-365.
Shmerling et al. (2005) "Strong and ubiquitous expression of transgenes targeted into the β-actin locus by Cre/lox cassette replacement," Genesis, 42(5):229-235.
Shi et al. (2006) J. Immunol. Methods 314:9-20.
Schiffer et al. (1973) "Structure of a λ-Type Bence-Jones Protein at 3.5-Å," Biochemistry, 12:4620-4631.
Sibilia et al. (1997) "Structural Analysis of Human Antibodies to Proteinase 3 from Patients with Wegener Granulomatosis," Journal of Immunology, 159:712-719.
Sigmund (2000) "Viewpoint: Are Studies in Genetically Altered Mice Out of Control?" Arterioscler. Thomb. Vasc. Biol., 20(6):1425-1429.
Simon and Rajewsky (1990) "Antibody domain mutants demonstrate autonomy of the antigen binding site," EMBO Journal., 9(4):1051-1056.
Smith, (2002) "Gene transfer in higher animals: theoretical considerations and key concepts," Journal of Biotechnology, 99(1):1-22.
Solomon et al. (1998) "Light chain-associated amyloid deposits comprised of a novel κ constant domain," PNAS, 95:9547-9551.
Song et al. (2000) "Light chain of natural antibody plays a dominant role in protein antigen binding," Biochem. Biophys. Res. Comm., 268:390-394.
Sorrell and Kolb (2004) "Chapter XI: Targeted Modification of Mammalian Genomes," Focus on Genome Research, 6 pages.
Souroujon et al. (1989) "Polymorphisms in Human H Chain V Region Genes From the VHIII Gene Family," Journal of Immunology, 143(2):706-711.
Stamatopoulos et al. (1997) "Follicular lymphoma immunoglobulin κ light chains are affected by the antigen selection process, but to a lesser degree than their partner heavy chains," British J. Haematology, 96:132-146.
Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 2 pages original (pp. 3-11 are p. 2 of the original, enlarged).
Storb et al. (1986) "Transgenic Mice with μ and κ Genes Encoding Antiphosphorycholine Antibodies," J. Exp. Med., 164:627-664.
Sui et al. (2009) "Structural and functional bases for broad-spectrum neutralization of avian and human influenza A viruses," Nature Structural & Molecular Biology, 16(3):265-273.
Sun et al. (1994) "Antigen recognition by an antibody light chain," J. Biol. Chem., 269(1):734-738.
Suzuki et al. (1995) "Representation of Rearranged $V_H$ Gene Segments in the Human Adult Antibody Repertoire," Journal of Immunology, 154:3902-3911.
Swarthout et al. (2011) "Zinc Finger Nucleases: A new era for transgeenic animals," Annals of Neurosciences, 18(1):25-28.
Szent-Gyorgy et al. (2013) "Malachite Green Mediates Homodimerization of Antibody $V_L$ Domains to Form a Fluorescent Ternary Complex with Singular Symmetric Interfaces," J. Mol. Biol., 425:4595-4613.
Taki et al. (1993) "Targeted Insertion of a Variable Region Gene into the Immunoglobuliin Heavy Chain Locus," Science, 262:1268-1271.
Taylor (1992) "A transgenic mouse that expresses a diversity of human sequence heavy and light chain immunoglobulins," Nucl. Acids Res. 20:6287-6295).
Timetable for Mouse ES Cells course at Wellcome Trust Sanger Institute Oct. 26, 2009-Nov. 8, 2009 (black and white), 5 pages original (pp. 6-13 are pp. 1-5 of the original, enlarged).
Timetable for Mouse ES Cells course at Wellcome Trust Sanger Institute Oct. 26, 2009-Nov. 8, 2009 (greyscale), 5 pages original (pp. 6-13 are pp. 1-5 of the original, enlarged).
Tomer (2000) "Characterization of a discontinuous epitope of the human immunodeficiency virus ~HIV! core protein p24 by epitope excision and differential chemical modification followed by mass spectrometric peptide mapping analysis," Protein Science: 9:487-496 (first named author is Hochleitner).
Tonegawa (1983) "Somatic generation of antibody diversity," Nature, 302(5909):575-581.
Torres and Kuhn (1997) Laboratory Protocols for Conditional Gene Targeting, 37-40.
Tsybovsky et al. (2004) "Folding and stabiilty of chimeric immunofusion VL-barstar," Biochem (Moscow), 69(9):939-948.
Tuaillon et al. (1993) "Human immunoglobulin heavy-chain minilocus recombination in transgenic mice: Gene-segment use in μ, and y transcripts," PNAS, 90:2734-2743.
Tuaillon (2000) "Repertoire analysis in human immunoglobulin heavy chain minilocus transgenic, [mu]MT/ [mu]MT mice," Molecular Immunology, 37(5):221-231.
Valenzuela et al (2003) "High-throughput engineering of the mouse genome coupled with high-resolution expression analysis," Nat. Biotechnol. 21:652-659.
Van Den Beucken et al. (2001) "Building novel binding ligands to B7.1 and B7.2 based on human antibody single variable light chain domains," J. Mol. Immunol., 310:591-601.
Van Ness et al. (1981) "Transcription of the unrearranged mouse C kappa locus: sequence of the initiation region and comparison of activity with a rearranged V kappa-C kappa gene," Cell, 27:593-602.
Verkoczy et al. (2010) "Autoreactivity in an HIV-1 broadly reactive neutralizing antibody variable region heavy chain induces immunologic tolerance," Proc. Natl. Acad. Sci. U.S.A., 107(1): 181-186.
Wagner et al. (1994) "Antibodies generated from human immunoglobulin miniloci in transgenic mice," Nucleic Acids Research, 22(8):1389-1393.
Wagner et al. (1994) "The diversity of antigen-specific monoclonal antibodies form transgenic mice bearing human immunoglobulin gene miniloci," Eur. J. Immunol., 24:2673-2681.
Wallace et al. (2007) "Manipulating the mouse genome to engineer precise functional syntenic replacements with human sequence," Cell, 128(1):197-209.
Wang and Palese (2009) "Universal epitopes of influenza virus hemagglutinins?," Nature Structural & Molecular Biology, 16(3):233-234.
Warren and Nie (1998) Science 281: 2016-2018.
Watson and Crick (2002) Molekulyarnaya biotekhnologiya. Printsipy i primeneniye, Moscow Mir., 45-47 and English translation.
Williams et al. (1996) "Sequence Evolution of the Human Germline V lambda Repertoire," J. Mol. Biol., 264(2):220-232.
Xu et al. (2000) "Diversity in the CDR3 Region of VHIs Sufficient for Most Antibody Specificities," Immunity, 13:37-45.
Yamada et al. (1991) "Preferential Utilization of Specific Immunoglobulin Heavy Chain Diversity and Joining Segments in Adult Human Peripheral Blood B Lymphocytes," Journal of Experimental Medicine, 173:395-407.
Yantha et al. (2010) "Unexpected Acceleration of Type 1 Diabetes by Transgenic Expression of B7-H1 in NOD Mouse Peri-Islet Glia," Diabetes, 59:2588-2596.
Yu et al. (2008) "Interaction between Bevacizumab and Murine VEGF-A: A Reassessment," Investigative Ophthalmology & Visual Science, 49(2):522-527.
Zhang et al. (1998) "A new logic for DNA engineering using recombination in *Escherichia coli*," Nature Genetics, 20:123-138.
Zheng et al. (2000) "Engineering mouse chromosomes with Cre-loxP: range, efficiency, and somatic applications," Molecular and Cellular Biology, 20(2):648-655.
Zhou et al., (2009) "Developing tTA transgenic rats for inducible and reversible gene expression," International Journal of Biological Sciences, 5:171-181.
Zou et al. (1994) Cre-loxP-mediated gene replacement: a mouse strain producing humanized antibodies, Current Biology, 4:1099-1103.

(56) References Cited

OTHER PUBLICATIONS

Zou et al. (2007) "Heavy chain-only antibodies are spontaneously produced in light chain-deficient mice," J. Exp. Med. 204(13):3271-3283.

Communication in Cases for which No Other Form is Applicable for PCT/US2012/026416, 9 pages (dated Jun. 7, 2013).

Communication in Cases for Which No Other Form Is Applicable for PCT/US2012/069981, 18 pages (dated Jul. 3, 2013).

Declaration Under C.F.R. § 1.132 Dr. Andrew Murphy dated Jul. 16, 2014.

Declaration Under C.F.R. § 1.132 Dr. Jürgen Roes Dated Jul. 19, 2014.

Declaration Under C.F.R. § 1.131 Inventors: Lynn Macdonald, Cagan Gurer, Karolina Hosiawa, Sean Stevens, and Andrew Murphy Dated Dec. 1, 2015.

EP Examination Report with respect to EP 11741730.3 dated Jan. 23, 2015.

European Search Report with respect to EP12192727, dated Mar. 7, 2013.

European Search Report with respect to EP12195716, dated Jan. 29, 2013.

Extended European Search Report with respect to EP14154918.8, dated Aug. 27, 2014.

Extended European Search Report with respect to EP14176593.3, dated Nov. 19, 2014.

Extended European Search Report with respect to EP15173007.4, dated Oct. 5, 2015.

Final Office Action with Respect to U.S. Appl. No. 13/756,889, dated Nov. 6, 2015.

Non-Final Office Action with Respect to U.S. Appl. No. 13/756,889, dated Dec. 1, 2016.

International Search Report & Written Opinion with respect to PCT/US2011/041366, dated Sep. 22, 2011.

International Search Report & Written Opinion with respect to PCT/US2011/041370, dated Sep. 22, 2011.

International Search Report & Written Opinion with respect to PCT/US2012/026416, dated Jun. 25, 2012.

International Search Report & Written Opinion with respect to PCT/US2012/069981, dated Mar. 20, 2013.

International Search Report & Written Opinion with respect to PCT/US2013/024295, dated Apr. 24, 2013.

International Search Report & Written Opinion with respect to PCT/US2011/046196, dated Oct. 17, 2011.

International Search Report & Written Opinion with respect to PCT/US2015/021884, dated Oct. 13, 2015.

International Search Report & Written Opinion with respect to PCT/US2012/060487, dated Feb. 1, 2013.

Summons to Attend Oral Proceedings with respect to EP 11741730.3 mailed Sep. 28, 2015.

Invitation to Pay Additional Fees and, Where Applicable, Protest Fee for PCT/US2015/021892, dated Aug. 10, 2015.

International Search Report & Written Opinion with respect to PCT/US2015/021892, dated Nov. 4, 2015.

Statement of Relatedness under MPEP 2001.06 with Respect to U.S. Appl. No. 15/925,501, dated Aug. 23, 2018.

* cited by examiner

$V_L$ ANTIGEN BINDING PROTEINS EXHIBITING DISTINCT BINDING CHARACTERISTICS

CROSS-REFERENCE TO RELATED APPLICATIONS

This application is a divisional application of U.S. application Ser. No. 14/664,750, filed Mar. 20, 2015, now abandoned, which claims benefit under 35 U.S.C. § 119(e) of U.S. Provisional Patent Application No. 61/968,896, filed Mar. 21, 2014, U.S. Provisional Patent Application No. 62/088,117, filed Dec. 5, 2014, and U.S. Provisional Patent Application No. 62/079,078, filed Nov. 13, 2014, each of which applications is hereby incorporated by reference.

TECHNICAL FIELD

This invention generally relates to $V_L$ antigen binding proteins that bind small molecules and/or characterizing VL antigen binding protein interactions and using the information derived from the characterization to sort $V_L$ antigen binding proteins into groups which can be used as a guide for the selection of an antigen binding $V_L$ protein with a binding characteristic not exhibited by conventional antibodies.

BACKGROUND

Antibodies have emerged as a promising modality for biologic diagnostics and/or therapy. For example, neutralizing antibodies can intercept and inactivate a pathogen before it establishes reaches an infection. Antagonistic antibodies can interfere with dysregulated signaling prevalent in, e.g., tumor progression or autoimmunity, and agonistic antibodies can be used to enhance immune responses. These abilities are based, in part, on the antibodies' specific recognition of and affinity to epitopes, the antigenic sites to which antibodies bind. A large number of antibodies may be generated against one target antigen, and each antibody may vary substantially in terms of either or both affinity and epitope recognition. Additionally, traditional antibody-based design may be limited because antigen binding sites in the conventional antibodies are not well suited to all antigens. The present invention encompasses the recognition that there remains a need for improvement and diversification of immunoglobulin-based therapeutic design.

SUMMARY

Various aspects and embodiments described herein are based in part on the surprising discovery that genetically modified non-human animals that express binding proteins that contain immunoglobulin light chain variable domains operably linked to a heavy chain constant region and immunoglobulin light chain variable domains operably linked to a light chain constant region can solve various problems recognized herein and/or can provide surprising results. For example, non-human animals whose genome includes both (i) an immunoglobulin heavy chain locus containing unrearranged human light chain gene segments (e.g., $V_L$ and $J_L$ gene segments); and (ii) an immunoglobulin light chain locus containing unrearranged human light chain gene segments (e.g., $V_L$ and $J_L$ gene segments) can provide more diversified repertoire of antigen-binding proteins, e.g., $V_L$ binding proteins, which have been difficult to obtain from the conventional humanized non-human animals. The $V_L$ antigen binding proteins generated in the genetically engineered animals disclosed herein bind to small molecules with a higher affinity than may be achieved by conventional antibodies, and may also exhibit one or more binding characteristics or traits that are distinct from those exhibited by conventional antibodies.

Generally, a $V_L$ antigen binding protein as disclosed herein comprises a hybrid immunoglobulin chain comprising an immunoglobulin light chain variable domain that specifically binds a small molecule and that is operably linked to a heavy chain constant region. $V_L$ antigen binding protein may also comprises first and second immunoglobulin light chain variable domains, wherein the first and the second immunoglobulin light chain variable domains are associated to form a binding pocket that specifically binds a small molecule. In some embodiments, the present invention provides an antigen-binding protein consisting essentially of first and second immunoglobulin light chain variable domains that are associated to form a binding pocket, wherein the antigen-binding protein specifically binds a small molecule.

In some embodiments, the first immunoglobulin light chain variable domain operably linked to a heavy chain constant domain. This hybrid $V_L$-$C_H$ immunoglobulin chain is derived from a light chain variable ($V_L$) gene segment and a light chain joining ($J_L$) gene segment operably linked to a heavy chain constant region gene. The second immunoglobulin light chain variable domain may be operably linked to a light chain constant domain ($V_L$-$C_L$).

In some embodiments, each chain of a $V_L$ antigen binding protein lacks an amino acid sequence encoded by and/or derived from an immunoglobulin heavy chain variable region gene segment.

In some embodiments, the first immunoglobulin light chain variable domain is encoded by a rearranged light chain variable region gene derived from a human Vκ gene segment selected from the group consisting of Vκ4-1, Vκ1-5, Vκ3-15, Vκ3-20, and Vκ1-33. In another embodiment, the first immunoglobulin light chain variable domain derived from a Jκ gene segment selected from the group consisting of Jκ1, Jκ3, Jκ4 and Jκ5. In another embodiment, the first immunoglobulin light chain variable domain is derived from a Vκ1-5 gene segment. In another embodiment, the first immunoglobulin light chain variable domain is derived from a Vκ1-5 gene segment, and the second immunoglobulin light chain domain is derived from a Vκ3-20 gene segment. In another embodiment, the first immunoglobulin light chain variable domain is derived from a Vκ1-5 gene segment, and a Jκ gene segment selected from the group consisting of Jκ3, Jκ4 and Jκ5. In one embodiment, the first immunoglobulin light chain variable domain is derived from a Vκ4-1 gene segment. In another embodiment, the first immunoglobulin light chain variable domain is derived from a Vκ4-1 gene segment and a Jκ1 gene segment. In one embodiment, the first immunoglobulin light chain variable domain is derived from a Vκ4-1 gene segment and the second immunoglobulin light chain variable domain is derived from a Vκ4-1 or Vκ3-20 gene segment. In one embodiment, the first immunoglobulin light chain variable domain is derived from a Vκ3-20 gene segment. In another embodiment, the first immunoglobulin light chain variable domain is derived from a Vκ3-20 gene segment and a Jκ1 or a Jκ2 gene segment. In one embodiment, the first immunoglobulin light chain variable domain is derived from a Vκ3-20 gene segment and the second immunoglobulin light chain variable domain is derived from a Vκ4-1 or Vκ1-5 gene segment. In one embodiment, the first immunoglobulin light chain variable domain is derived from a Vκ3-15 gene segment. In another embodiment, the first immunoglobulin light chain variable domain is derived from a Vκ3-15 gene segment and a Jκ5 gene segment. In one embodiment, the first immunoglobulin light chain variable domain is derived from a Vκ3-15 gene segment and the second immunoglobulin light chain variable domain is derived from a Vκ1-39 gene segment. In other embodiments, the first and second variable domains are derived from respective $V\kappa_1$:$J\kappa_1 V\kappa_2$:$J\kappa_2$ gene segments as set forth in Table A.

TABLE A

| First Variable Domain | | Second Variable Domain | |
|---|---|---|---|
| $V\kappa_1$ | $J\kappa_1$ | $V\kappa_2$ | $J\kappa_2$ |
| 3-20 | 4 | 4-1 | 2 |
| 3-20 | 4 | 1-5 | 2 |
| 3-20 | 3 | 4-1 | 1 |
| 4-1 | 1 | 4-1 | 3 |
| 4-1 | 1 | 3-20 | 3 |
| 4-1 | 1 | 3-20 | 2 |
| 4-1 | 3 | 3-20 | 2 |
| 1-33 | 3 | 3-20 | 5 |
| 1-33 | 1 | 1-33 | 3 |
| 3-15 | 5 | 1-39 | 3 |
| 1-5 | 5 | 3-20 | 1 |
| 1-5 | 5 | 3-20 | 2 |
| 1-5 | 4 | 3-20 | 1 |
| 1-5 | 4 | 3-20 | 2 |
| 1-5 | 4 | 3-20 | 3 |
| 1-5 | 3 | 3-20 | 2 |
| 1-5 | 3 | 3-20 | 3 |

In some embodiments, the CDR3 length of the hybrid $V_L$-$C_H$ immunoglobulin chain is shorter than the CDR3 length of the light second immunoglobulin light chain variable domain linked to the light chain constant domain ($V_L$-$C_L$). In some embodiments, the CDR3 of the hybrid immunoglobulin light chain is at least one amino acid shorter than the CDR3 of the light chain. In other embodiments, the CDR3 lengths differ by at least two amino acids. In other embodiments, the CDR3 lengths differ by at least 3 amino acids. In other embodiments, the CDR3 lengths differ by at least 4 amino acids. In some embodiments, the CDR3 of the hybrid immunoglobulin chain is 6 amino acids in length, and the CDR3 of the light chain is about 9 amino acids in length.

In some certain embodiments, the heavy chain constant region is from a non-human animal. In some embodiments, the light chain constant region is from a non-human animal. In some embodiments, the heavy chain constant region is selected from a CH1, a hinge, a CH2, a CH3, a CH4, and a combination thereof. In some embodiments, the heavy chain constant region comprises a CH1, a hinge, a CH2, and a CH3.

In some embodiments, the first and/or the second immunoglobulin light chain variable domain is a human immunoglobulin light chain variable domain. In some embodiments, the first and/or the second immunoglobulin light chain variable domain is from a rodent selected from a mouse and a rat.

In some embodiments, the $V_L$ antigen binding protein disclosed herein binds the small molecule with higher affinity than an antigen-binding protein comprising immunoglobulin light and heavy chain variable domains. In some embodiments, the $V_L$ antigen binding protein specifically binds a small molecule with a $K_D$ of less than 50 nM. In other embodiments, the $K_D$ of the $V_L$ antigen binding protein is less than 40 nM. In additional embodiments, the $K_D$ of the $V_L$ antigen binding protein is less than 30 nM. In another embodiment, the $K_D$ of the $V_L$ antigen binding protein is less than 20 nM. In another embodiment, the $K_D$ of the $V_L$ antigen binding protein is less than 10 nM.

In one aspect, provided herein are cells or nucleic acids comprising a rearranged light chain variable region gene encoding a variable domain of a hybrid immunoglobulin chain or a light chain of a $V_L$ antigen binding protein that specifically binds a small molecule as disclosed herein, and methods of obtaining such cells or nucleic acids.

In some embodiments, methods are provided for obtaining a $V_L$ antigen binding protein specific for a small molecule, which may include obtaining a cells or nucleic acid sequences that comprise and/or encode one or more immunoglobulin light chain variable ($V_L$) domains of the $V_L$ antigen binding protein that binds a small molecule. The methods generally comprise isolating from a genetically modified non-human animal as disclosed herein a $V_L$ binding protein that binds a small molecule and/or a cell comprising a nucleic acid sequence that encodes a $V_L$ antigen binding protein, wherein the $V_L$ binding protein specifically binds a small molecule.

Genetically engineered non-human animals disclosed herein include, e.g., mammals and, in particular embodiments, rodents (e.g., mice, rats, or hamsters). In some embodiments, non-human animals include birds, e.g., chickens. In various embodiments, the rodent is selected from a mouse and a rat.

In some embodiments, a genome of a non-human animal as disclosed herein includes both (i) an immunoglobulin heavy chain locus containing unrearranged human light chain gene segments (e.g., $V_L$ and $J_L$ gene segments) and (ii) an immunoglobulin light chain locus containing unrearranged human light chain gene segments (e.g., $V_L$ and $J_L$ gene segments). In some embodiments, the unrearranged human immunoglobulin $V_L$ and $J_L$ gene segments of (i) are present at the endogenous immunoglobulin heavy chain locus in the genome. In some embodiments, the non-human animal lacks all endogenous functional $V_H$, $D_H$ and $J_H$ gene segments. In some embodiments, the non-human animal lacks all endogenous, functional $V_H$, $D_H$, and $J_H$ gene segments, and the non-human animal comprises an Adam6a gene, an Adam6b gene, or both. In some certain embodiments, the Adam6a gene, Adam6b gene, or both are positioned ectopically in the genome.

In some embodiments, the unrearranged human immunoglobulin $V_L$ and $J_L$ gene segments of (ii) are present at an endogenous immunoglobulin light chain locus of the non-human animal. In some certain embodiments, the endogenous immunoglobulin light chain locus is a κ light chain locus.

In some embodiments, the unrearranged human immunoglobulin $V_L$ and $J_L$ gene segments of (i) are human Vκ and Jκ gene segments. In some embodiments, the unrearranged human immunoglobulin $V_L$ and $J_L$ gene segments of (ii) are human Vκ and Jκ gene segments. In some embodiments, the unrearranged human immunoglobulin $V_L$ and $J_L$ gene segments of (ii) are human Vκ and Jκ gene segments, and the light chain constant region nucleic acid sequence is a mouse Cκ (region nucleic acid sequence or a rat Cκ (region nucleic acid sequence.

In some embodiments, the non-human animal comprises a cell that expresses a $V_L$ antigen binding protein that specifically binds a small molecule. In some embodiments, the cell is a lymphocyte, e.g., an NK cell, a T cell or a B cell. In some embodiments, the cell expresses a $V_L$ binding protein comprising a hybrid $V_L$-$C_H$ chain. In some embodiments, the $V_L$ binding protein comprises two identical immunoglobulin light chain variable domains. In other embodiment, the $V_L$ binding protein comprises two immunoglobulin light chain variable domains with heterogeneous sequences.

In some embodiment, the cell isolated from an animal as disclosed herein is a B cell. In other embodiments, the cell is a memory B cell.

Nucleic acids comprising a rearranged light chain variable region gene encoding a variable domain of a hybrid immunoglobulin chain or a light chain of a $V_L$ antigen binding protein that specifically binds a small molecule may also be isolated by identifying, e.g., from a cell isolated from a non-human animal disclosed herein, first and second nucleic acid sequences that encode the first and the second immunoglobulin light chain variable domains of a $V_L$ binding protein that specifically binds the small molecule. In some embodiments, the methods of obtaining a cell and/or nucleic acid as disclosed herein comprises (a) immunizing a non-human animal with a small molecule or the small molecule linked to a carrier, wherein the non-human animal comprises in its genome (i) unrearranged human immunoglobulin light chain variable ($V_L$) and light chain joining ($J_L$) gene segments operably linked to a non-human heavy chain constant region nucleic acid sequence, and (ii) unrearranged human immunoglobulin light chain variable ($V_L$) and light chain joining ($J_L$) gene segments operably linked to a non-human light chain constant region nucleic acid sequence, (b) isolating a cell from the immunized non-human animal, wherein the cell comprises first and second nucleic acid sequences that encode first and second immunoglobulin light chain variable domains; and (c) identifying from the cell the first and the second nucleic acid sequences that encode the first and the second immunoglobulin light chain variable domains of a $V_L$ binding protein that specifically binds the small molecule.

In some embodiments, immunizing a non-human animal comprises priming the non-human animal with the small molecule or the small molecule linked to a carrier, allowing the non-human animal to rest for a period of time, and re-immunizing the animal with the small molecule or the small molecule linked to the carrier. In some embodiments, the period of time is a few days, at least a week, at least two weeks, at least three weeks, at least four weeks, or at least one month. In some embodiments, immunizing the non-human animal comprises allowing the non-human animal to mount an immune response.

In some embodiments, the cell is obtained through fluorescence-activated cell sorting (FACS) or flow cytometry. In some embodiments, the cell is obtained from a tissue of the immunized non-human animal, and wherein the tissue is selected from the group consisting of spleen, lymph node, blood and bone marrow.

In some embodiments, methods of the present invention further comprise fusing the lymphocyte with a cancer cell, e.g., to make a hybridoma. In some certain embodiments, the cancer cell is a myeloma cell. Accordingly, also provided herein are hybridomas and nucleic acids isolated therefrom, wherein the hybridomas express a $V_L$ binding protein specific for a small molecule.

In some embodiments, methods for making a $V_L$ antigen binding protein specific for a small molecule may also comprise: expressing a first and a second nucleic acid that encode a first and a second immunoglobulin light chain variable domain of a $V_L$ antigen binding protein specific for the small molecule in an expression system suitable for expressing the first and second immunoglobulin light chain variable domains as a dimer that specifically binds the small molecule.

Also provided is a non-human animal comprising (a) in its genome: (i) unrearranged human immunoglobulin light chain variable ($V_L$) and light chain joining ($J_L$) gene segments operably linked to a non-human heavy chain constant region nucleic acid sequence, and (ii) unrearranged human immunoglobulin light chain variable ($V_L$) and light chain joining ($J_L$) gene segments operably linked to a non-human light chain constant region nucleic acid sequence; and (b) a $V_L$ antigen binding protein that specifically binds a small molecule.

In some embodiments, the non-human animal exhibits a 2-fold or more, e.g., at least a 3-fold, at least a 4-fold, at least a 5-fold, at least a 6-fold, at least a 7-fold, at least a 8-fold, at least a 10-fold, or a 20-fold or more antigen-positive B cells than a reference non-human animal. In some embodiments, the reference non-human animal expresses chimeric antibodies upon immunization, wherein the chimeric antibodies have heavy chains comprising human $V_H$ domains and mouse $C_H$ domains and light chains having human $V_L$ domains and mouse $C_L$ domains. In some certain embodiments, the reference non-human animal is a wild-type non-human animal. In some embodiments, immunization comprises priming the non-human animal with the small molecule or the small molecule linked to a carrier, allowing the non-human animal to rest for a period of time, and re-immunizing the animal with the small molecule or the small molecule linked to the carrier. In some embodiments, the period of time is a few days, at least a week, at least two weeks, at least three weeks, at least four weeks, or at least one month. In some embodiments, the antigen-positive B cells are memory B cells.

In some embodiments, the non-human animal exhibits at least a 2-fold, at least 3-fold, at least 4-fold, or at least 5-fold or higher antibody titer than a reference non-human animal. In some certain embodiments, the reference non-human animal is a genetically modified mouse, which expresses chimeric antigen-binding proteins upon immunization, and the chimeric antigen-binding proteins comprise heavy chains containing human $V_H$ domains and mouse $C_H$ domains, and light chains having human $V_L$ domains and mouse $C_L$ domains. In some certain embodiments, the reference non-human animal is a wild-type non-human animal.

In some embodiments, a small molecule of the present invention is a hapten and is linked to a carrier. In some certain embodiments, the carrier comprises keyhole limpet hemocyanin (KLH), Concholepas concholepas hemocyanin (CCH), bovine serum albumin (BSA), a cationized bovine serum albumin (cBSA), or ovalbumin.

In some embodiments, a small molecule of the present invention is an organic compound whose molecular weight is less than 6 kDa.

In one aspect, disclosed herein are methods of identifying and/or isolating antigen-specific $V_L$ antigen binding proteins that exhibit a biding characteristic not exhibited by conventional antibodies, antigen-specific $V_L$ antigen binding proteins so identified and/or isolated, nucleic acids encoding same, and/or host cells expressing same.

In one embodiment, a method of identifying one or more $V_L$ antigen binding proteins that exhibit a unique binding characteristic when specifically binding to an antigen not exhibited by conventional antibodies that also specifically bind the antigen as disclosed herein comprises (a) profiling one or more binding characteristics of each of a plurality of immunoglobulin proteins that specifically bind an antigen, wherein the plurality of immunoglobulin proteins comprises $V_L$ antigen binding proteins and conventional antibodies, wherein each $V_L$ antigen binding protein comprises a hybrid immunoglobulin chain comprising (i) a variable domain derived from one or more light chain variable region gene segments and (ii) a constant domain derived from one or more heavy chain constant region gene segments, wherein each conventional antibody comprises an immunoglobulin heavy chain variable region derived from one or more heavy chain variable region and an immunoglobulin light chain variable region gene segment derived from one or more light chain variable region gene segments; (b) binning the plurality of immunoglobulin proteins into one or more groups based on at least one binding characteristic of each of the immunoglobulin proteins, wherein $V_L$ antigen binding proteins and conventional antibodies that exhibit a similar binding characteristic are binned into the same group; and (c) identifying a group comprising all or substantially all $V_L$ antigen binding proteins.

In some embodiments, one or more binding characteristics of each of the plurality of immunoglobulin proteins is profiled by differential antigen disruption. In some embodiments, methods as disclosed herein further comprise mapping one or more epitopes of the antigen bound by each of the plurality of immunoglobulin proteins; wherein immunoglobulin proteins binding the same epitope of the antigen are binned into the same functional group. In some embodiments, mapping one or more epitopes of the antigen bound by each of the plurality of immunoglobulin proteins comprises an epitope mapping assay selected from the group consisting of cross-blocking assay, alanine scanning of antigen mutants, peptide blots, peptide cleavage analysis, epitope excision, epitope extraction, chemical modification of the antigen, and a combination thereof.

In the methods disclosed herein, one or more binding characteristics of a plurality of antigen binding proteins is determined using antigen immobilized on a solid surface. In some embodiments, the solid surface comprises biosensor chips or polystyrene beads. In some embodiments, the antigen is modified after immobilization and prior to profiling. Modification may be effected with a chemical (e.g., Tris (2-carboxyethyl) phosphine hydrochloride (TCEP●HCl)/Iodoacetamide, N-ethyl-N'-(dimethylaminopropyl) carbodiimide (EDC)/ethanolamine, iodoacetamide and hydrazine, p-hydroxyphenylglyoxal (HPG), hydrogen peroxide, N-bromosuccinimide, N-acetylimidazole, tetranitromethane, arsanilic acid, dansyl chloride, glutaraldehyde, ninhydrin, diethylpyrocarbonate (DEPC), sulfosuccinimidyl acetate (sulfo-NHS-acetate), polyethylene glycol 5000 (PEG-5000), 7-hydroxycoumarin-3-carboxylic acid, succinimidyl ester, and a combination thereof) and/or an enzyme (e.g., porcine trypsin, endoproteinase Glu-C, endoproteinase Asp-N, chymotrypsin, endoproteinase Lys-C, and endoproteinase Arg-C, pepsin, papain, thermolysin, subtilisin, protease K, bromelain sulfhydryl-specific protease (ficin), and a combination thereof).

Binning according to the methods disclosed herein may comprise principle component analysis (PCA) and/or hierarchical clustering. In one embodiment, two principle components are selected for presenting data. In one embodiment, binning comprises principal component analysis. In another embodiment, binning comprises hierarchical clustering. In another embodiment, binning comprises both principal component analysis and hierarchical clustering. Binning may be based on one or more binding profiles comprising a binding signal intensity of each immunoglobulin protein to a panel of chemically and/or enzymatically disrupted/modified antigen surfaces as described above. Such binning results may be aligned with other typical assay data for a group of immunoglobulin proteins such as association constants, dissociation constants, equilibrium constants, binding specificities toward antigen homologs from various species or related family members of the same species, functional activity data (e.g., ability to block ligand blocking, antigen phosphorylation and/or antigen internalization into cells) or any combination thereof. Alignment results, which may be displayed as a "tree-table," e.g., a hierarchical clustering dendrogram derived from differential antigen disruption binding data is aligned with other various assay data for each immunoglobulin protein, may be used to reveal behavior patterns among the immunoglobulin proteins that share a bin.

Some profiling methods as disclosed herein further comprise (d) isolating one or more $V_L$ antigen binding proteins binned in a functional group identified as comprising all or substantially all $V_L$ antigen binding proteins and/or (e) confirming that the one or more $V_L$ antigen binding proteins isolated binds one or more epitopes of the antigen that are not recognized by conventional antibodies. Confirmation that the one or more $V_L$ antigen binding proteins isolated binds one or more epitopes of the antigen that are not recognized by conventional antibodies may comprise a high throughput competitive binding protein assay.

The amino acid sequence and/or nucleic acid sequence encoding same may be determined for any of the one or more $V_L$ antigen binding proteins isolated according to a profiling method disclosed herein. Accordingly, also provided herein are $V_L$ antigen binding proteins isolated according to a profiling method disclosed herein, isolated nucleic acids comprising a nucleotide sequence encoding a CDR of the variable region of a hybrid immunoglobulin chain of a $V_L$ antigen binding protein so identified and/or isolated, and host cells expressing such nucleic acids.

Also provided herein is a method of identifying one or more epitopes of an antigen that are masked to conventional antibodies and are recognized by one or more antigen specific $V_L$ antigen binding proteins comprising identifying one or more $V_L$ antigen binding protein that bind epitopes of the antigen unrecognized by conventional antibodies using methods as disclosed herein and (b) mapping the one or more epitopes recognized by the identified one or more antigen specific antigen binding proteins.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE FIGURES

The Drawing included herein, which is comprised of the following Figures, is for illustration purposes only not for limitation.

Figure 1:
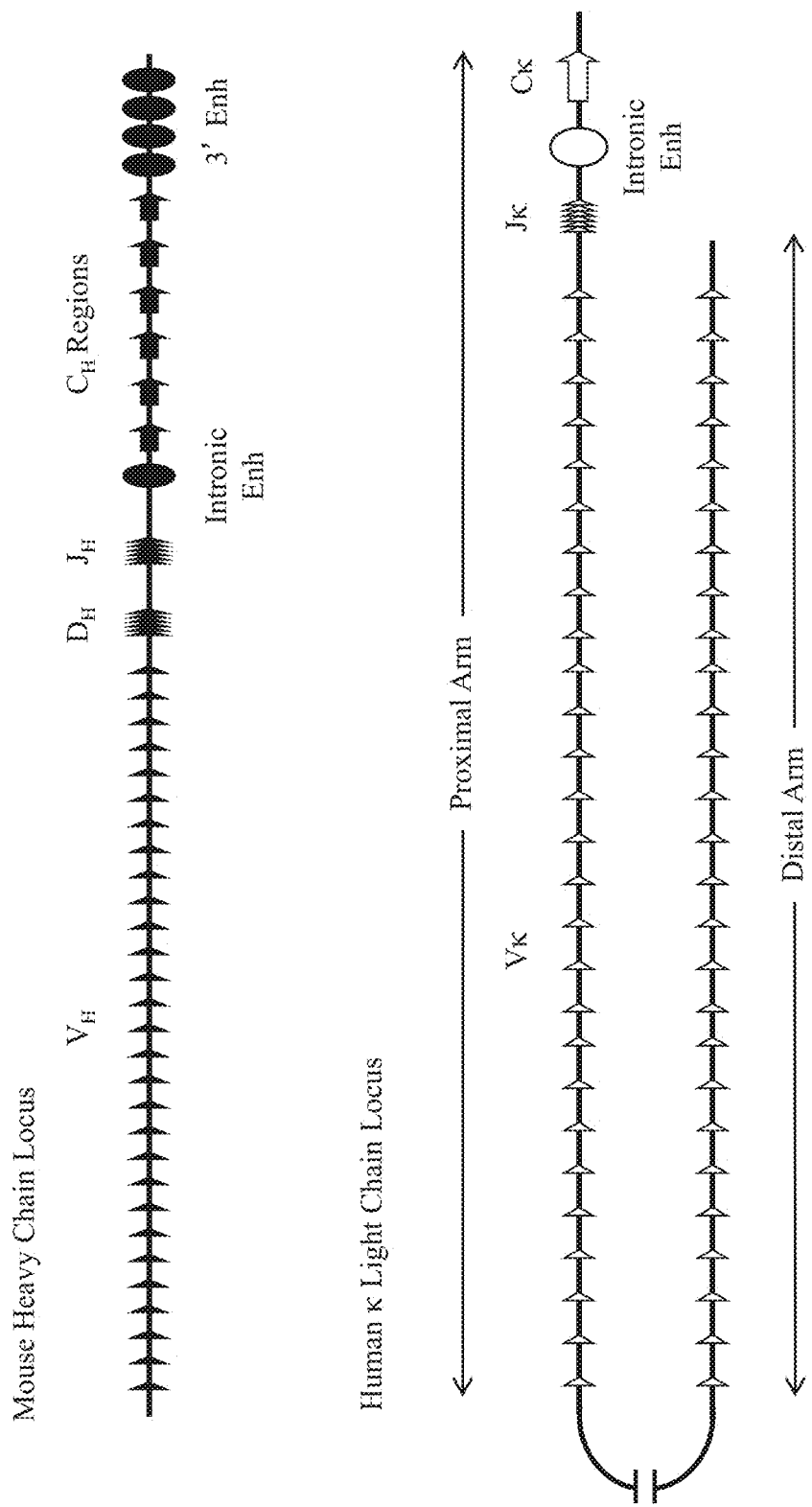
FIG. 1 illustrates a schematic (not to scale) of the mouse heavy chain locus, at top and a schematic (not to scale) of the human κ light chain locus, at bottom. The mouse heavy chain locus is about 3 Mb in length and contains approximately 200 heavy chain variable ($V_H$) gene segments, 13 heavy chain diversity ($D_H$) gene segments and 4 heavy chain joining ($J_H$) gene segments as well as enhancers (Enh) and heavy chain constant ($C_H$) regions. The human κ light chain locus is duplicated into distal and proximal contigs of opposite polarity spanning about 440 kb and 600 kb, respectively. Between the two contigs is about 800 kb of DNA that is believed to be free of Vκ gene segments. The human κ light chain locus contains about 76 Vκ gene segments, 5 Jκ gene segments, an intronic enhancer (Enh) and a single constant region (Cκ).

The term "biologically active" includes a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "carrier," in the context of a small molecule, e.g., a carrier attached to a small molecule, refers to a macromolecule, generally a protein, to which the small molecule may be coupled to render the small molecule immunogenic.

The term "cognate," when used in the sense of "cognate with," e.g., a first $V_L$ domain that is "cognate with" a second $V_L$ domain, is intended to include reference to the relation between two $V_L$ domains from a same binding protein made by a mouse in accordance with the invention. For example, a mouse that is genetically modified in accordance with an embodiment of the invention, e.g., a mouse having a heavy chain locus in which $V_H$, $D_H$, and $J_H$ regions are replaced with $V_L$ and $J_L$ regions, makes antibody-like binding proteins that have two identical polypeptide chains made of the same mouse $C_H$ region (e.g., an IgG isotype) fused with a first human $V_L$ domain, and two identical polypeptide chains made of the same mouse $C_L$ region fused with a second human $V_L$ domain. During clonal selection in the mouse, the first and the second human $V_L$ domains were selected by the clonal selection process to appear together in the context of a single antibody-like binding protein. Thus, first and second $V_L$ domains that appear together, as the result of the clonal selection process, in a single antibody-like molecule are referred to as being "cognate." In contrast, a $V_L$ domain that appears in a first antibody-like molecule and a $V_L$ domain that appears in a second antibody-like molecule are not cognate, unless the first and the second antibody-like molecules have identical heavy chains (i.e., unless the $V_L$ domain fused to the first human heavy chain region and the $V_L$ domain fused to the second human heavy chain region are identical).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germ line sequence or a rearranged or unrearranged sequence, and, for example, by a naive or a mature B cell or a T cell. A CDR can be somatically mutated (e.g., vary from a sequence encoded in an animal's germ line), humanized, and/or modified with amino acid substitutions, additions, or deletions. In some circumstances (e.g., for a CDR3), CDRs can be encoded by two or more sequences (e.g., germ line sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "comparable" includes two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" to describe a conservative amino acid substitution includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is one that that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, a substitution is deemed to be "moderately conservative" if it has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The term "disruption," when used outside the context of "differential antigen disruption," includes the result of an event that interrupts (e.g., via homologous recombination) a DNA. In some embodiments, a disruption may achieve or represent a deletion, insertion, inversion, modification, replacement, substitution, or any combination thereof, of a DNA sequence(s). In some embodiments, a disruption may achieve or represent introduction of a mutation, such as a missense, nonsense, or frame-shift mutation, or any combination thereof, in a coding sequence(s) in DNA. In some embodiments, a disruption may occur in a gene or gene locus endogenous to a cell. In some embodiments, insertions may include the insertion of entire genes or fragments of genes, e.g. exons, in to an endogenous site in a cell or genome. In some embodiments, insertions may introduce sequences that are of an origin other than that of an endogenous sequence into which they are inserted. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or gene product (e.g., an encoded protein). In some embodiments, a disruption may truncate or fragment a gene or gene product (e.g., an encoded protein). In some embodiments, a disruption may extend a gene or gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" includes a genetic locus found in a parent or reference organism prior to introduction of a disruption (e.g., deletion, insertion, inversion, modification, replacement, substitution, or a combination thereof as described herein). In some embodiments, an endogenous locus has a sequence found in nature. In some embodiments, an endogenous locus is wild type. In some embodiments, a reference organism that contains an endogenous locus as described herein is a wild-type organism. In some embodiments, a reference organism that contains an endogenous locus as described herein is an engineered organism. In some embodiments, a reference organism that contains an endogenous locus as described herein is a laboratory-bred organism (whether wild-type or engineered).

The phrase "endogenous promoter" includes a promoter that is naturally associated, e.g., in a wild-type organism, with an endogenous gene.

The phrase "epitope-binding protein" includes a protein having at least one CDR and that is capable of selectively recognizing an epitope, e.g., is capable of binding an epitope with a KD that is at about one micromolar or lower (e.g., a $K_D$ that is about $1\times10^{-6}$ M, $1\times10^{-7}$ M, $1\times10^{-8}$ M, $1\times10^{-9}$ M, $1\times10^{-10}$ M, $1\times10^{-11}$ M, or about $1\times10^{-12}$ M). Therapeutic epitope-binding proteins (e.g., therapeutic antibodies) frequently require a $K_D$ that is in the nanomolar or the picomolar range.

"Functional," e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

The phrase "functional fragment" includes fragments of epitope-binding proteins that can be expressed, secreted, and specifically binds to an epitope with a $K_D$ in the micromolar, nanomolar, or picomolar range. Specific recognition includes having a $K_D$ that is at least in the micromolar range, the nanomolar range, or the picomolar range.

The phrase "gene segment," or "segment" includes reference to a (heavy or light) variable (V) gene segment, a diversity (D) gene segment, or a (heavy or light) joining J gene segment, which includes unrearranged sequences at immunoglobulin loci (in e.g., humans and rodents) that can participate in a rearrangement (mediated by, e.g., endogenous recombinases) to form a rearranged V/J or a rearranged V/D/J gene sequence, each of which may be operably linked to one or more (heavy or light) constant (C) gene segments. Unless indicated otherwise, the V, D, and J segments comprise recombination signal sequences (RSS) that allow for V/J recombination or V/D/J recombination according to the 12/23 rule. Gene segment also includes reference to a (heavy or light) constant region gene segment, which may comprise at the 5' end of the constant region gene segment repetitive DNA known as a switch region that allows for site-specific recombination resulting in isotype switching. A heavy chain constant region gene sequence may comprise one heavy chain constant region gene segment or a cluster of heavy chain constant region gene segments, e.g., in germline organization, the cluster of which may preferably also comprise 5' of each heavy chain constant region gene segment a switch region that allows isotype switching by site specific recombination. Unless indicated otherwise, the segments further comprise sequences with which they are associated in nature or functional equivalents thereof (e.g., for V segments promoter(s) and leader(s)).

The term "germ line" in reference to an immunoglobulin nucleic acid sequence includes a nucleic acid sequence that can be passed to progeny.

The phrase "immunoglobulin heavy chain," "heavy chain," or the like generally refers to a full-length immunoglobulin protein that includes, from amino terminus to carboxyl terminus, a heavy chain variable domain ($V_H$) and a heavy chain constant ($C_H$) domain, and includes heavy chains lacking a CH1 domain, and optionally, additionally lacking a hinge region. An immunoglobulin heavy chain sequence may be from any organism.

A "heavy chain variable domain" refers to an immunoglobulin domain having an amino acid sequence that is preferably encoded by or derived from a rearranged heavy chain variable region gene, which generally comprises sequences from a heavy chain variable ($V_H$) gene segment (or a portion thereof), a heavy chain diversity ($D_H$) gene segment (or a portion thereof), and a heavy chain joining ($J_H$) gene segment (or a portion thereof). In preferred embodiments, the heavy chain variable region gene sequence, e.g., the rearranged $V_H$-$D_H$-$J_H$ gene sequence, is derived from a repertoire of unrearranged $V_H$, $D_H$, and $J_H$ gene segments, preferably germline unrearranged $V_u$, $D_H$, and $J_H$ gene segments, capable of undergoing productive gene rearrangement, e.g., capable of joining to form an in-frame heavy chain variable region gene sequence. $V_H$ gene segments, $D_H$ gene segments or $J_H$ gene segments include $V_H$ gene segments, DH gene segments, or $J_L$ gene segments from any organism including, but not limited to, rodents (e.g., mice, rats, etc.) and humans. A heavy chain variable domain comprising somatic mutations (e.g., amino acids not encoded by the germline sequence of a $V_H$, $D_H$ and/or $J_H$ gene segment), and the rearranged heavy chain variable region gene encoding same, may regardless be considered derived from the germline $V_H$, $D_H$ and/or $J_H$ gene segments, or portions thereof, that productively rearranged to form the gene encoding heavy chain variable domain in the first instance, e.g., prior to antigen-mediated proliferation.

An immunoglobulin heavy chain variable domain typically includes, from amino terminus to carboxyl terminus three heavy chain complementarity determining regions (CDRs) and four heavy chain framework (FR) regions, e.g., FRH1-CDRH1-FRH2-CDRH2-FRH3-CDRH3-FRH4, unless otherwise specified. A $V_H$ domain may also refer to the portion of a heavy chain that extends (from N-terminus to C-terminus) from the N-terminus of the heavy chain to the N-Terminus of a heavy chain constant domain.

A heavy chain constant domain ($C_H$) refers to an immunoglobulin domain having an amino acid sequence that is preferably encoded by a heavy chain constant region gene segment, or portion thereof, from any organism, Exemplary heavy chain constant region gene segments include, but is not limited to, a Cμ gene segment, a Cδ gene segment, a Cγ (e.g., Cγ1, Cγ2, Cγ3, Cγ4) gene segment, a Cα (e.g., Cα1, Cα2) gene segment, or a Cε gene segment, which encode an IgM, IgD, IgG, IgA, or IgE heavy chain constant domain, respectively. A typical heavy chain constant region gene segment typically comprises exons each encoding a $C_H1$ domain, a hinge, a $C_H2$ domain, a $C_H3$ domain, optionally a $C_H4$ domain (e.g., in the case of IgM or IgE), and optionally a transmembrane (M) domain (e.g., in the case of membrane-bound immunoglobulin on lymphocytes). A $C_H$ domain may also refer to an immunoglobulin domain having an amino acid sequence that is encoded by a heavy chain constant region gene which lacks a functional $C_H1$ region, and optionally additionally lacks a functional hinge region. Generally, a $C_H$ domain may also refer to the portion of a heavy chain that extends (from N-terminal side to C-terminal side) from outside FR4 to the C-terminal of the heavy chain. A $C_H$ domain may also refer to the portion of a hybrid chain that extends (from N-terminal side to C-terminal side) from outside FR4 to the C-terminal of the hybrid chain.

Heavy chain constant domains with minor deviations, e.g., truncations of one, two, three or several amino acids from the C-terminal, would be encompassed by the phrase "heavy chain constant domain," as well as heavy chain constant domains with sequence modifications, e.g., 1, 2, 3, 4, 5, 6, 7, 8, 9, or 10 amino acid substitutions. Amino acid substitutions can be made at one or more positions selected from, e.g. (with reference to EU numbering of an immunoglobulin constant domain, e.g., a human IgG constant domain), 228, 233, 234, 235, 236, 237, 238, 239, 241, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, a heavy chain constant domain may be modified to exhibit enhanced serum half-life (as compared with the same heavy chain constant domain without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P). Residues are numbered according to the EU numbering system. In another non-limiting example, a heavy chain constant domain may be modified to exhibit a changed affinity to protein A, which may be useful in the isolation of bispecific antibodies, see, e.g., U.S. Pat. No. 8,586,713, incorporated herein in its entirety by reference.

The term "heterologous" includes an agent or entity from a different source. For example, when used in reference to a polypeptide, gene, or gene product or present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell" includes a cell into which a heterologous (e.g., exogenous) nucleic acid or protein has been introduced. Persons of skill upon reading this disclosure will understand that such terms include not only a particular subject cell, but also are used to include progeny of that cell. Because certain modifications may occur in succeeding generations due to either mutation or environmental influences, such progeny may not, in fact, be identical to the parent cell, but are still understood by those skilled in the art to be included within the scope of the term "host cell". In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells that may be utilized as host cells in accordance with the present disclosure include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The art-understood term "humanized" includes nucleic acids or proteins whose structures (i.e., nucleotide or amino acid sequences) include portions that correspond substantially or identically with versions of the relevant nucleic acids or proteins that are found in nature in non-human animals and that are distinguishable from corresponding versions that are found in nature in humans, and also include portions whose structures differ from those present in the non-human-animal versions and instead correspond more closely with comparable structures found in the human versions. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide with an extracellular portion whose amino acid sequence is identical or substantially identical to that of a human extracellular portion, and whose remaining sequence is identical or substantially identical to that of a non-human (e.g., mouse) polypeptide. In some embodiments, a humanized gene comprises at least a portion of a DNA sequence of a human gene. In some embodiment, a humanized gene comprises an entire DNA sequence found in a human gene. In some embodiments, a humanized protein has an amino acid sequence that comprises a portion that appears in a human protein. In some embodiments, a humanized protein has an amino acid sequence whose entire sequence is found in a human protein. In some embodiments (including, for example, some in which a humanized protein has an amino acid sequence whose entire sequence is found in a human protein), a humanized protein is expressed from an endogenous locus of a non-human animal, which endogenous locus corresponds to the homolog or ortholog of the relevant human gene encoding the protein.

The term "identity" in connection with a comparison of sequences includes identity as determined by any of a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The term "identity" includes the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgap-dna.CMP matrix.

The term "isolated" includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. A substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

A "light chain variable domain" refers an immunoglobulin domain having an amino acid sequence that is preferably encoded by or derived from a rearranged light chain variable region gene, which generally comprises sequences from a light chain variable ($V_L$) gene segment (or a portion thereof) and a light chain joining ($J_L$) gene segment (or a portion thereof). In preferred embodiments, the light chain variable region gene sequence, e.g., the rearranged $V_L$-$J_L$ gene sequence, is derived from a repertoire of unrearranged $V_L$ and/or unrearranged $J_L$ gene segments, preferably germline unrearranged $V_L$ gene segments and/or germline unrearranged $J_L$ gene segments, capable of undergoing productive gene rearrangement, e.g., capable of rearranging to form an in-frame light chain variable region gene sequence. $V_L$ gene segments or $J_L$ gene segments include $V_L$ gene segments or $J_L$ gene segments from any organism including, but not limited to, rodents (e.g., mice, rats, etc.) and humans. A light chain variable domain comprising somatic mutations (e.g., amino acids not encoded by the germline sequence of a $V_L$ and/or $J_L$ gene segment), and the rearranged light chain variable region gene encoding same, may regardless be considered derived from the germline $V_L$ and $J_L$ gene segments, or portions thereof, that productively rearranged to form the gene encoding the light chain variable domain in the first instance, e.g., prior to antigen-mediated proliferation.

An immunoglobulin light chain variable domain typically includes, from amino terminus to carboxyl terminus three light chain complementarity determining regions (CDRs) and four framework (FR) regions, e.g., FRL1-CDRL1-FRL2-CDRL2-FRL3-CDRL3-FRL4, unless otherwise specified. A $V_L$ domain may also refer to the portion of a light chain that extends (from N-terminus to C-terminus) from the N-terminus of the light chain to the N-terminus of a light chain constant domain of the light chain. A $V_L$ domain may also refer to the portion of a hybrid chain that extends (from N-terminus to C-terminus) from the N-terminus of the hybrid chain to the N-terminus of a heavy chain constant domain of the hybrid chain.

A light chain constant domain ($C_L$) refers to an immunoglobulin domain having an amino acid sequence that is preferably encoded by a light chain constant region gene from any organism, such as, but not limited to, an amino acid sequence encoded by a Cκ or Cλ gene segment, e.g., a rodent or human Cκ or Cλ gene segment Such Cκ or Cλ domains are well-known in the art. Generally, a $C_L$ domain may also refer to the portion of a light chain that extends (from N-terminus to C-terminus) outside an FRL4 to the C-terminus of the light chain.

The phrase "micromolar range" is intended to mean 1-999 micromolar; the phrase "nanomolar range" is intended to mean 1-999 nanomolar; the phrase "picomolar range" is intended to mean 1-999 picomolar.

The phrase "immunoglobulin hybrid chain," "hybrid chain," "hybrid immunoglobulin chain," or the like refers to an immunoglobulin protein that includes, from amino terminus to carboxyl, a light chain variable domain (which may or may not be somatically mutated) and a heavy chain constant domain. Generally, a hybrid chain is encoded by a rearranged light chain variable region gene sequence operably linked to a heavy chain constant region gene sequence. The light chain variable region gene sequence of a hybrid immunoglobulin chain may generally comprise sequences from light chain variable ($V_L$) gene segment (or portion thereof) and a light chain joining ($V_L$) gene segment. In preferred embodiments, the light chain variable region gene sequence, e.g., the rearranged $V_L$-$J_L$ gene sequence, encoding the hybrid chain variable domain is derived from a repertoire of unrearranged $V_L$ and $J_L$ gene segments, preferably germline unrearranged $V_L$ and $J_L$ gene segments, which are (a) capable of undergoing productive gene rearrangement, e.g., capable of rearranging to form an in-frame light chain variable region gene sequence and (b) operably linked to one or more heavy chain constant region gene segments, e.g., an unrearranged cluster of constant region gene segments or one constant region gene segment.

The phrase "non-human animal" includes a vertebrate organism that is not a human. In some embodiments, a non-human animal is a cyclostome, a bony fish, a cartilaginous fish (e.g., a shark or a ray), an amphibian, a reptile, a mammal, or a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid" in its broadest sense, includes any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" includes one or more individual nucleic acid residues (e.g., nucleotides and/or nucleosides); in some embodiments, "nucleic acid" includes an oligonucleotide chain comprising individual nucleic acid residues.

"Operably linked" also refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an rearranged immunoglobulin heavy or light chain gene sequence.

The term "polypeptide" includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

The term "recombinant" is intended to include polypeptides (e.g., B cell activating factor proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "reference" is used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest. In some embodiments, control or "reference" non-human animals (e.g., mice) are provided herein and include genetically engineered non-human animals whose genomes express traditional immunoglobulin molecules (i.e., immunoglobulins having cognate $V_H$ and $V_L$ domains). In some certain embodiments, control genetically engineered non-human animals include VELOCIMMUNE® humanized mice (see, for example, U.S. Pat. Nos. 8,502,018 and 8,642,835, which are incorporated herein by reference) and/or "ULC mice" (see US 2011-0195454A1, US 2012-0021409A1, US 2012-0192300A1, US 2013-0045492A1, US 2013-0185821A1 and US 2013-0302836A1; which applications are herein incorporated by reference in their entireties).

The term "replacement" is used herein to include a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a variable domain, and the DNA fragment encodes one or more human variable domains). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "small molecule" includes an organic compound whose molecular weight, in the absence of a carrier, is less than about 6 kilodaltons (kD) in size, and that can be extracted from natural sources or produced synthetically (xenobiotic). "Small molecules" may also comprise organic compounds that further comprise inorganic atoms, e.g., complexed metals. "Small molecule" may refer to a hapten, e.g., a molecule that may bind antigen-binding proteins in traditional immunoglobulin format but cannot elicit an adaptive immune response. In some embodiments, the small molecule, in absence of a carrier, is less than about 5 kD, 4 kD, 3 kD, about 2 kD, or about 1 kD. In some embodiments, the molecular weight of the small molecule, in the absence of a carrier, as described herein ranges from 1 kD to 6 kD. In some embodiments, the molecular weight of the small molecule, in absence of a carrier, is less than 1.5 kD. In some certain embodiments, the molecular weight of the small molecule, in the absence of a carrier, as described herein is less than 1400 daltons (D), less than 1300 D, less than 1200 D, less than 1100 D, less than 1000 D, less than 900 D, less than 800 D, less than 700 D, less than 600 D, less than 500 D, less than 400 D, less than 300 D, less than 200 D, or less than 100 D. In some embodiments, the small molecule, in the absence of a carrier, is less than about 800 daltons (D), about 600 D, about 500 D, about 400 D, about 300 D, about 200 D, or about 100 D. In some embodiments, a small molecule, in the absence of a carrier, is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic).

The phrase "somatically hypermutated" includes reference to a nucleic acid sequence or amino acid sequence encoded by the somatically nucleic acid sequence, from a B cell that has undergone class-switching wherein the nucleic acid sequence of an immunoglobulin variable region (e.g., nucleotide sequence encoding a light chain variable domain or including a light chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" or includes reference to nucleic acid sequences or amino acid sequences encoded thereby from affinity-matured B cells that are not identical to corresponding immunoglobulin variable region sequences in B cells that are not affinity-matured (i.e., sequences in the genome of germ line cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" includes sequences from immunoglobulins that have been generated in an animal, e.g., a mouse having human immunoglobulin variable region nucleic acid sequences, in response to an antigen challenge, and that result from the selection processes inherently operative in such an animal.

The term "substantially" includes the qualitative condition of exhibiting total or near-total extent or degree of a characteristic or property of interest One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et aL, Bioinformatics: A Practical Guide to the Analysis of Genes and Proteins, Wiley, 1998; and Misener, et aL, (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

TABLE 1

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

The phrase "substantial identity" includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "unrearranged," with reference to a nucleic acid sequence, includes nucleic acid sequences that exist in the germ line of an animal cell. Generally, during B cell development in unmodified non-human animals, the first rearrangement of unrearranged gene segments is the joining of $D_H$ and $J_H$ gene segments in a heavy chain locus, generating a pro-B cell. Subsequent rearrangements include $V_H$-$D_H J_H$ joining in a heavy chain locus, and if productive, rearrangement of light chain variable region gene segments, e.g., joining of a VL gene segment with a JL gene segment within a light chain locus. A rearrangement is considered "productive" if the joining is in frame ("productive"). Productive rearrangement at one allele may result in allelic exclusion, e.g., the silencing of the other allele. "Unrearranged" also refers to unrearranged $V_L$ and $J_L$ gene segments capable of undergoing productive rearrangement to form a light chain variable region gene operably linked to a heavy chain constant region gene segment, such operable linkage resulting in a gene encoding a hybrid immunoglobulin chain, which may also result in the allelic exclusion of one or more endogenous heavy chain alleles and/or the rearrangement of light chain variable region gene segments at one or more endogenous light chain loci.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

The term "variant" includes an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector" includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type" has its art-understood meaning that includes an entity having a structure and/or activity as found in nature in a "normal" (as contrasted with mutant, diseased, altered, etc.) state or context Those of ordinary skill in the art will appreciate that wild type genes and polypeptides often exist in multiple different forms (e.g., alleles).

DETAILED DESCRIPTION OF CERTAIN EMBODIMENTS

The present invention provides, among other things, methods of using genetically engineered non-human animals having human genetic material encoding light chain variable domains (e.g., $V_L$ regions). In certain embodiments, such non-human animals are useful, for example, for the production and isolation of human $V_L$ domains, and the complementarity determining regions (CDRs) comprised in such human $V_L$ domains, that bind antigenic determinants that evade traditional immunoglobulin formats. It is contemplated that such non-human animals provide a novel in vivo system for the generation and affinity maturation of human $V_L$ domains that exhibit unique antigen-binding characteristics. Such antigen-binding proteins have the capacity to recognize foreign antigens that may elude natural immunoglobulins. In some embodiments, non-human animals of the present invention are capable of generating cognate human $V_L$ domains that bind to antigen as compared to control genetically modified non-human animals; in some embodiments, such non-human mammals develop and/or have a B cell population that express binding proteins resemble immunoglobulins in structure yet are devoid of any heavy chain variable sequences. In some embodiments, antigen-binding proteins expressed by such non-human animals are characterized in that the antigen-binding portion comprises exclusively of human $V_L$ domains. In some embodiments, the non-human animals of the present invention comprise an endogenous immunoglobulin heavy chain locus that contains genetic material from the non-human animal and a heterologous species (e.g., a human) and comprise an endogenous immunoglobulin light chain locus that contains genetic material from the non-human animal and a heterologous species (e.g., human). In some embodiments, non-human animals of the present invention comprise an immunoglobulin heavy chain locus that includes unrearranged human $V_L$ and $J_L$ gene segments and an immunoglobulin light chain locus that includes unrearranged human $V_L$ and $J_L$ gene segments. In some embodiments, the expression of the antigen-binding proteins is under the control of non-human immunoglobulin genetic material (e.g., a non-human immunoglobulin promoter and/or enhancer).

Various aspects of the invention are described in detail in the following sections. The use of sections is not meant to limit the invention. Each section can apply to any aspect of the invention.

Immunoglobulin-Like Binding Proteins Specific for Small Molecules

In one aspect, a $V_L$ antigen-binding protein that specifically binds a small molecule is provided. $V_L$ antigen binding protein aspects described herein include $V_L$ antigen binding proteins that comprise a hybrid chain encoded by a hybrid immunoglobulin gene comprising or derived from a, preferably unrearranged and more preferably human, $V_L$ gene segment (or portion thereof) rearranged with a, preferably unrearranged and more preferably human, $J_L$ gene segment (or portion thereof) operably linked to nucleotide sequences that encode one or more heavy chain constant domains. Upon rearrangement of the light chain gene segments, a rearranged nucleotide sequence is obtained that comprises a sequence encoding a light chain variable region fused with a sequence encoding a heavy chain constant region. This sequence encodes a hybrid immunoglobulin chain that has a light chain variable domain fused with a heavy chain constant domain. Thus, in one embodiment, the hybrid immunoglobulin consists essentially of, from N-terminal to C-terminal, a $V_L$ domain and a $C_H$ domain. In one embodiment, the $C_H$ domain comprises a $C_H1$ region, a hinge, a $C_H2$ region, a $C_H3$ region, and optionally a $C_H4$ region. In another embodiment, the $CH_L$ domain lacks a functional $C_H1$ domain, e.g., lacks a $C_H1$ domain in whole or in part, and may additionally lack a hinge region.

In some embodiments, the $V_L$ antigen binding protein comprises a hybrid immunoglobulin chain comprising an immunoglobulin light chain variable domain that specifically binds to a small molecule, wherein the immunoglobulin light chain variable domain is operably linked to a heavy chain constant region. In some embodiments, the $V_L$ antigen binding protein comprises first and second immunoglobulin light chain variable domains, wherein the first and the second immunoglobulin light chain variable domains may associate to form a binding pocket that specifically binds a small molecule. In one aspect, an antigen-binding protein is provided consisting essentially of first and second immunoglobulin light chain variable domains that are associated to form a binding pocket, wherein the antigen-binding protein specifically binds a small molecule.

In one embodiment, the first and/or the second immunoglobulin light chain variable domain is a human immunoglobulin light chain variable domain. In one embodiment, the first and/or the second immunoglobulin light chain domain is from a rodent. In one embodiment, the rodent is selected from a mouse or a rat.

In various embodiments, $V_L$ antigen binding proteins as disclosed herein, e.g., those produced by the genetically modified non-human animals, e.g., mice, disclosed herein, may be on average smaller than conventional antibodies, and possess advantages associated with smaller size. Smaller size is realized at least in part through the absence of an amino acid sequence encoded by a $D_H$ region, normally present in a $V_H$ domain. Smaller size can also be realized in the formation of a CDR3 that is derived, e.g., from a Vκ region and a Jκ region.

In one embodiment, the light chain variable domains binds the small molecule with higher affinity than a binding pocket of a human antigen-binding protein that is formed from human immunoglobulin light and heavy chain variable domains.

In one embodiment, the first and/or the second immunoglobulin light chain variable domains are human light chain variable domains. In one embodiment, the binding pocket of the light chain variable domains binds the small molecule with higher affinity than a binding pocket of a human antibody that is formed from human immunoglobulin light and heavy chain variable domains.

In one embodiment, the first light chain variable domain is linked to a first immunoglobulin heavy chain constant region. In one embodiment, the first immunoglobulin heavy chain constant region is from a non-human animal. In one embodiment, the non-human animal is a rodent. In one embodiment, the rodent is selected from a mouse or a rat. In one embodiment, the non-human animal is a chicken. In one embodiment, the first immunoglobulin heavy chain constant region is selected from a CH1, a hinge, a CH2, a CH3, a CH4, and a combination thereof. In one embodiment, the first immunoglobulin heavy chain constant region comprises a CH1, a hinge, a CH2, and a CH3.

In one embodiment, the second immunoglobulin light chain variable domain is linked to a second immunoglobulin light chain constant region. In one embodiment, the second immunoglobulin light chain constant region is from a non-human animal. In one embodiment, the non-human animal is a rodent. In one embodiment, the rodent is selected from a mouse or a rat. In one embodiment, the non-human animal is a chicken.

In one embodiment, the $V_L$ antigen binding protein comprises two identical light chain variable domains. In one embodiment, the $V_L$ antigen binding protein comprises two light chain variable domains with heterogeneous sequences.

A $V_L$ antigen binding protein that binds a small molecule may be obtained from a genetically modified non-human animal as disclosed herein or derived from cells and/or nucleic acids isolated from such an animal after immunization with the small moleucle.

Genetically Modified Non-Human Animals That Express $V_L$ Proteins

Non-human animals that express $V_L$ antigen binding proteins that comprise hybrid immunoglobulin chains having a heavy chain constant domain fused with an immunoglobulin light chain variable domain are provided. Further, multiple strategies are provided to genetically modify an non-human animal, e.g., a rodent, which includes but is not limited to rats and mice, to express a hybrid chain as part of a $V_L$ antigen binding protein, wherein the hybrid chain is encoded by or derived from an nucleic acid encoding a $V_L$ region operably linked to a nucleotide sequence encoding a $C_H$ region. Such genetically modified non-human animals represent a source for generating populations of $V_L$ antigen binding proteins that have the tetrameric structure of some conventional antibodies, yet exhibit a unique binding characteristic compared to traditional antibodies.

The modified non-human animals described herein may generate $V_L$ antigen binding proteins that also comprise a cognate light chain paired with a hybrid chain to make a $V_L$ antigen binding protein that is antibody-like, e.g., may be tetrameric, but wherein instead of a heavy chain (or pair of heavy chains) the $V_L$ antigen binding protein comprises a hybrid chain (or pair of hybrid chains) that comprises $V_L$ domain—not a $V_H$ domain—fused to a $C_H$ domain.

In various embodiments, the modified non-human animals make $V_L$ antigen binding proteins, wherein the $V_L$ domain of a hybrid chain exhibits an enhanced degree of somatic hypermutation over a $V_L$ domain of a light chain. In some embodiments, a $V_L$ region of a hybrid chain exhibits about 1.5-fold, 2-fold, 2.5-fold, 3-fold, 3.5-fold, 4-fold, 4.5-fold, or 5-fold or more somatic hypermutations than a $V_L$ region fused with a $C_L$ region. In some embodiments, the modified non-human animal, e.g., mouse, in response to an antigen exhibits a population of antigen binding proteins that comprise a $V_L$ domain of a hybrid chain, wherein the population of $V_L$ antigen binding proteins exhibits an average of about 1.5-fold, 2-fold, 2.5-fold, 3-fold, 3.5-fold, 4-fold, 4.5-fold, 5-fold or more somatic hypermutations in the $V_L$ domain of the hybrid chain than is observed in a population of antigen binding proteins, e.g., a $V_L$ domain of a light chain, exhibited by a wild-type mouse in response to the same antigen.

In one embodiment, the somatic hypermutations in the $V_L$ domain of the hybrid chain comprises one or more or two or more N additions in a CDR3. In various embodiments, the $V_L$ antigen binding proteins comprise hybrid chains comprising variable domains encoded by immunoglobulin light chain sequences that comprise a larger number of N additions than observed in nature for light chains rearranged from an endogenous light chain locus, e.g., the $V_L$ and human $J_L$ gene segments rearrange to form a rearranged variable region gene operably linked with a heavy chain constant region gene, wherein the rearranged light chain variable region comprises 1, 2, 3, 4, 5, 6, 7, 8, 9, 10, 11, 12, 13, 14, 15, 16 or more N additions.

In one aspect, a non-human animal, e.g., a mouse, is provided, comprising an immunoglobulin hybrid chain locus. In one embodiment, the hybrid chain locus is created within an endogenous heavy chain locus, wherein one or more immunoglobulin heavy chain variable region ($V_H$) gene segments, heavy chain diversity ($D_H$) gene segments, and heavy chain joining ($J_H$) gene segments at an endogenous mouse immunoglobulin heavy chain locus are replaced with one or more light chain variable region ($V_L$) gene segments and one or more light chain joining region ($J_L$) gene segments. In one aspect, a non-human animal is provided, comprising a hybrid chain locus that replaces the endogenous immunoglobulin heavy chain locus, e.g., all or substantially all endogenous $V_H$, $D_H$, and $J_H$ gene segments of one or both heavy chain loci are replaced with one or more $V_L$ gene segments and one or more $J_L$ gene segments that form a rearranged $V_L$ gene sequence at an endogenous heavy chain locus capable of recombining with an endogenous mouse $C_H$ gene to form a rearranged gene that is derived from a $V_L$ gene segment, a $J_L$ gene segment, and an endogenous mouse $C_H$ gene.

The non-human animals also encompasses the humanization of immunoglobulin loci resulting in expression of binding proteins, e.g., $V_L$ antigen binding proteins, that resemble some conventional antibodies' tetrameric structure yet differ in binding characteristics, and resulting in expression of said $V_L$ antigen binding proteins on the membrane surface of cells of the non-human animal. In some embodiments, non-human animals of the present invention are capable of generating human $V_L$ domains, on either or both the hybrid and light chains of the $V_L$ antigen binding protein, that bind to antigen; in some embodiments, such non-human mammals develop and/or have a B cell population that express binding proteins comprising variable domains that are not encoded by or derived from any $V_H$, $D_H$ and/or $J_n$ gene segment sequences. In some embodiments, $V_L$ antigen binding proteins expressed by such non-human animals are characterized in that the antigen-binding portion is comprises exclusively of human $V_L$ domains. In some embodiments, non-human animals of the present invention comprise at an endogenous immunoglobulin heavy chain locus genetic material from the non-human animal and a heterologous species (e.g., a human) and comprise at an endogenous immunoglobulin light chain locus genetic material from the non-human animal and a heterologous species (e.g., human).

In some embodiments, non-human animals of the present invention comprise an immunoglobulin hybrid chain locus that includes unrearranged human $V_L$ gene segments and/or human $J_L$ gene segments and, preferably, an immunoglobulin light chain locus that includes unrearranged human $V_L$ gene segments and/or human $J_L$ gene segments. In some embodiments, the expression of the $V_L$ antigen binding proteins is under the control of non-human immunoglobulin genetic material (e.g., a non-human immunoglobulin promoter and/or enhancer).

In one embodiment, the $V_L$ segments are human $V_L$. In one embodiment, the $J_L$ segments are human $J_L$. In a specific embodiment, the $V_L$ and $J_L$ segments are human $V_L$ and human $J_L$ segments.

In one embodiment, all or substantially all $V_H$, $D_H$, and $J_n$ gene segments are replaced with at least six human Vκ gene segments and at least one Jκ gene segment. In one embodiment, all or substantially all $V_H$, $D_H$, and $J_H$ gene segments are replaced with at least 16 human Vκ gene segments (human Vκ) and at least one Jκ gene segment. In one embodiment, all or substantially all $V_H$, $D_H$, and $J_H$ gene segments are replaced with at least 30 human Vκ gene segments and at least one Jκ gene segment. In one embodiment, all or substantially all $V_H$, $D_H$, and $J_H$ gene segments are replaced with at least 40 human Vκ gene segments and at least one Jκ gene segment. In one embodiment, the at least one Jκ gene segment comprises two, three, four, or five human Jκ gene segments.

In one embodiment, the $V_L$ segments are human Vκ segments. In one embodiment, the human Vκ segments comprise 4-1, 5-2, 7-3, 2-4, 1-5, and 1-6. In one embodiment, the Vκ segments comprise 3-7, 1-8, 1-9, 2-10, 3-11, 1-12, 1-13, 2-14, 3-15, 1-16. In one embodiment, the human Vκ segments comprise 1-17, 2-18, 2-19, 3-20, 6-21, 1-22, 1-23, 2-24, 3-25, 2-26, 1-27, 2-28, 2-29, and 2-30. In one embodiment, the human Vκ segments comprise 3-31, 1-32, 1-33, 3-34, 1-35, 2-36, 1-37, 2-38, 1-39, and 2-40.

In one embodiment, the $V_L$ segments are human Vκ segments and comprise 4-1, 5-2, 7-3, 2-4, 1-5, 1-6, 3-7, 1-8, 1-9, 2-10, 3-11, 1-12, 1-13, 2-14, 3-15, and 1-16. In one embodiment, the Vκ segments further comprise 1-17, 2-18, 2-19, 3-20, 6-21, 1-22, 1-23, 2-24, 3-25, 2-26, 1-27, 2-28, 2-29, and 2-30. In one embodiment, the Vκ segments further comprise 3-31, 1-32, 1-33, 3-34, 1-35, 2-36, 1-37, 2-38, 1-39, and 2-40.

In one embodiment, the $V_L$ segments are human Vλ segments and comprise a fragment of cluster A of the human λ light chain locus. In a specific embodiment, the fragment of cluster A of the human λ light chain locus extends from hVλ3-27 through hVλ3-1.

In one embodiment, the $V_L$ segments comprise a fragment of cluster B of the human λ light chain locus. In a specific embodiment, the fragment of cluster B of the human λ light chain locus extends from hVλ5-52 through hVλ1-40.

In one embodiment, the $V_L$ segments comprise a human λ light chain variable region sequence that comprises a genomic fragment of cluster A and a genomic fragment of cluster B. In a one embodiment, the human λ light chain variable region sequence comprises at least one gene segment of cluster A and at least one gene segment of cluster B.

In one embodiment, the $V_L$ segments comprise at least one gene segment of cluster B and at least one gene segment of cluster C.

In one embodiment, the $V_L$ segments comprise hVλ3-1, 4-3, 2-8, 3-9, 3-10, 2-11, and 3-12. In a specific embodiment, the $V_L$ segments comprise a contiguous sequence of the human λ light chain locus that spans from Vλ3-12 to Vλ3-1. In one embodiment, the contiguous sequence comprises at least 2, 3, 4, 5, 6, 7, 8, 9, 10, 11 or 12 hVλs. In a specific embodiment, the hVλs include 3-1, 4-3, 2-8, 3-9, 3-10, 2-11, and 3-12. In a specific embodiment, the hVλs comprises a contiguous sequence of the human λ locus that spans from Vλ3-12 to Vλ3-1.

In one embodiment, the hVλs comprises 13 to 28 or more hVλs. In a specific embodiment, the hVλs include 2-14, 3-16, 2-18, 3-19, 3-21, 3-22, 2-23, 3-25, and 3-27. In a specific embodiment, the hVλs comprise a contiguous sequence of the human λ locus that spans from Vλ3-27 to Vλ3-1.

In one embodiment, the $V_L$ segments comprise 29 to 40 hVλs. In a specific embodiment, the $V_L$ segments comprise a contiguous sequence of the human λ locus that spans from Vλ3-29 to Vλ3-1, and a contiguous sequence of the human λ locus that spans from Vλ5-52 to Vλ1-40. In a specific embodiment, all or substantially all sequence between hVλ1-40 and hVλ3-29 in the genetically modified mouse consists essentially of a human λ sequence of approximately 959 bp found in nature (e.g., in the human population) downstream of the hVλ1-40 gene segment (downstream of the 3' untranslated portion), a restriction enzyme site (e.g., PI-SceI), followed by a human λ sequence of approximately 3,431 bp upstream of the hVλ3-29 gene segment found in nature.

In one embodiment, the Jκ is human and is selected from the group consisting of Jκ1, Jκ2, Jκ3, Jκ4, Jκ5, and a combination thereof. In a specific embodiment, the Jκ comprises Jκ1 through Jκ5.

In one embodiment, the $V_L$ segments are human Vλ segments, and the Jκ gene segment comprises an RSS having a 12-mer spacer, wherein the RSS is juxtaposed at the upstream end of the Jκ gene segment. In one embodiment, the $V_L$ gene segments are human Vλ and the $VL_H$ locus comprises two or more Jκ gene segments, each comprising an RSS having a 12-mer spacer wherein the RSS is juxtaposed at the upstream end of each Jκ gene segment.

In a specific embodiment, the $V_L$ segments comprise contiguous human κ gene segments spanning the human κ locus from Vκ4-1 through Vκ2-40, and the $J_L$ segments comprise contiguous gene segments spanning the human κ locus from Jκ1 through Jκ5.

In one embodiment, where the $V_L$ segments are Vλ segments and no $D_H$ segment is present between the $V_L$ segments and J segments, the $V_L$ segments are flanked downstream (i.e., juxtaposed on the downstream side) with 23-mer RSS, and Jκ segments if present or Jλ segments if present are flanked upstream (i.e., juxtaposed on the upstream side) with 12-mer RSS.

In one embodiment, where the V gene segments are Vκ gene segments and no $D_H$ gene segment is present between the V gene segments and J gene segments, the Vκ gene segments are each juxtaposed on the downstream side with a 12-mer RSS, and Jκ segments if present or Jλ segments if present are each juxtaposed on the upstream side with a 23-mer RSS.

In one aspect, a cell is provided, comprising a modified immunoglobulin locus as described herein. In one embodiment, the cell is selected from a totipotent cell, a pluripotent cell, an induced pluripotent stem cell (iPS), and an ES cell. In one embodiment, the ES cell is an F1 ES line (F1H4; Valenzuela et al. 2007, supra) derived from 12956/SvEvTac and C57BL/6NTac heterozygous embryos that further contained an in situ replacement of the mouse κ light chain gene segments with human κ light chain gene segments (e.g., see U.S. Pat. Nos. 6,596,541 and 8,642,835, incorporated herein by reference in their entireties). In one embodiment, the genetic modification is carried out in a hybrid ES cell line whose genome comprises 50% BALB/c[Tac], 25% C57BL/6N[Tac], and 25% 12954/SvJae(V17).

In a specific embodiment, the cell is a mouse cell, e.g., a mouse ES cell. In one embodiment, the cell is homozygous for the modified immunoglobulin locus. In one embodiment, the cell is a rat cell, e.g., a rat ES cell (see, US-2014-0310828-A1, incorporated by reference herein in its entirety).

Small Molecules

In one embodiment, the small molecule is a hapten, and the small molecule is linked to a carrier. In one embodiment, the carrier comprises keyhole limpet hemocyanin (KLH), Concholepas concholepas hemocyanin (CCH), bovine serum albumin (BSA), a cationized bovine serum albumin (cBSA), or ovalbumin. In one embodiment, the small molecule is an organic compound whose molecular weight is less than 6 kDa.

In some embodiments, the small molecule is a hapten in that it elicits an immune response only when attached to a large carrier but does not produce a useful or significant immune response when under otherwise comparable conditions lacking the carrier or other adjuvant, e.g., employed as an immunogen alone in the absence of an adjuvant. Examples of haptens include, but are not limited to, antibiotics, pesticides, herbicides, insecticides, drugs, vitamins, steroids, hormones, toxins, explosives, and dyes (see, for example, Gunther, S. et al., SuperHapten: a comprehensive database for small immunogenic compounds, Nucleic Acids Res., 2007, D906-910, which is incorporated by reference herein in its entirety). A comprehensive list of haptens and corresponding hapten-carrier conjugates also can be found in Hapten Database (Singh, M. et al., Bioinformatics, 2006, 22:253-255), which is accessible via the internet on the world wide web (www) at the URL "imtech.res.in/raghava/haptendb/."

In some embodiments, the carrier is a macromolecule that binds a hapten and enables it to induce an immune response. In some embodiments, the carrier is a secretory protein or a cell surface protein. In some embodiments, the carrier is a polymer. In some embodiments, the carrier is keyhole limpet hemocyanin (KLH). In some embodiments, the carrier is purified preparation of Concholepas concholepas hemocyanin (CCH). In some embodiments, the carrier is bovine serum albumin (BSA). In some embodiments, the carrier is a cationized BSA (cBSA) that is prepared by modifying native BSA with excess ethyenediamine, essentially capping negatively-charged carboxyl groups with positively charged primary amines. In some embodiments, the carrier is ovalbumin.

In some embodiments, the small molecule is a natural steroid. In some embodiments, the small molecule is a steroid characterized by a molecular structure of 17 carbon atoms arranged in four rings. Examples of the steroid as described herein include, but are not limited to, hormones and alkaloids.

In some embodiments, the steroid is a cardiotonic steroid (CTS). In some embodiments, the CTS is an inhibitor of Na+/K+-ATPase. Examples of the CTS include, but are not limited to, cardenolide (endogenous ouabain), bufadienolides, bufalin, marinobufagenin (MBG), and telocinobufagin. In some embodiments, the hapten is marinobufagenin (MBG) and the carrier is bovine serum albumin. In some embodiments, the steroid is cortisol.

In some embodiments, the small molecule is a poison or poisonous substance, including, but not limited to, parathion, malathion, tetraethylpyrophosphate (TEPP), 4,6-dinitro-o-cresol (DNOC), metacide, demeton (systex), chlordane, toxaphene, aldrin, benzene hexachloride, lindane, dieldrin, rotenone, pestex, dichlorodiphenyltrichloroethane (DDT), a selenium compound (silocide), zinc phosphide (Zn3P2), a strychnine compound, warfarin, and arsenic trioxide.

In some embodiments, the small molecule is a psychoactive drug or psychotropic substance that crosses the blood-brain barrier and acts on the central nervous system where it affects brain function, resulting in changes in perception, mood, consciousness, cognition, and behavior. In some embodiments, the small molecule is a stimulant, including, but not limited to, caffeine, nicotine, amphetamines, and cocaine. In some embodiments, the small molecule is an opioid alkaloid, including, but not limited to, morphine, codeine, heroin, fentanyl, methadone, and oxycodone. In some embodiments, the small molecule is a psychedelic drug that distorts sensory perceptions, including sight and sound. Examples of the psychedelic drug include, but are not limited to mesacaline, psilocybin, dimethyltryptamine (DMT), lysergic acid diethylamide (LSD), dimethoxymethylamphetamine (DOM or "STP"), methylenedioxymethamphetamine (MDMA or "ecstasy").

In some embodiments, the small molecule is a neurotransmitter, including, but not limited to, acetylcholine, norepinephrin, epinephrine, dopamine, serotonin, glutamate, glycine, and gamma-aminobutiric acid (GABA).

In some embodiments, the small molecule includes, but is not limited to, forskolin, solamarigine, crocin, marihuana compounds, opium alkaloids, ginsenosides, berberine, sennosides, paeoniflorin, glycyrrhizin, ginkgolic acid, aconitine alkaloid, and baicalin.

Nucleic Acid Constructs, Cells and Methods of Making the Same

In one aspect, provided are a nucleic acid encoding a variable domain of a $V_L$ binding domain that specifically binds a small molecule, and a cell expressing the nucleic acid.

In one aspect, use of a nucleic acid sequence from a mouse as described herein to make a cell line for the manufacture of a human therapeutic is provided. In one embodiment, the human therapeutic is a binding protein comprising a human light chain variable sequence (e.g., derived from a human Vλ or human Vκ segment) fused with a human heavy chain constant sequence. In one embodiment, the human therapeutic comprises a first polypeptide that is a human λ or κ immunoglobulin light chain, and a second polypeptide that comprises a human Vλ or human Vκ variable sequence fused with a human heavy chain constant sequence.

In one aspect, an expression system is provided, comprising a mammalian cell comprising a nucleic acid that encodes a polypeptide that comprises a somatically mutated human $V_L$ domain fused with a human $C_H$ domain.

In one embodiment, the expression system further comprises a nucleotide sequence that encodes an immunoglobulin $V_L$ domain fused with a human $C_L$ domain, wherein the $V_L$ domain fused with the human $C_L$ domain is a cognate light chain with the $V_L$ domain fused with the human $C_H$ domain.

In one embodiment, the suitable cell is selected from a B cell, a hybridoma, a quadroma, a CHO cell, a COS cell, a 293 cell, a HeLa cell, and a human retinal cell expressing a viral nucleic acid sequence (e.g., a PERC.6™ cell).

In one aspect, a method for making a binding protein is provided, isolating a cell or nucleic acid from a non-human animal as disclosed herein, wherein the cell or nucleic acid comprises or encodes a $V_L$ binding protein that binds a small molecule. In some embodiments, the method further comprises and cloning the nucleotide sequence encoding the $V_L$ region sequence in frame with a gene encoding a human $C_H$ region to form a human binding protein sequence, expressing the human binding protein sequence in a suitable cell.

In one embodiment, the non-human has been immunized with a small molecule or a small molecule linked to a carrier, and the $V_L$ region fused to the $C_H$ region specifically binds (e.g., with a $K_D$ in the micromolar, nanomolar, or picomolar range) an epitope of the small molecule. In one embodiment, nucleotide sequence encoding the $V_L$ region fused to the $C_H$ region is somatically mutated in the mouse.

In one aspect, a method for making an antigen-binding protein that binds a small molecule is provided, the method comprising (a) immunizing a non-human animal with a small molecule or the small molecule linked to a carrier, wherein the non-human animal comprises in its germline (i) unrearranged human immunoglobulin light chain variable (VL) and light chain joining (JL) gene segments operably linked to a non-human heavy chain constant region nucleic acid sequence, and (ii) unrearranged human immunoglobulin light chain variable (VL) and light chain joining (JL) gene segments operably linked to a non-human light chain constant region nucleic acid sequence; (b) allowing the non-human animal to mount an immune response to the small molecule or the small molecule linked to the carrier; (c) isolating a cell (e.g., a lymphocyte) from the immunized non-human animal, wherein the cell comprises first and second immunoglobulin variable region nucleic acid sequences that encode first and second immunoglobulin light chain variable domains; (d) identifying the first and the second immunoglobulin light chain variable region nucleic acid sequences that encode first and second immunoglobulin light chain variable domains that, when paired, specifically bind the small molecule or the small molecule linked to the carrier; and, (e) expressing the nucleic acid sequences of (d) in an expression system suitable for expressing the antigen-binding protein so as to form an antigen-binding protein comprising a dimer of the first and the second light chain variable domains that bind the small molecule.

In some embodiments, cells (such as B-cells) are recovered from the animal (e.g., from spleen or lymph nodes). The cells may be fused with a myeloma cell line to prepare immortal hybridoma cell lines, and such hybridoma cell lines are screened and selected to identify hybridoma cell lines that produce antibodies containing hybrid heavy chains specific to the antigen used for immunization.

In one embodiment, immunization comprises priming the mouse with the small molecule or a small molecule linked to a carrier, allowing the non-human animal to rest for a period of time, and re-immunizing the animal with the small molecule or a small molecule linked to a carrier. In some embodiments, the period of time is a few days, at least a week, at least two weeks, at least three weeks, at least four weeks, or at least one month.

In one aspect, an immunoglobulin variable region (VR) (e.g., comprising a human $V_L$ sequence fused with a human $J_L$) made in a mouse as described herein is provided. In a specific embodiment, the immunoglobulin VR is derived from a germline human gene segment selected from a Vκ segment and a Vλ segment, wherein the VR is encoded by a rearranged sequence from the mouse wherein the rearranged sequence is somatically hypermutated. In one embodiment, the rearranged sequence comprises 1 to 5 somatic hypermutations. In one embodiment, the rearranged sequence comprises at least 6, 7, 8, 9, or 10 somatic hypermutations. In one embodiment, the rearranged sequence comprises more than 10 somatic hypermutations. In one embodiment, the rearranged sequence is fused with one or more human or mouse heavy chain constant region sequences (e.g., selected from a human or mouse $C_H1$, hinge, CH2, $C_H3$, and a combination thereof).

In one aspect, an immunoglobulin variable domain amino acid sequence of a binding protein made in a mouse as described herein is provided. In one embodiment, the VR is fused with one or more human or mouse heavy chain constant region sequences (e.g., selected from a human or mouse $C_H1$, hinge, $C_H2$, $C_H3$, and a combination thereof).

In one aspect, a light chain variable domain encoded by a nucleic acid sequence derived from a mouse as described herein is provided.

In one aspect, a binding protein or antigen-binding fragment thereof (e.g., Fab, F(ab)$_2$, scFv) made in a mouse as described herein, or derived from a sequence made in a mouse as described herein, is provided.

Bispecific-Binding Proteins

Immunoglobulin-like binding proteins comprising an immunoglobulin heavy chain constant region fused with an immunoglobulin light chain variable domain are provided, as well as binding proteins having an immunoglobulin light chain variable domain fused to a light chain constant domain and an immunoglobulin light chain variable domain fused to a heavy chain constant domain. Cells expressing such binding proteins, mice that make them, and related methods and compositions are also provided.

The binding proteins described herein, and nucleotide sequences encoding them, can be used to make multispecific binding proteins, e.g., bispecific binding proteins. In this aspect, a first polypeptide consisting essentially of a first $V_L$ domain fused with a $C_H$ region can associate with a second polypeptide consisting essentially of a second $V_L$ domain fused with a $C_H$ region. Where the first $V_L$ domain and the second $V_L$ domain specifically bind a different epitope, a bispecific-binding molecule can be made using the two $V_L$ domains. The $C_H$ region can be the same or different. In one embodiment, e.g., one of the $C_H$ regions can be modified so as to eliminate a protein A binding determinant, whereas the other heavy chain constant region is not so modified (see U.S. Pat. No. 8,586,713 B2, which is incorporated by reference herein in its entirety). This particular arrangement simplifies isolation of the bispecific binding protein from, e.g., a mixture of homodimers (e.g., homodimers of the first or the second polypeptides).

In one aspect, nucleic acids constructs, cells, embryos, mice, and methods are provided for making proteins that comprise one or more κ and/or λ light chain variable region immunoglobulin sequences and an immunoglobulin heavy chain constant region sequence, including proteins that comprise a human λ or κ light chain variable domain and a human or mouse heavy chain constant region sequence.

In one aspect, binding proteins are described that comprise immunoglobulin variable domains that are derived from light chain (i.e., kappa (κ) and/or lambda (λ)) immunoglobulin variable domains, but not from full-length heavy chain immunoglobulin variable domains. Methods and compositions for making binding proteins, including genetically modified mice, are also provided.

In one aspect, the methods and compositions described herein are used to make bispecific-binding proteins. In this aspect, a first $V_L$ that is fused to a $C_H$ region and a second $V_L$ that is fused to a $C_H$ region are each independently cloned in frame with a human IgG sequence of the same isotype (e.g., a human IgG1, IgG2, IgG3, or IgG4). The first $V_L$ specifically binds a first epitope, and the second $V_L$ specifically binds a second epitope. The first and second epitopes may be on different antigens, or on the same antigen.

In one embodiment, the IgG isotype of the CH region fused to the first $V_L$ and the IgG isotype of the CH region fused to the second $V_L$ are the same isotype, but differ in that one IgG isotype comprises at least one amino acid substitution. In one embodiment, the at least one amino acid substitution renders the heavy chain bearing the substitution unable or substantially unable to bind protein A as compared with the heavy chain that lacks the substitution.

In one embodiment, the first CH region comprises a first $C_H3$ domain of a human IgG selected from IgG1, IgG2, and IgG4; and the second CH region comprises a second $C_H3$ domain of a human IgG selected from IgG1, IgG2, and IgG4, wherein the second $C_H3$ domain comprises a modification that reduces or eliminates binding of the second $C_H3$ domain to protein A (see U.S. Pat. No. 8,586,713 B2, which is incorporated by reference in its entirety).

In one embodiment, the second $C_H3$ domain comprises a 435R modification, numbered according to the EU numbering system. In another embodiment, the second $C_H3$ domain further comprises a 436F modification, numbered according to the EU numbering system.

In one embodiment, the second $C_H3$ domain is that of a human IgG1 that comprises a modification selected from the group consisting of D356E, L358M, N384S, K392N, V397M, and V422I, numbered according to the EU numbering system.

In one embodiment, the second $C_H3$ domain is that of a human IgG2 that comprises a modification selected from the group consisting of N384S, K392N, and V422I, numbered according to the EU numbering system.

In one embodiment, the second $C_H3$ domain is that of a human IgG4 comprising a modification selected from the group consisting of Q355R, N384S, K392N, V397M, R409K, E419Q, and V422I, numbered according to the EU numbering system.

In one embodiment, the binding protein comprises $C_H$ regions having one or more modifications as recited herein, wherein the constant region of the binding protein is nonimmunogenic or substantially nonimmunogenic in a human. In a specific embodiment, the $C_H$ regions comprise amino acid sequences that do not present an immunogenic epitope in a human. In another specific embodiment, the binding protein comprises a $C_H$ region that is not found in a wild-type human heavy chain, and the $C_H$ region does not comprise a sequence that generates a T-cell epitope.

In one embodiment, Fc domains can be modified to have altered Fc receptor binding, which in turn affects effector function. An engineered heavy chain constant region ($C_H$), which includes the Fc domain, may be chimeric. As such, a chimeric $C_H$ region combines $C_H$ domains derived from more than one immunoglobulin isotype. For example, a chimeric $C_H$ region comprises part or all of a $C_H2$ domain derived from a human IgG1, human IgG2 or human IgG4 molecule, combined with part or all of a $C_H3$ domain derived from a human IgG1, human IgG2 or human IgG4 molecule. A chimeric CH region can also contain a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. In one embodiment, the chimeric hinge region comprises amino acid residues derived from a human IgG1 or a human IgG4 upper hinge and amino acid residues derived from a human IgG2 lower hinge.

For certain therapies, the Fc domain may be engineered to activate all, some, or none of the normal Fc effector functions, without affecting the Fc-containing protein's (e.g. antibody's) desired pharmacokinetic properties. For examples of proteins comprising chimeric $C_H$ regions and having altered effector functions, see U.S. application Ser. No. 14/170,166, filed Jan. 31, 2014, which is incorporated herein in its entirety.

Profiling Binding Characteristics, Binning, and Related Methodologies

Disclosed herein is the unexpected finding that a $V_L$ antigen binding protein, particularly if generated in non-human animals comprising a hybrid immunoglobulin gene as disclosed herein, may exhibit one or more unique or distinct binding characteristics when specifically binding antigen, i.e., a binding characteristic not exhibited by typical or conventional antibodies that specifically bind the same antigen. Identification and/or isolation of such $V_L$ antigen binding proteins include methods of evaluating the binding characteristics of such antigen-specific $V_L$ antigen binding proteins to an antigen, and may also comprise comparing those binding characteristics to the binding characteristics of typical or conventional antibodies that specifically bind the same antigen. Some embodiments further comprise isolating a nucleic acid sequence encoding a $V_L$ antigen binding protein that exhibits one or more distinct binding characteristics and, optionally, expressing the nucleic acid sequence.

As a general overview, methods of profiling the binding characteristics of an antigen binding protein comprises (a) contacting an antigen-specific binding protein with the antigen (including fragments thereof and/or modified fragments thereof) under conditions that permit binding, preferably specific binding, and (b) detecting the binding protein-antigen complex formed between the antigen (or fragments thereof and/or modified fragments thereof) and the binding protein, if any. A "binding characteristic" as used herein refers to any one of the well-known measurable properties, including, but not limited to, sensitivity, specificity, avidity, affinity, etc. A skilled artisan will recognize that these general binding characteristics may be result of a combination of specific binding characteristics, e.g., epitope specificity, association constant, dissociation constant, equilibrium constant etc. A binding profile comprises any one or more of such binding characteristics.

"Specifically bind," "specific binding," "bind specifically," "antigen-specific" or the like refers to an antigen binding protein forming a complex with an antigen that is relatively stable under physiologic conditions. Specific binding is characterized by a high affinity and a low to moderate capacity as distinguished from nonspecific binding which usually has a low affinity with a moderate to high capacity. Typically, binding is considered specific when the association constant $K_A$ is higher than $10^6 M^{-1}$. If necessary, nonspecific binding can be reduced without substantially affecting specific binding by varying the binding conditions. The appropriate binding conditions, such as concentration of antigen-binding protein, ionic strength of the solution, temperature, time allowed for binding, concentration of a blocking agent (e.g., serum albumin, milk casein), etc., may be optimized by a skilled artisan using routine techniques.

Methods of profiling large numbers of antigen binding proteins directed against an antigen are well-known in the art, and include, but are not limited to, routine cross-blocking assays, epitope mapping, alanine scanning mutants, peptide blots (Reineke (2004) *Methods Mol Biol* 248:443-63), peptide cleavage analysis, epitope excision, and epitope extraction and chemical modification of antigens (Tomer (2000) *Protein Science:* 9:487-496). Generally, these methods may include the immobilization of an antigen (or a fragment, including a modified fragment, thereof) on a surface.

Generally, solid or semi-solid supports suitable for immobilizing, binding and/or linking an antigen or fragment thereof (and modifications to render solid supports suitable for immobilizing antibodies) are well known in the art Non-limiting examples of a solid support include a biosensor chip array, a bead (e.g., polystyrene beads, magnetized beads), a microwell plate, etc. Thus, for example, CdSe—CdS core-shell nanocrystals enclosed in a silica shell can be easily derivatized for coupling to an antigen or fragment thereof (Bruchez et al. (1998) *Science* 281: 2013-2016). Similarly, highly fluorescent quantum dots (zinc sulfidecapped cadmium selenide) have been covalently coupled to biomolecules for use in ultrasensitive biological detection (Warren and Nie (1998) *Science* 281: 2016-2018). Fluorescently labeled beads are commercially available from Luminex and Quantum Dot. In addition, pads, film, nanowells, or microfluid channels may also serve as a solid support.

In some embodiments, the antigen or fragment thereof (including a modified fragment thereof) may be immobilized, bound or linked on a solid or semi-solid surface such as polyvinylidene difluoride, nitrocellulose, agarose, and/or polyacrylamide gel pads. Glass slides activated with aldehyde, polylysine, or a homofunctional cross-linker may also be used. In some embodiments, the antigen(s) or fragment(s) thereof may be arranged in a three-dimensional array, for example in the three dimensional polyacrylamide gel pad microarray described in Mirzabekov et al., *Nucleic Acids Res* 24(15): 2998-3004 (1996). In a preferred embodiment, the antigen(s) or fragment(s) thereof may also be immobilized on a biosensor chip surface, a polystyrene bead or the like.

Methods and conditions for antigen binding are well known in the art and further described herein. Also well-known in the art are methods and conditions for detecting antigen-binding rotein complexes. Detection of antigen-binding protein complexes may be qualitative and/or qualitative. Binding of a multiplicity (generally, a large multiplicity) of binding proteins, e.g., in a set, may also be detected. Methods for detecting antigen-binding protein complexes include, e.g., ELISAs, fluorescent immunoassays, Western and dot blots, immunoprecipitations, competition assays using competitor polypeptides, and focal immunoassays, surface plasmon resonance (SPR) technology, multiplex detection assays, etc.

Differential Antigen Disruption

In a preferred embodiment, a profiling method as disclosed herein is based, in part, on the principal that the degree of similarities between the response patterns (e.g., binding profiles) of two binding proteins against a macromolecule after the introduction of a series of independent stable changes into the macromolecule reflects the degree of the similarity between the epitopes of the macromolecule bound by the two binding proteins. Evaluating such macromolecular interactions after changes are made in the macromolecule is a method known in the art as Modification-Assisted Profiling (MAP), Antigen Structure-based Antibody Profiling (ASAP) or Differential Antigen Disruption (DAD). DAD is a method that categorizes large numbers of antigen-binding proteins directed against the same antigen according to the similarities of the binding profile of each antigen-binding protein to chemically or enzymatically modified antigens or fragments thereof (US Patent Application Publication No. 2004/0101920, herein specifically incorporated by reference in its entirety; see also Shi et al. (2006) *J. Immunol. Methods* 314:9-20)). Each category may reflect a binding characteristic (e.g., an epitope) either distinctly different from, or partially overlapping with, a binding characteristic (e.g., an epitope) represented by another category. This technology allows rapid filtering of genetically identical antigen-binding proteins, such that characterization can be focused on genetically distinct antigen-binding proteins. DAD may be used to sort the $V_L$ antigen binding proteins of the invention into groups of antigen-binding proteins that exhibit a unique binding characteristic compared to conventional antibodies, e.g., $V_L$ antigen binding proteins that bind epitopes masked to typical antibodies.

Preferably, the antigen protein may be immobilized on either biosensor chip surfaces or polystyrene beads. Affinity-based biosensors employ biological molecules, such as antibodies, receptors, ligands, enzymes, carbohydrates, or nucleic acids, as signal transducers at the interface between solid-state electronics and solution-phase biology. The inherent recognition properties of these biomolecular interactions can be observed and measured by biosensors with a high degree of sensitivity and selectivity (for review, see Baird and Myszka (2001) *J. Molecular Recognition,* 14:261-268).

Advantages of the use of biosensors include the ability to collect data in real-time, thus rapidly providing detailed information about a binding reaction, and second, the binding reaction between interacting biomolecules does not require labeling of the biomolecules, for example, with fluorescent or radioactive labels in order for the binding reaction to be observed. The most established biosensor instruments and technology is currently provided by Biacore AB (Uppsala, Sweden). The Biacore instruments (models 1000, 2000, and 3000) are fully automated, sensor chip-based SPR devices that can accept samples directly from 96-well plates. When docked into one of these instruments, a sensor surface, called a chip, is divided into four independent flow cells that can be operated individually or in a series. This flow-cell configuration allows buffer to pass continuously over the sensor surface, thereby alleviating the need for time-consuming washing steps when exchanging analyte solution for buffer. In addition, continuous flow systems ensure that the ligand is exposed to a constant analyte concentration for the duration of the binding measurement process. Furthermore, the availability of four flow-cells on each sensor chip permits the user to immobilize three different samples and maintain a reference surface within the same sensor chip. The Biacore 2000 and 3000 models are capable of monitoring binding interactions within all four flow-cells simultaneously. The delivery of analyte to each surface in series allows in-line reference subtraction and improved data quality (Myszka (1999) *J. Mol. Recogn.* 12:279-284; Rich et al. (2000) *Curr. Opin. Biotechnol.* 11:54-71). Other biosensors such as IASYS® instruments by Affinity Sensors, SPR670 by Nippon Laser Electronics, Bio-Suplar II by Analytical µSystems, and SPREETA™ by Texas Instruments can also be used in practicing the methods of the invention.

Polystyrene beads may be processed with, for example, an assay such as a multiplex LUMINEX™ detection assay (Luminex Corp., TX). Because of the capacity of LUMINEX™ to handle multiplex analysis with up to 100 different types of beads, LUMINEX™ provides almost unlimited antigen surfaces with various modifications, resulting in improved resolution in antibody epitope profiling.

Modification or alteration of antigen structure may be effected by either chemical treatment that tends to specifically modify side chains of particular amino acid residues of the antigen protein, or by enzymatic treatment. All modifications may be preferably carried out on the antigen which is immobilized on a surface, e.g., a biosensor surface, a polystyrene bead, etc. Many different types of antigenic modifications may performed, with each surface or bead comprising antigen modified in one way. Typically an appropriate control surface to which non-modified antigen is immobilized may be included in the analysis.

Non-limiting examples of chemicals that are suitable to effect the chemical alteration or modification include succinimidyl esters and their derivatives, primary amine-containing compounds, hydrazines and carbohydrazines, free amino acids, homo- and hetero-oligopeptides containing two to twenty residues in length, Tris (2-carboxyethyl) phosphine hydrochloride (TCEP.HCl)/Iodoacetamide, N-ethyl-N'-(dimethylaminopropyl) carbodiimide (EDC)/ethanolamine, iodoacetamide and hydrazine, p-hydroxyphenylglyoxal (HPG), hydrogen peroxide, N-bromosuccinimide, N-acetylimidazole, tetranitromethane, arsanilic acid, dansyl chloride, glutaraldehyde, ninhydrin, diethylpyrocarbonate (DEPC), sulfosuccinimidyl acetate (sulfo-NHS-acetate), polyethylene glycol 5000 (PEG-5000), and 7-hydroxycoumarin-3-carboxylic acid, succinimidyl ester. Skilled artisans will recognize that still many other chemicals could be used in practicing DAD.

Non-limiting examples of enzymes, specifically proteases, that are suitable to effect the enzymatic alteration or modification of antigen include modified porcine trypsin, endoproteinase Glu-C, endoproteinase Asp-N, chymotrypsin, endoproteinase Lys-C, and endoproteinase Arg-C, pepsin, papain, thermolysin, subtilisin, protease K, bromelain, and sulfhydryl-specific protease (ficin). Once again, the skilled artisan will readily recognize that other proteases could be used in practicing the method of the invention.

Using SPR technology, binding may be measured as resonance units (RU) using experimental settings that allow for simultaneously measuring the antigen-binding protein complex on all surfaces including one non-modified and three modified surfaces of each sensor chip. Normalized responses may be calculated as percentages of binding responses from each of the three modified surfaces to the control (unmodified) sensor surface. Therefore, nine response data (%) of each sample may collected by running each sample over three separately prepared sensor chips, each containing a non-modified surface and three differently modified surfaces.

In a preferred embodiment, antigen may be immobilized to a polystyrene bead. Beads comprising non-modified and non-modified antigen generated according to methods well-known in the art. Using e.g., a multiplex detection assay, e.g., such as the LUMINEX™ detection assay, antigen-binding protein complexes may be measured as mean fluorescence intensity and normalized responses may be calculated.

Binning

In a particular and specific application, the invention provides a method for evaluating the interactions between antigen-binding proteins, e.g., $V_L$ antigen binding proteins and typical antibodies, and the antigens to which they are directed, enabling a rapid method for sorting the antigen-binding proteins into functional groups (also called clusters or bins) whose members, called siblings, exhibit a unique and similar binding characteristic or profile to an antigen, e.g., to a chemically or enzymatically modified antigen. Binding proteins that are clustered based on the similarity of their binding characteristics or profiles are considered to have a similar binding characteristic, e.g., bind the same epitope or similar epitopes. These clusters may optionally be displayed in matrix format, or in "tree" format as a dendrogram, or in a computer-readable format, or in any data-input-device-compatible format Information regarding clusters may be captured from a matrix, a dendrogram or by a computer or other computational device. Data capture may be visual, manual, automated, or any combination thereof.

As used herein, the term "bin" may be used as a noun to refer to clusters of binding proteins identified as having similar binding profiles to a panel of modified/disrupted antigen surfaces according to the methods of the present invention. The term "bin" may also be used a verb to refer to practicing the methods of the present invention, which includes any analysis of data produced by the assay.

Binning, as described herein, is the process of grouping binding proteins based on one or more binding characteristics, e.g., the epitopes they recognize. More particularly, binning comprises methods and systems for discriminating the epitope recognition properties of different binding proteins, combined with computational processes for clustering binding proteins based on their epitope recognition properties and identifying bins of binding proteins having distinct binding profiles. Accordingly, embodiments include assays for determining the epitope binding properties of binding proteins as discussed herein, and processes for analyzing data generated from such assays.

Binning may accomplished by any of the methods of: 1) grouping binding characteristics, e.g., by visual examination, treating each antigen binding exhibited as a graduated bar (e.g., as percentage of the control from each modified antigen surface); 2) calculating the determinant value of each binding protein matrix and sorting all the calculated determinants into groups (see "Calculus—One and Several Variables" 6th Edition by Salas and Einar, pp 715-717, 1990); or 3) applying pattern recognition algorithms and related bioinformatic software to the binding profile data generated by the methods and classifying the binding proteins into functional groups.

In one embodiment, the normalized response profiles for antigen-binding protein complexes may be organized into groups using appropriate statistical software. The grouping may also be achieved by calculating the determinant of each response matrix followed by sorting determinants into groups and possibly visually inspecting the gradated color bar column (profile) of each group to verify the grouping results. The entire "grouping process" may be achieved by bioinformatic pattern recognition or data mining computation software. Non-limiting examples of such software include the commercially available programs routinely used by DNA microarray analyses like J-express (DeNova, Inc. Vancouver, British Columbia), Stanford Gene Cluster Software (Stanford University, Calif.), StatSoft of Statistica, or other suitable non-commercial programs developed by skilled artisans.

Various techniques may be employed to visualize the profiles generated as described above. In order for a human observer to make meaningful comparisons, the space in which the profiles are presented should be comprehendible. Although it may be difficult to visualize meaningful trends or clusters in high dimensional spaces, one embodiment comprises two or three dimensions (binding characteristics) that are expected to be most relevant to a particular profile, although it may not be possible to view other potentially meaningful binding features on the same two or three-dimensional space.

Various techniques may be employed to address this problem. Such techniques create a lower dimensional space in which the individual dimensions capture two or more features of the data. Examples of such techniques include principle component analysis (PCA), linear and non-linear discriminant analysis, multidimensional scaling, and projection pursuit techniques. A particularly preferred approach involves the use of PCA. PCA determines the vectors (dimensions) through which a data set shows the greatest variation in multidimensional space. The first principle component shows the direction of greatest variation in the data. The second principle component shows the direction of the second greatest variation in data and so on. One can select as many principle components as are suitable to depict one's data. Typically, the first one, two, or three principle components are selected for presenting data to human observers. Principal component analysis is described more fully in Jackson, J. E. (1991) A User Guide to Principal Components. New York: John Wiley and Sons; and Jolliffe, I. T. (1986) Principal Component Analysis. New York: Springer-Verlag, both of which are incorporated herein by reference for all purposes.

Various commercially available tools for performing principle component analysis are available. Exemplary statistical computing packages for performing PCA may be available from Insightful Corporation (formerly MathSoft) of Seattle, Wash. or Partek Corporation of St. Louis, Mo., e.g., Partek Genomic Suite Software. Principal component analysis can be applied to quantitative binding profiles in a straight-forward manner. However, it will generally be necessary to normalize profile data sets before submitting them to principle component analysis. This is because the various scalars that comprise the individual features of a profile reside on vastly different scales. To bring these various features onto a comparable scale for meaningful PCA analysis, one may perform transformations to normalize the data. In one preferred embodiment, each of the dimensions is scaled by considering all the data along that dimension, subtracting the mean of that data and dividing by the standard deviation. This effectively scales the data for normalization.

In a preferred embodiment, the data generated from differential antigen disruption may be normalized in the following manner. Raw data may be normalized by dividing the binding signal of an antigen binding protein to a modified antigen surface (or bead set) by the binding signal of the same antigen binding protein to an unmodified antigen surface (or bead set). Subsequently, all values for a given surface (or bead set) may be divided by the mean value from all binding proteins to that surface (or bead set). Finally, all values may be transformed using log 2 as a base.

In another embodiment, binding profiles are generated by a high throughput competitive binding protein assay, e.g., the Multiplexed Competitive Antibody Binning (MCAB) assay, and the input data is analyzed using the Competitive Pattern Recognition (CPR) process, both of which are described in U.S. Pat. No. 8,568,992 (incorporated herein in its entirety).

Upon normalization of binding profiles, e.g., signal intensities, various well-known computational approaches may be used to identify underlying patterns in complex data. One approach that has proven valuable for the analysis of large biological data sets is hierarchical clustering. Applying this method, binding proteins may be forced into a strict hierarchy of nested subsets based on their dissimilarity values. In an illustrative embodiment, the pair of binding proteins with the lowest dissimilarity value is grouped together first. The pair or cluster(s) of binding proteins with the next smallest dissimilarity (or average dissimilarity) value is grouped together next. This process is iteratively repeated until one cluster remains. In this manner, the binding proteins are grouped according to how similar their binding profiles are, compared with the other binding proteins. In one embodiment, binding proteins are grouped into a dendrogram (sometimes called a "phylogenetic tree") whose branch lengths represent the degree of similarity between the binding patterns of the two binding proteins. Long branch lengths between two binding proteins indicate they likely bind to different epitopes. Short branch lengths indicate that two binding proteins likely compete for the same epitope.

The functional groups identified according to the methods disclosed herein may be verified using well-known methods according to the principle that binding proteins in the same functional group should share a unique or distinct binding characteristic. In one embodiment, the unique or distinct binding characteristic of binding proteins in a single bin results in the binding proteins of that bin binding or competition for the same epitope(s) of an antigen, wherein binding proteins representing different functional groups should not bind or compete for the same epitope(s) of an antigen. In this embodiment, ELISA, competition assays, epitope mapping assays, peptide arrays, etc., may all be used to verify the bins determined herein.

A bin or functional group comprises all or substantially all $V_L$ antigen binding proteins when the bin comprises at least 90%, preferably at least 95%, more preferably at least 98%, and most preferably at least 99% $V_L$ proteins. In one embodiment, a bin comprises 100% $V_L$ antigen binding proteins. In one embodiment sufficient numbers of antigen-specific $V_L$ antigen binding proteins and conventional antibodies are profiled for meaningful comparison and binning. In one embodiment, the binding proteins in or isolated from serum of non-human animals that express $V_L$ antigen binding proteins and that are immunized with an antigen are profiled and compared to the binding profiles of binding proteins in or isolated from serum of control non-human animals that are immunized with the same antigen. In one embodiment, immunization comprises priming, i.e., administering the antigen to the non-human animal for the first time, allowing the non-human animal to rest for a period of time, e.g., a few days, a week, two weeks, three weeks, four weeks, five weeks, etc., and re-administering the antigen to the non-human animal one or more times.

EXAMPLES

The following non-limiting examples are set forth so as to provide those of ordinary skill in the art with a complete disclosure and description of how to make and use non-human animals described herein and aid in the understanding thereof, and are not intended to limit the scope of what the inventors regard as their invention nor are they intended to represent that the experiments below are all or the only experiments performed. The Examples do not include detailed descriptions of conventional methods that would be well known to those of ordinary skill in the art (molecular cloning techniques, etc.). Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Generation of Non-Human Animals Having Modified Immunoglobulin Loci

This example illustrates exemplary methods of engineering immunoglobulin loci of non-human animals to contain (a) an immunoglobulin heavy chain locus comprising unrearranged human immunoglobulin light chain $V_L$ and $J_L$ gene segments operably linked to an immunoglobulin heavy chain constant region nucleic acid sequence; and (b) an immunoglobulin light chain locus comprising unrearranged human immunoglobulin light chain $V_L$ and $J_L$ gene segments operably linked to an immunoglobulin light chain constant region nucleic acid sequence.

Figure 2:
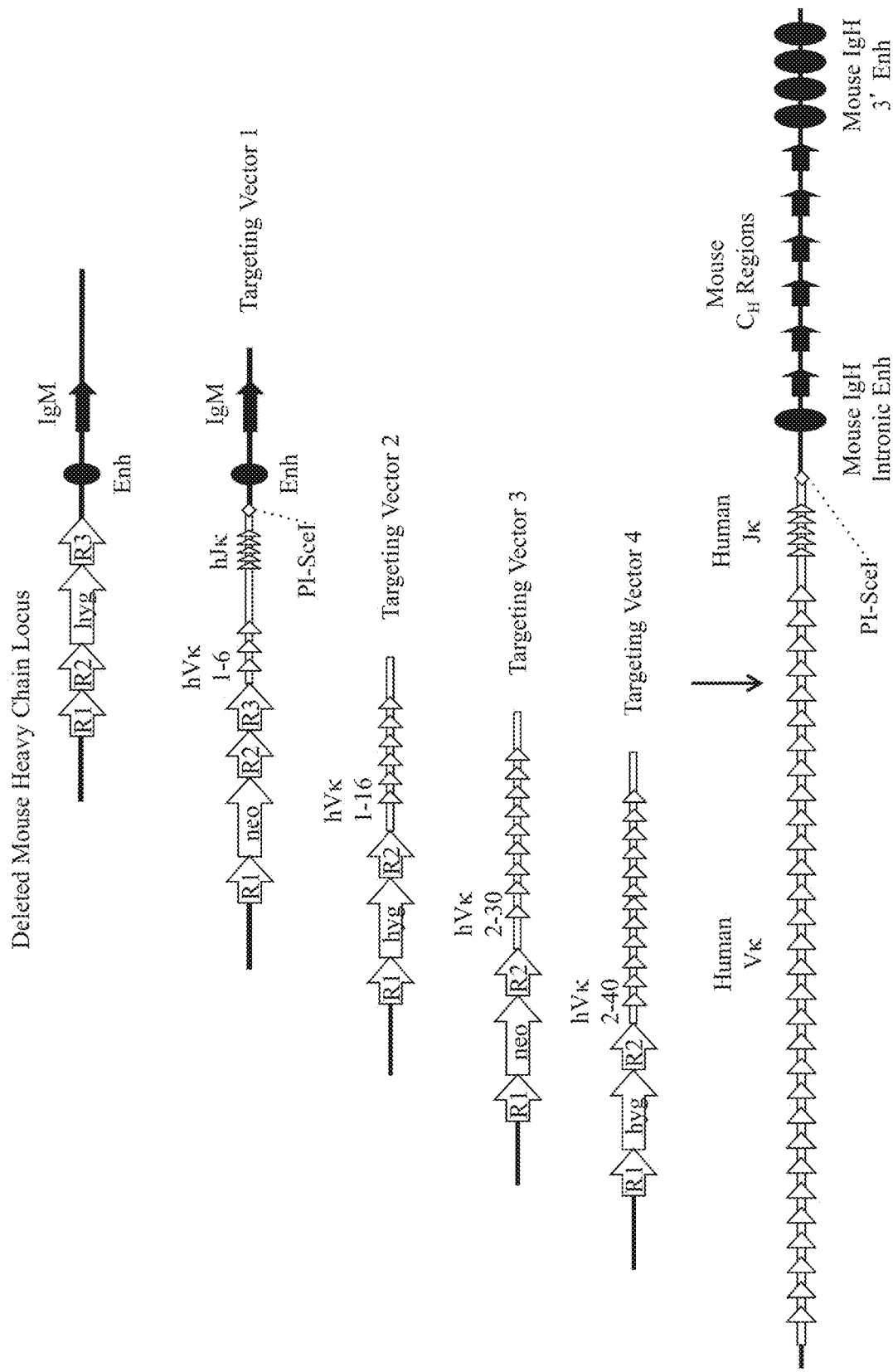
FIG. 2 shows an exemplary targeting strategy for progressive insertion of 40 human Vκ and 5 human Jκ gene segments into a mouse heavy chain locus. Hygromycin (hyg) and Neomycin (neo) selection cassettes are shown with recombinase recognition sites (R1, R2, etc.). A modified mouse heavy chain locus comprising human Vκ and Jκ gene segments operably linked to mouse $C_H$ regions is shown at the bottom.

Construction of exemplary targeting vectors for the insertion of human light chain V and J gene segments (e.g., Vκ and Jκ) into a murine immunoglobulin heavy chain locus is described below. FIG. 2 illustrates four exemplary targeting vectors that contain a plurality of human κ light chain gene segments for insertion into a murine immunoglobulin heavy chain locus using homologous recombination.

Various targeting constructs were made using VELOCIGENE® genetic engineering technology (see, e.g., U.S. Pat. No. 6,586,251 and Valenzuela, D. M., Murphy, A. J., Frendewey, D., Gale, N. W., Economides, A. N., Auerbach, W., Poueymirou, W. T., Adams, N. C., Rojas, J., Yasenchak, J., Chernomorsky, R., Boucher, M., Elsasser, A. L., Esau, L., Zheng, J., Griffiths, J. A., Wang, X., Su, H., Xue, Y., Dominguez, M. G., Noguera, I., Torres, R., Macdonald, L. E., Stewart, A. F., DeChiara, T. M., Yancopoulos, G. D. (2003). High-throughput engineering of the mouse genome coupled with high-resolution expression analysis. Nat Biotechnol 21, 652-659) to modify mouse genomic Bacterial Artificial Chromosome (BAC) libraries. Mouse BAC DNA may be modified by homologous recombination to delete the endogenous $V_H$, $D_H$ and $J_H$ gene segments for the subsequent insertion of unrearranged human $V_L$ and $J_L$ gene segments. Alternatively, the endogenous $V_H$, $D_H$ and $J_H$ gene segments may be left intact and inactivated so that recombination of endogenous gene segments to form a functional variable region is inhibited (e.g., by inversion or disruption of gene segments).

Genetically modified mice, and methods of making the same, whose genome contains an immunoglobulin heavy chain locus comprising unrearranged human immunoglobulin light chain $V_L$ and $J_L$ gene segments operably linked to an immunoglobulin heavy chain constant region nucleic acid sequence are described in U.S. Patent Application Publication No. 2012-0096572 A1, incorporated herein by reference in its entirety. As shown in FIG. 2, four targeting vectors were engineered to progressively insert 40 human Vκ gene segments and five human Jκ gene segments into an inactivated mouse heavy chain locus (e.g., deleted endogenous $V_H$, $D_H$ and $J_H$ gene segments) using standard molecular techniques recognized in the art. Table 3 sets forth the size of human DNA included in each targeting vector, which contains various human κ light chain gene segments for insertion into a mouse immunoglobulin heavy chain locus. Any number of human Vκ and Jκ gene segments may be included in the targeting vectors. The exemplary targeting vectors set forth in FIG. 2 include human κ light chain gene segments that are naturally found in the proximal contig of the germ line human κ light chain locus (FIG. 1). The resulting endogenous heavy chain locus after successive insertion of all four targeting vectors is shown in the bottom of FIG. 2.

TABLE 3

| Targeting Vector | Size of Human κ Sequence | Human κ Gene Segments Added Vκ | Jκ |
|---|---|---|---|
| 1 | ~110.5 kb | 4-1, 5-2, 7-3, 2-4, 1-5, 1-6 3-7, 1-8, 1-9, 2-10, 3-11, | 1-5 |
| 2 | ~140 kb | 1-12, 1-13, 2-14, 3-15, 1-16 1-17, 2-18, 2-19, 3-20, 6-21, | — |
| 3 | ~161 kb | 1-22, 1-23, 2-24, 3-25, 2-26, 1-27, 2-28, 2-29, 2-30 | — |

TABLE 3-continued

| Targeting Vector | Size of Human κ Sequence | Human κ Gene Segments Added Vκ | Jκ |
|---|---|---|---|
| 4 | ~90 kb | 3-31, 1-32, 1-33, 3-34, 1-35, 2-36, 1-37, 2-38, 1-39, 2-40 | — |

Using a similar approach, other combinations of human light chain variable domains in the context of murine heavy chain constant regions may be constructed. Additional light chain variable domains may be derived from human Vλ and Jλ gene segments. Exemplary targeting vectors that include human DNA that include various numbers of human Vλ and Jλ gene segments are set forth in FIG. 3.

Figure 3:
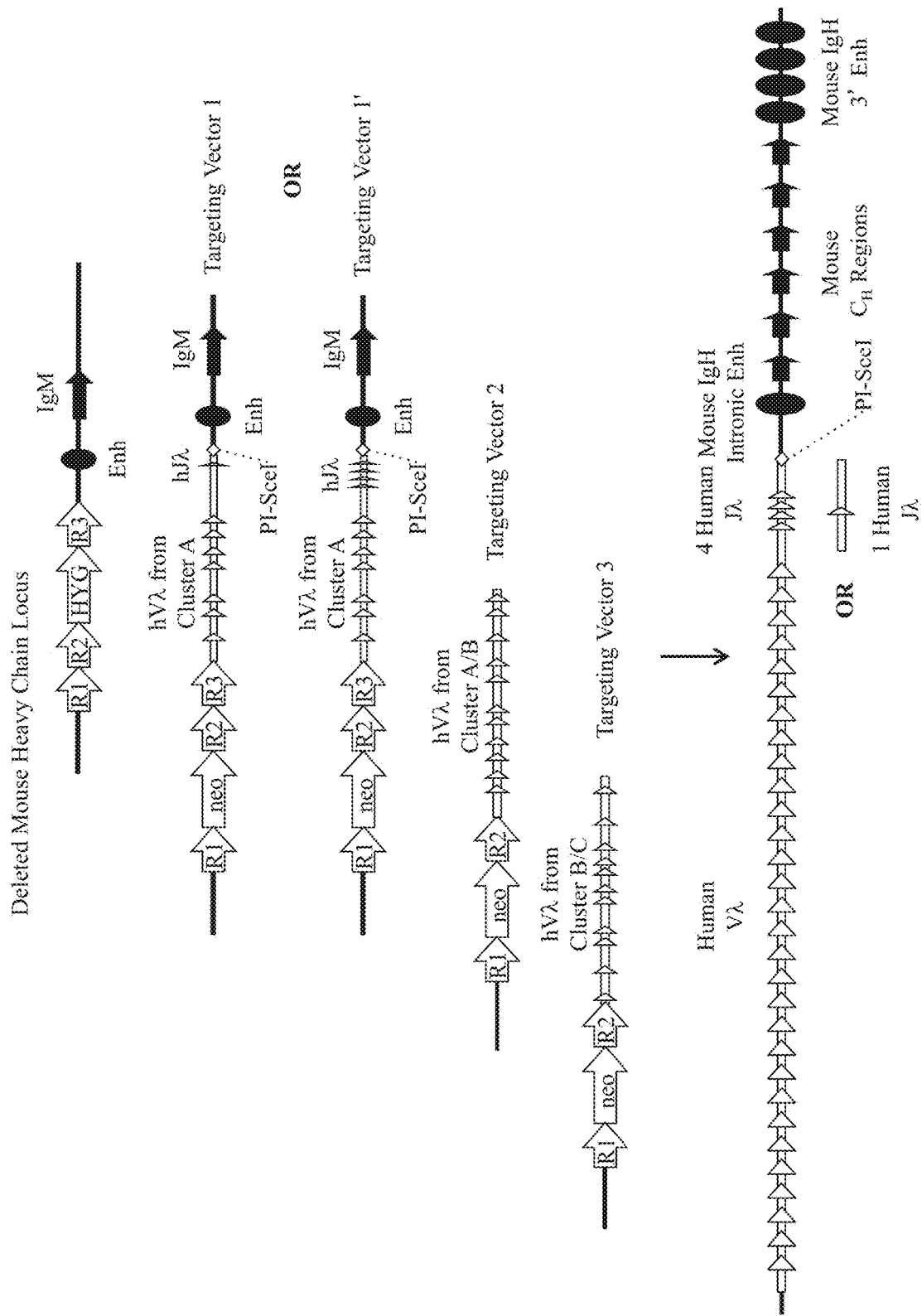
FIG. 3 shows an exemplary targeting strategy for progressive insertion of human Vλ and a human Jλ gene segment (or four human Jλ gene segments) into the mouse heavy chain locus. Hygromycin (hyg) and Neomycin (neo) selection cassettes are shown with recombinase recognition sites (R1, R2, etc.). A modified mouse heavy chain locus comprising human Vλ and Jλ gene segments (one or four) operably linked to mouse $C_H$ regions is shown at the bottom.

The human λ light chain locus extends over 1,000 kb and contains over 80 genes that encode variable (V) or joining (J) segments. Among the 70 Vλ gene segments of the human λ light chain locus, anywhere from 30-38 appear to be functional gene segments according to published reports. The 70 Vλ sequences are arranged in three clusters, all of which contain different members of distinct V gene family groups (clusters A, B and C). Within the human λ light chain locus, over half of all observed Vλ domains are encoded by the gene segments 1-40, 1-44, 2-8, 2-14, and 3-21. There are seven Jλ gene segments, only four of which are regarded as generally functional JX gene segments Jλ1, Jλ2, Jλ3, and Jλ7. In some alleles, a fifth Jλ-Cλ gene segment pair is reportedly a pseudo gene (CX6). Incorporation of multiple human Jλ gene segments into a hybrid heavy chain locus, as described herein, may be constructed by de novo synthesis. In this way, a genomic fragment containing multiple human Jλ gene segments in germline configuration is engineered with multiple human Vλ gene segments and allow for normal V-J recombination in the context of a heavy chain constant region. An exemplary targeting vector that includes multiple Jλ gene segments is shown in FIG. 3 (Targeting Vector 1').

Coupling light chain variable domains with heavy chain constant regions represents a potentially rich source of diversity for generating unique $V_L$ antigen binding proteins with human $V_L$ regions in non-human animals. Exploiting this diversity of the human λ light chain locus (or human κ locus as described above) in mice results in the engineering of unique hybrid heavy chains and gives rise to another dimension of binding proteins to the immune repertoire of genetically modified animals and their subsequent use as a next generation platform for the generation of therapeutics.

The targeting vectors described above are used to electroporate mouse embryonic stem (ES) cells to created modified ES cells for generating chimeric mice that express $V_L$ antigen binding proteins (i.e., human light chain gene segments operably linked to mouse heavy chain constant regions). ES cells containing an insertion of unrearranged human light chain gene segments are identified by the quantitative PCR assay, TAQMAN® (Lie and Petropoulos, 1998. Curr. Opin. Biotechnology 9:43-48). Specific primers sets and probes are design for insertion of human sequences and associated selection cassettes, loss of mouse heavy chain sequences and retention of mouse sequences flanking the endogenous heavy chain locus.

ES cells bearing the human light chain gene segments (e.g., Vκ and Jκ) can be transfected with a construct that expresses a recombinase in order to remove any undesired selection cassette introduced by the insertion of the human light chain gene segments. Optionally, the selection cassette may be removed by breeding to mice that express the recombinase (e.g., U.S. Pat. No. 6,774,279, which is incorporated by reference herein in its entirety). Optionally, the selection cassette is retained in the mice.

Targeted ES cells described above are used as donor ES cells and introduced into an 8-cell stage mouse embryo by the VELOCIMOUSE® method (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007). F0 generation mice fully derived from gene-targeted embryonic stem cells allowing immediate phenotypic analyses. Nat Biotechnol 25, 91-99). VELOCIMICE® (F0 mice fully derived from the donor ES cell) independently bearing human light chain gene segments at a mouse immunoglobulin heavy chain locus are identified by genotyping using a modification of allele assay (Valenzuela et al., supra) that detects the presence of the unique human light chain gene segments at an endogenous immunoglobulin heavy chain locus. Pups are genotyped and a pup heterozygous or homozygous for the genetically modified immunoglobulin heavy chain locus is selected for characterizing expression of $V_L$-containing heavy chains.

The introduction of human κ light chain gene segments into a mouse heavy chain locus was carried out in an F1 ES line (F1H4; Valenzuela et al. 2007, supra) derived from 12956/SvEvTac and C57BL/6NTac heterozygous embryos that further contained an in situ replacement of the mouse κ light chain gene segments with human κ light chain gene segments (e.g., see U.S. Pat. Nos. 6,596,541 and 8,642,835, incorporated herein by reference in their entireties).

Mice comprising genetically engineered heavy chain loci containing unrearranged human immunoglobulin light chain $V_L$ and $J_L$ gene segments in a heavy chain locus (KOH mice: MAID1713: 40 human Vκ gene segments and five human Jκ gene segments; MAID1994: 40 human Vκ gene segments and five human Jκ gene segments, and an integrated Adam6 gene) were generated as described above. Briefly, in KOH mice, all endogenous functional heavy chain variable gene segments were deleted and replaced with 40 unrearranged human Vκ gene segments and five (5) unrearranged human Jκ gene segments, which are operably linked to an immunoglobulin heavy chain constant region nucleic acid sequence.

Homozygous VELOCIMMUNE® humanized mice (VI3; see U.S. Pat. Nos. 8,642,835 and 8,502,018 B2, incorporated herein by reference in their entireties) were bred to homozygous KOH mice (MAID1713 or MAID 1994) mice to produce a mouse heterozygous for the modified light chain allele and the KOH allele. F1 heterozygous mice generated from this cross were bred to each other to obtain mice homozygous for each allele (MAID1713HO 1242HO, MAID1994HO 1242HO). Such mice express $V_L$ antigen binding proteins that have a structure that resembles that of immunoglobulins, but yet are distinct in that such binding proteins lack heavy chain variable domains. The presence of the genetically modified alleles in the immunoglobulin heavy chain and light chain loci was confirmed by TAQ-MAN™ screening and karyotyping using specific probes and primers described above. The homozygous KOH mice comprise an insertion of unrearranged human light chain gene segments as described herein (e.g., human Vκ and Jκ) into the mouse heavy chain locus in which all endogenous variable heavy chain V, D, and J gene segments have been deleted and an insertion of unrearranged human light chain gene segments (e.g., human Vκ and Jκ) into the mouse kappa (κ) light chain locus in which all mouse Vκ and Jκ genes have been deleted. In some embodiments, KOH mice further comprise an integrated Adam6 gene.

Mice whose genome comprises (i) an immunoglobulin heavy chain allele that contains an insertion of forty (40) unrearranged human Vκ and five (5) κ gene segments so that said human Vκ and Jκ gene segments are operably linked to endogenous heavy chain constant regions, and (ii) an immunoglobulin light chain allele that contains an insertion of forty (40) unrearranged human Vκ and five (5) Jκ gene segments so that said human Vκ and Jκ gene segments are operably linked to an endogenous light chain constant region are referred to as MAID1713/1242, "KOH mice" (see U.S. Patent Application Publication no. 2012-0096572 A1, incorporated herein by reference in its entirety). Mice having the same and also an integrated mouse Adam6 gene are referred to as MAID1994/1242 (see U.S. Patent Application Publication no. 2013-0212719 A1, herein incorporated by reference in its entirety).

Example 2

Generation and Characterization of $V_L$ Antigen Binding Proteins

The present example describes the production of antigen-binding proteins from mice specifically engineered to express immunoglobulin-like molecules that comprise immunoglobulin light chain variable domains and are devoid of heavy chain variable domains (as described above). This present Example specifically illustrates the generation of exemplary antigen-binding proteins specific for small molecules (e.g., a steroid and a natural product alkaloid), which contain (i) two polypeptides that each comprise an immunoglobulin light chain variable domain linked to an immunoglobulin light chain constant domain, and (ii) two polypeptides that each comprise an immunoglobulin light chain variable domain linked to an immunoglobulin heavy chain constant domain.

$V_L$ antigen binding proteins are obtained from genetically modified mice whose genome includes immunoglobulin heavy and light chain loci that each contain unrearranged human light chain gene segments (e.g., $V_L$ and $J_L$ gene segments) operably linked to endogenous heavy and light chain constant regions, respectively. Such mice provide a robust in vivo system for making antigen-binding proteins to non-proteinaceous targets as compared to wild-type and/or control genetically modified mice.

Immunization

Generally, a mouse as described herein is challenged with an antigen, and cells (such as B-cells) are recovered from the animal (e.g., from spleen or lymph nodes). The cells may be fused with a myeloma cell line to prepare immortal hybridoma cell lines, and such hybridoma cell lines are screened and selected to identify hybridoma cell lines that produce antibodies containing hybrid heavy chains specific to the antigen used for immunization. DNA encoding the human Vκ regions of the hybrid heavy chains and light chains may be isolated and linked to desirable constant regions, e.g., heavy chain and/or light chain. Due to the presence of human Vκ gene segments fused to mouse heavy chain constant regions, a unique antibody-like repertoire is produced and the diversity of the immunoglobulin repertoire is dramatically increased as a result of the unique antibody-like format created. This confers an added level of diversity to the antigen specific repertoire upon immunization. The resulting cloned sequences may be subsequently produced in a cell, such as a CHO cell. Alternatively, DNA encoding the antigen-specific $V_L$ antigen binding proteins or the variable domains may be isolated directly from antigen-specific lymphocytes (e.g., B cells; see U.S. Pat. No. 7,582,298 B2, which is incorporated by reference in its entirety).

Initially, high affinity $V_L$ antigen binding proteins are isolated having human Vκ regions and mouse constant regions. As described above, the $V_L$ antigen binding proteins are characterized and selected for desirable characteristics, including affinity, selectivity, epitope, etc. The mouse constant regions may be replaced with a desired human constant region to generate unique fully human $V_L$ antigen binding proteins containing somatically mutated human Vκ domains from an unrearranged hybrid heavy chain locus of the invention. Suitable human constant regions include, for example wild type or modified IgG1 or IgG4 or, alternatively Cκ or Cλ.

Separate cohorts of KOH mice were separately immunized with a natural product alkaloid (Antigen A) and a steroid (Antigen B). Separate cohorts of "VI3" (VELOCIMMUNE® humanized mice, see U.S. Pat. Nos. 8,642,835 and 8,502,018 B2) and "ULC" mice (see US 2011-0195454A1, US 2012-0021409A1, US 2012-0192300A1, US 2013-0045492A1, US 2013-0185821A1 and US 2013-0302836A1; which applications are herein incorporated by reference in their entireties) were also immunized to provide comparable immune response profiles.

Briefly, Antigen A was conjugated to KLH and used as immunogen to immunize KOH, VI3 and ULC mice. For Antigen B, a BSA conjugate was used as immunogen to immunize KOH and VI3 strains. Pre-immune serum was collected from the mice prior to the initiation of immunization. The immunogen was administered at 2.35 µg of conjugate for the initial priming immunization mixed with 10 µg of CpG oligonucleotide (Invivogen) as an adjuvant in a volume of 25 µl via footpad (f.p.) injection. Subsequently, mice were boosted via the same route with 2.35 µg of respective immunogens along with 10 µg of CpG and 25 µg of Adju-Phos (Brenntag) as adjuvants on days 3, 6, 11, 13, 17, 20 for a total of 6 boosts. The mice were bled on days 15 and 22 after the 4th and 6th boost, respectively. The anti-serum was assayed for titers to KLH conjugates of Antigen A. For Antigen B, titers were assayed on BSA conjugated Antigen B and BSA. For KOH mice, after completion of 6 boosts, mice were allowed a resting phase of 4 to 5 weeks, following which 4 additional boosts with the immunogens were administered. Mice were bled and anti-serum titers assayed.

When a desired immune response is achieved splenocytes are harvested and fused with mouse myeloma cells to preserve their viability and form hybridoma cell lines. The hybridoma cell lines are screened and selected to identify cell lines that produce antigen-specific $V_L$ antigen binding proteins. Using this technique several antigen-specific $V_L$ antigen binding proteins (i.e., binding proteins possessing human Vκ domains in the context of mouse heavy and light chain constant domains) are obtained.

Alternatively, antigen-specific $V_L$ antigen binding proteins are isolated directly from antigen-positive B cells without fusion to myeloma cells, as described in U.S. Pat. No. 7,582,298, herein specifically incorporated by reference in its entirety. Using this method, several fully human antigen-specific $V_L$ antigen binding proteins (i.e., antibodies possessing human Vκ domains and human constant domains) were obtained.

Anti-Serum Titer Determination

Serum titers against an immunogen were determined by a standard ELISA. The following describes the assay in detail. Ninety six-well microtiter plates (Thermo Scientific) were coated at 2 µg/ml with either BSA conjugates of either Antigen A (a substituted aromatic natural product alkaloid) or Antigen B (a steroid) in phosphate-buffered saline (PBS, Irvine Scientific) overnight at 4° C. The next day, plates were washed with phosphate-buffered saline containing 0.05% Tween 20 (PBS-T, Sigma-Aldrich) four times using a plate washer (Molecular Devices). Plates were then blocked with 250 µl of 0.5% bovine serum albumin (BSA, Sigma-Aldrich) in PBS and incubated for 1 h at room temperature. The plates were then washed four times with PBS-T. Sera from immunized mice and pre-immune sera were serially diluted three-fold in 0.5% BSA-PBS starting at 1:300 or 1:1000, added to the blocked plates in duplicate, and then incubated for 1 hr at room temperature. The last two wells were left blank to be used as a secondary antibody control (background control). The plates were again washed four times with PBS-T in a plate washer. Goat anti-mouse IgG-Fc-Horse Radish Peroxidase (HRP) conjugated secondary antibody (Jackson Immunoresearch) was then added to the plates at 1:5000/1:10,000 dilution and incubated for 1 hr at room temperature. Plates were then washed eight times with PBS-T and developed using TMB/$H_2O_2$ as substrate. The substrate was incubated for 20 min and the reaction stopped with 2 N sulfuric acid ($H_2SO_4$, VWR, cat # BDH3500-1) or 1 N phosphoric acid (JT Baker, Cat #7664-38-2). Plates were read on a spectrophotometer (Victor, Perkin Elmer) at 450 nm. Titers were computed using Graphpad PRISM software.

The immune response induced in mice to the injected immunogen was measured as titers, which is defined as the reciprocal of the highest serum dilution at which antigen binding absorbance is two-fold higher over background. At the end of immunization course both KOH and the VI3 mice elicited comparable high titers.

Identification of Binding Proteins by Luminex

To prepare antigen-coupled beads for screening, 0.12 mL of Luminex bead suspension (carboxylated microspheres, Luminex Corp.) in 0.1M sodium phosphate buffer (J. T. Baker Cat No. 4011-01) at pH 6.2 was activated by addition of 15 µl of 50 mg/mL EDC (1-Ethyl-3-(3-dimethylamino-propyl)carbodiimide, Sigma Cat No. 03449) and 15 µl of 50 mg/mL Sulfo-NHS (N-hydroxysuccinimide,Pierce Cat No. 24510) followed by incubation at room temperature for 10 minutes. Subsequently, 0.5 mL of 20 µg/mL BSA-conjugated Antigen A (a substituted aromatic natural product alkaloid) in 50 mM MES buffer at pH 5 (ACROS Cat No. 327765000) was added to the activated beads, and the primary amine coupling reaction was allowed to proceed for two hours, and the remaining reactive groups on the beads were quenched by addition of 1/10 volume of 1M Tris solution at pH 8 (Teknova Cat. No. T1080). Beads were washed with PBS (Life Technologies Cat. No. 14190-144) containing 0.05% Tween-20 (Calbiochem Cat No. 655205), and stored in PBS buffer containing 2% w/v BSA (Sigma Cat No. A4503). In the same manner, a batch of negative control beads with BSA protein coupled was also prepared.

To screen the binding proteins, 75 µl aliquots containing 3000 Anitgen A-BSA beads were distributed to each pre-hydrated well of 96-well filter plates (Millipore Cat. No. MSBVN1250). Each binding protein sample (25 µl) was added to each well and the plates were incubated overnight on a plate shaker at 4° C. On the morning of the second day, beads were washed with PBS buffer containing 0.05%

Tween-20 (PBS-T) using a vacuum manifold, and bead-bound binding protein was detected by incubation of the beads with 0.1 mL of 1.25 µg/mL R-Phycoerythrin-conjugated Goat anti-human Igκ antibody (Southern Biotech Cat. No. 2063-09) in PBS-T for 30 minutes at room temperature. Beads were then washed and suspended in 0.15 mL of PBS-T, and the median fluorescence intensity (MFI) was measured with a Luminex flow cytometry-based analyzer. In a similar manner, BSA-conjugated Antigen B (a steroid) beads were prepared and binding protein-containing samples were screened.

Relative Binding Kinetics 50 nM of Neutravidin was pre-incubated with 200 nM of biotin labeled antigen for at least 24 hours before the start of screening. Tagging of Neutravidin to the small molecule enhanced the sensitivity of the throughput affinity screening of binding protein crude supernatants by increasing the small molecule mass weight Biacore sensor surface, which was first immobilized with anti-human Fc or anti-mouse Fc specific antibody, was used to capture of antibodies from crude conditioned media. The small molecule/Neutravidin solutions were then injected over the binding protein captured surface for two minutes followed by dissociation of the bound complex for 10 minutes. The experiment was performed at 25° C. using HBST as running buffer.

Figure 4:
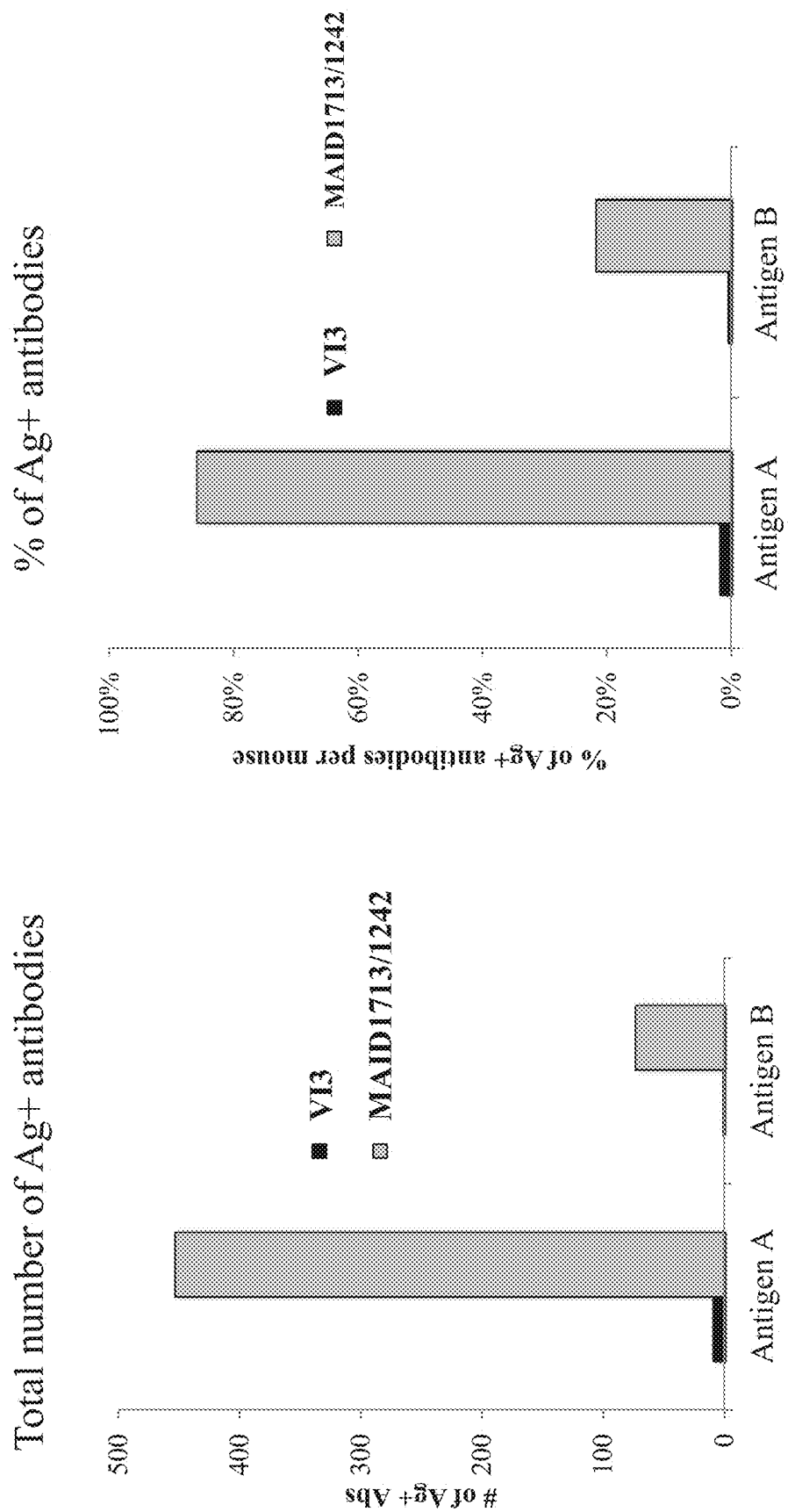
FIG. 4 shows the total number (left) and percentage (right) of antigen-positive antibodies (or $V_L$ antigen binding proteins) obtained from KOH mice (MAID 1713/1242) and VELOCIMMUNE® humanized mice (VI3).
Figure 5:
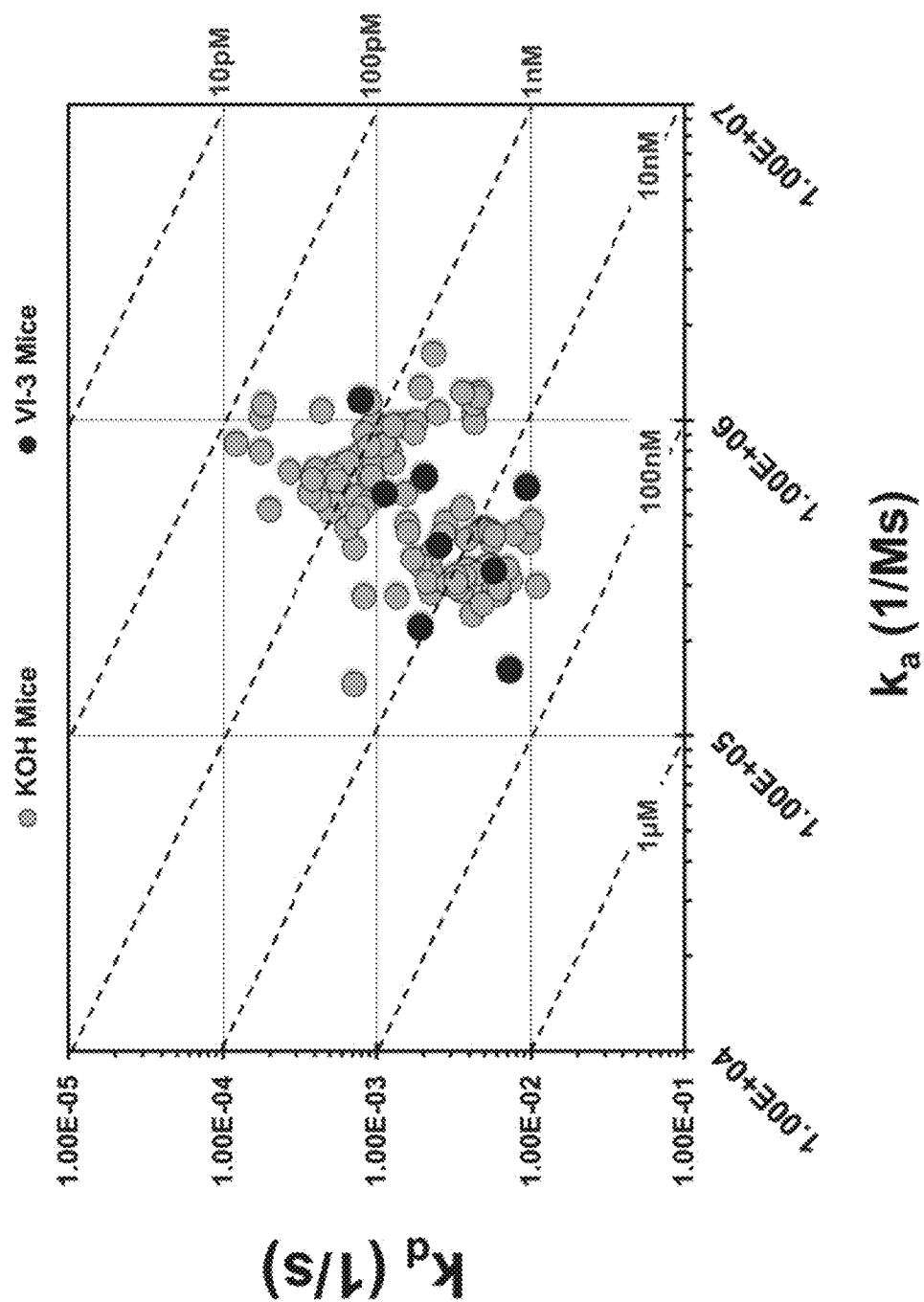
FIG. 5 shows the relative binding kinetics of antibodies specific for Antigen B obtained from KOH mice (MAID 113/1242) and VELOCIMMUNE® humanized mice (VI3).

FIG. 4 sets forth the total number (left) and percentage (right) of antigen-positive antibodies (i.e., $V_L$ antigen binding proteins) obtained from KOH mice and VELOCIMMUNE® humanized mice. FIG. 5 sets forth exemplary binding kinetics of antibodies against Antigen B obtained from KOH mice and VELOCIMMUNE® humanized mice.

The results showed that VELOCIMMUNE® humanized mice (VI3) produced 10 of 528 binding protein samples having an MFI>1000 on the Antigen A beads. For the Antigen B beads, VELOCIMMUNE® humanized mice (VI3) showed only two of 350 binding protein samples having an MFI above 1000. In contrast, KOH mice showed 453 of 528 samples having an MFI>1000 on the Antigen A beads. On the Antigen B beads, KOH mice showed 74 of 339 samples having an MFI>1000. All antigen positive samples showed minimum or negligible binding on the negative control BSA beads (e.g., MFI~118).

Human κ Gene Segment Usage

To further characterize the anti-Antigen A or anti-Antigen B $V_L$ antigen binding proteins produced in the mice according to the invention, nucleic acids encoding the human Vκ domains (from both the heavy and light chains of the $V_L$ antigen binding protein) were cloned and sequenced using methods adapted from those described in US 2007/0280945A1, incorporated herein in its entirety by reference. From the nucleic acid sequences and predicted amino acid sequences of the antibodies, gene usage was identified for the hybrid heavy chain variable region of selected and purified $V_L$ antigen binding proteins obtained from the mice immunized with Antigen A or B (described above). Table 4 sets forth the usage of human Vκ and Jκ gene segments from selected anti-Antigen A $V_L$ antigen binding proteins. Table 5 sets forth the usage of Vκ and Jκ gene segments from selected anti-Antigen B $V_L$ antigen binding proteins.

The gene usage data show that mice according to the invention can generate unique hybrid heavy chain variable regions against a small antigen, which are derived from a variety of human Vκ and Jκ gene segments in the immunoglobulin heavy chain locus. Human Vκ and Jκ gene segment usage further demonstrates diverse and varied rearrangement within its locus as well as in comparison to light chain Vκ and Jκ gene segments. Further, the diversity is apparent in the gene segment usage between hybrid heavy chain and light chain.

TABLE 4

| | Hybrid Heavy Chain | | Light Chain | |
|---|---|---|---|---|
| $V_L$ Protein | Vκ | Jκ | Vκ | Jκ |
| 1 | 3-20 | 4 | 4-1 | 2 |
| 2 | 3-20 | 4 | 1-5 | 2 |
| 3 | 4-1 | 1 | 4-1 | 3 |
| 4 | 4-1 | 1 | 3-20 | 3 |
| 5 | 1-5 | 5 | 3-20 | 1 |
| 6 | 3-20 | 4 | 1-5 | 2 |
| 7 | 4-1 | 1 | 3-20 | 2 |
| 8 | 3-20 | 4 | 1-5 | 2 |
| 9 | 4-1 | 1 | 3-20 | 3 |
| 10 | 4-1 | 1 | 3-20 | 3 |
| 11 | 1-33 | 1 | 1-33 | 3 |
| 12 | 4-1 | 1 | 3-20 | 3 |
| 13 | 4-1 | 1 | 3-20 | 3 |
| 14 | 4-1 | 1 | 3-20 | 2 |
| 15 | 3-20 | 3 | 4-1 | 1 |
| 16 | 1-33 | 1 | 3-20 | 3 |
| 17 | 3-20 | 3 | 4-1 | 1 |
| 18 | 4-1 | 1 | 3-20 | 1 |
| 19 | 4-1 | 1 | 3-20 | 3 |
| 20 | 4-1 | 1 | 3-20 | 3 |
| 21 | 4-1 | 1 | 3-20 | 3 |
| 22 | 4-1 | 1 | 3-20 | 3 |
| 23 | 1-33 | 3 | 3-20 | 5 |

TABLE 5

| | Hybrid Heavy Chain | | Light Chain | |
|---|---|---|---|---|
| $V_L$ Protein | Vκ | Jκ | Vκ | Jκ |
| 24 | 1-5 | 3 | 3-20 | 3 |
| 25 | 3-15 | 5 | 1-39 | 3 |
| 26 | 1-5 | 4 | 3-20 | 2 |
| 27 | 1-5 | 4 | 3-20 | 3 |
| 28 | 1-5 | 5 | 3-20 | 2 |
| 29 | 1-5 | 3 | 3-20 | 2 |
| 30 | 4-1 | 3 | 3-20 | 2 |
| 31 | 4-1 | 1 | 3-20 | 2 |
| 32 | 1-5 | 4 | 3-20 | 1 |
| 33 | 1-5 | 5 | 3-20 | 1 |
| 34 | 4-1 | 1 | 3-20 | 2 |

Affinity Determination

Equilibrium dissociation constants ($K_D$) for selected Antigen B-specific and purified $V_L$ antigen binding protein supernatants were determined by SPR (Surface Plasmon Resonance) using a BIACORE™ 2000 instrument (GE Healthcare). All data were obtained using DPBS+0.1% DMSO as the sample and running buffer at 25° C.

Briefly, each purified $V_L$ antigen binding protein was on a CM5 sensor chip surface previously derivatized with a high density of protein A using standard amine coupling chemistry. During the capture step, purified anti-Antigen B $V_L$ antigen binding protein was injected across the protein A surface at a flow rate of 5 µL/min, for a total of 3-4 minutes. The capture step was followed by an injection of either running buffer or analyte at a three-fold dilution concentration range of 270 µM-13.7 nM stock solution for 1.5 minutes at a flow rate of 100 µL/min. Dissociation of antigen from the captured purified $V_L$ antigen binding protein was monitored for least 5 minutes. The captured purified $V_L$ antigen binding protein was removed by a brief injection of 10 mM glycine, pH 1.5. All sensorgrams were double referenced by subtracting sensorgrams from buffer injections from the analyte sensorgrams, thereby removing artifacts caused by dissociation of the purified $V_L$ antigen binding protein from the capture surface. Binding data for each purified $V_L$ antigen binding protein was fit to a 1:1 binding model with mass transport using Biacore T100 Evaluation software v2.1. Table 6 provides the binding data for a commercially available antibody specific for Antigen B, eleven purified antigen B-specific $V_L$ antigen binding proteins, and 3 control antibodies obtained from control VI3 animals.

TABLE 6

| $V_L$ Protein /mAb | ka | kd | KD | $t^{1/2}$ (seconds) |
|---|---|---|---|---|
| Commercial mAb | 1.03E+06 | 5.85E−02 | 56.9 nM | 12 |
| $V_L$ Protein 1 | 4.82E+06 | 4.58E−02 | 9.49 nM | 15 |
| $V_L$ Protein 2 | 6.40E+05 | 7.43E−03 | 11.6 nM | 93 |
| $V_L$ Protein 3 | IC | IC | IC | IC |
| $V_L$ Protein 4 | 1.35E+06 | 5.98E−03 | 4.4 nM | 116 |
| $V_L$ Protein 5 | 1.19E+06 | 7.11E−03 | 6.0 nM | 97 |
| $V_L$ Protein 6 | 8.50E+05 | 7.41E−03 | 8.7 nM | 94 |
| $V_L$ Protein 7 | NB | NB | NB | NB |
| $V_L$ Protein 8 | 1.01E+06 | 4.46E−03 | 4.4 nM | 156 |
| $V_L$ Protein 9 | 1.04E+05 | 2.02E−01 | 1.93 uM | 3 |
| $V_L$ Protein 10 | 2.42E+06 | 8.10E−02 | 33.4 nM | 9 |
| $V_L$ Protein 11 | | | ≥270 uM | |
| Control mAb 1 | NB | NB | NB | NB |
| Control mAb 2 | | | ≥270 uM | |
| Control mAb 3 | Steady State | | 6.3 uM | |

IC = inconclusive 1:1 binding fit analysis due to low signal

NB=not bound

The binding affinities of 11 purified anti-antigen B $V_L$ antigen binding protein varied, all exhibiting a KD in the range of about 4.4 nM to 1.93 µM. Notably, seven of the eleven $V_L$ antigen binding proteins exhibited a $K_D$ of about 10 nM or less. In contrast, the commercially available antibody had a binding affinity to antigen A of ~57 nM, and none of the three antibodies isolated from control animals exhibited a $K_D$ in the nanomolar range. $T^{1/2}$ measurements for the purified $V_L$ antigen binding proteins exhibiting a $K_D$ in the low nanomolar range varied between 15 and 156 seconds. Without wishing to be bound by any particular theory, the fluctuations in the binding profiles of the purified $V_L$ antigen binding proteins shown in Table 6, and particularly the low affinities or lack of binding by some of the purified $V_L$ antigen binding proteins, may be a result of one or more $V_L$ antigen binding proteins recognizing an epitope of Antigen A that is present only when it is linked to the carrier. Regardless, the affinity data using purified antibody is consistent with the $V_L$ antigen binding proteins resulting from the combinatorial association of rearranged human light chain variable domains linked to heavy and light chain constant regions (described in Table 4) being high-affinity, clonally selected, somatically mutated, capable of binding small molecules with high efficiency, and thus, and therapeutically relevant.

Example 3

Profiling Binding Characteristics

Immunization

Cohorts of KOH mice were separately immunized with a human secreted glycoprotein (Antigen C) purchased from R&D systems. Separate cohorts of "Adam6/VI3" (VE-LOCIMMUNE® humanized mice, see U.S. Pat. Nos. 8,642, 835 and 8,502,018 B2 having an integrated Adam6 gene), "ULC" mice (see US 2011-0195454A1, US 2012-0021409A1, US 2012-0192300A1, US 2013-0045492A1, US 2013-0185821A1 and US 2013-0302836A1; which applications are herein incorporated by reference in their entireties), and wildtype Balb/c mice were also immunized to provide comparable immune response profiles.

Antigen C conjugated to hapten was used as an immunogen to immunize KOH, Adam6/VI3, ULC and Balb/c mice. Pre-immune serum was collected from the mice prior to the initiation of immunization. The immunogen was administered at 2.35 µg of conjugate for the initial priming immunization mixed with 10 µg of CpG oligonucleotide (Invivogen) as an adjuvant in a volume of 25 µl via footpad (f.p.) injection. Subsequently, mice were boosted via the same route with 2.35 µg of immunogen along with 10 µg of CpG and 25 µg of Adju-Phos (Brenntag) as adjuvants on days 3, 6, 11, 13, 17, 20 for a total of 6 boosts. The mice were bled on days 15 and 22 after the 4th and 6th boost, respectively. The anti-serum was assayed for antibody titers to hapten conjugates of Antigen C. For KOH mice, after completion of 6 boosts, mice were allowed a resting phase of 4 to 5 weeks, following which 4 additional boosts with the immunogens were administered. Mice were bled and anti-serum titers assayed.

Preparation and Modification of Antigen C on Beads

To prepare antigen-coupled beads for screening, 0.12 mL of Luminex bead suspension (carboxylated microspheres, Luminex Corp.) in 0.1M sodium phosphate buffer (J. T. Baker Cat No. 4011-01) at pH 6.2 was activated by addition of 15 µl of 50 mg/mL EDC (1-Ethyl-3-(3-dimethylamino-propyl)carbodiimide, Sigma Cat No. 03449) and 15 µl of 50 mg/mL Sulfo-NHS (N-hydroxysuccinimide,Pierce Cat No. 24510) followed by incubation at room temperature for 10 minutes. Subsequently, 0.5 mL of 20 µg/mL Antigen C in 50 mM MES buffer at pH 5 (ACROS Cat No. 327765000) was added to the activated beads, and the primary amine coupling reaction was allowed to proceed for two hours, and the remaining reactive groups on the beads were quenched by addition of 1/10 volume of 1M Tris solution at pH 8 (Teknova Cat No. T1080). Beads were washed with PBS (Life Technologies Cat No. 14190-144) containing 0.05% Tween-20 (Calbiochem Cat No. 655205), and stored in PBS buffer containing 2% w/v BSA (Sigma Cat No. A4503). In the same manner, a batch of negative control beads with was also prepared.

Nineteen bead sets coupled with Antigen C were individually treated with one of the following differential antigen disruption reagents: trypsin, Glu-C, Asp-N, chymotrypsin, Lys-C, Arg C, Pepsin, Sulfo-NHS acetate, EDC/Ethanolamine, TCEP/Iodoacetamide, PEG-5000, papain, thermolysin, subtilisin, proteaseK, bromelain, ficin, and H1193 or 7-hydroxycoumarin-3-carboxylic acid, succinimidyl ester. Chemical treatment comprised incubating the bead set in 10 mM freshly dissolved reactive chemicals in phosphate buffered solution (PBS) for 90 minutes at room temperature. Proteolytic treatment comprised incubating the bead set in 10-100 mg of enzyme freshly dissolved in PBS or other recommended buffer for 90 minutes at room temperature. One additional bead set was incubated in PBS for 90 minutes at room temperature and Antigen C coupled to this bead set remained unmodified. After the above incubations, the bead sets were washed in PBS containing 0.05% Tween 20 (PBS-T) and stored in PBS with 5% BSA and 0.02% sodium azide.

To screen the binding proteins, the 19 modified antigen beads and the non-modified control antigen beads, as described above, were pooled. Seventy-five (75) µl aliquots containing 3000 beads were distributed to each pre-hydrated well of 96-well filter plates (Millipore Cat No. MSBVN1250). Each antibody sample (25 µl) was added to each well and the plates were incubated overnight on a plate shaker at 4° C. On the morning of the second day, beads were washed with PBS-T using a vacuum manifold, and bead-bound antibody was detected by incubation of the beads with 0.2 mL of 1.25 µg/mL R-Phycoerythrin-conjugated Goat anti-mouse or human IgG antibody in PBS-T for 45 minutes at room temperature. Beads were then washed and suspended in 0.2 mL of PBS-T, and the median fluorescence intensity (MFI) was measured with a Luminex fluorospectrophotometer. The binding data were subjected to bioinformatic data analyses as described above.

Figure 6:
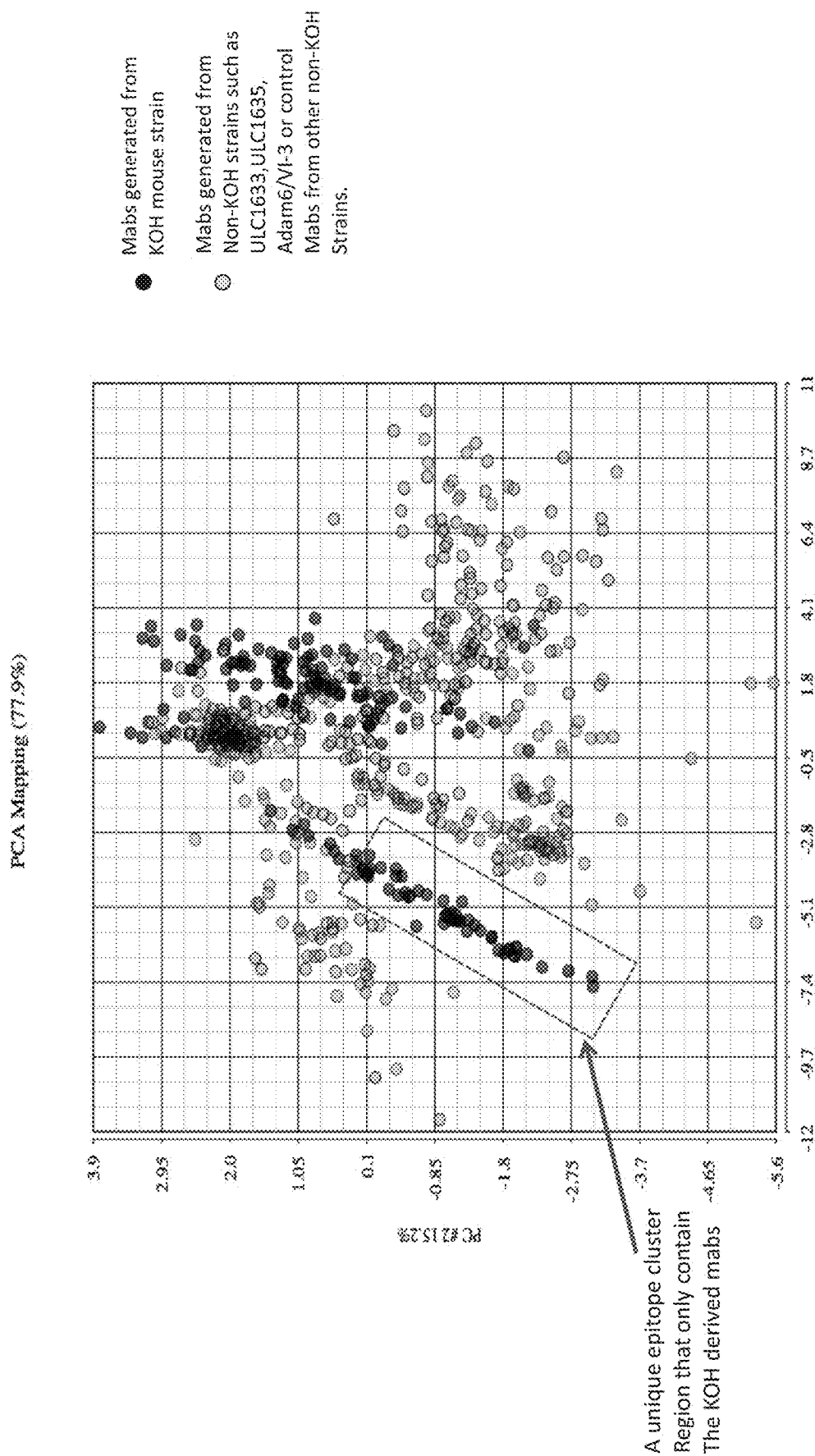
FIG. 6 provides a two-dimensional Principal Component Analysis (PCA) plot of 739 binding proteins specific for Antigen C, a glycoprotein, that highlights a cluster of Antigen C-specific $V_L$ antigen binding proteins (●) that exhibit at least one binding characteristic distinct from typical Antigen A-specific antibodies (○) as determined by Differential Antigen Disruption (DAD).

FIG. 6 provides a 2D PCA display of 736 Antigen C binding protein clusters based on the differential antigen disruption epitope profiling data. Highlighted by the rectangle is a unique epitope cluster that does not share epitope binding features with the conventional antibodies tested. Members of this unique epitope bin are $V_L$ antigen binding proteins generated in mice comprising a immunoglobulin locus encoding a hybrid immunoglobulin chain having a variable region encoded by one or more light chain variable region gene segments operably fused to a heavy chain region encoded by one or more heavy chain constant region genes.

Preparation of Modified Antigen C on Biosensor Surfaces

Antigen C, a secreted glycoprotein, is coupled to a CMS biosensor chip surface by a standard NHS/EDC-mediated amine coupling procedure. The amount of Antigen C coupled to each flow-cell surface is between 3000 to 10,000 RU. To minimize a crowding effect, the preferred coupling density is around 5000 RU. Care is taken to couple nearly identical amounts of Antigen C to all four flow-cells so fair comparisons can be made between binding to the three modified flow-cell signals and the non-modified control flow-cell surface.

Six sequencing-grade proteolytic enzymes are used to modify each coupled Antigen C surface: Trypsin, endoproteinase Glu-C and endoproteinase Asp-N to modify flow cell 2, 3, and 4 from a first biosensor chip and chymotrypsin, endoproteinase Lys-C and endoproteinase Arg-C to modify flow cell 2, 3, and 4 from a second biosensor chip. The Biacore 2000 is set to the single flow cell mode at a flow rate of 2 μl/min and 60 μl of 200 μg/ml Trypsin in 0.1M Tris-HCl, pH 8.0 is injected into flow-cell 2. A downward curving sensorgram may be observed as a typical proteolytic digestion profile, indicating that trypsin is specifically removing trypsin-digestible mass. The same dose of enzyme is repetitively injected into the flow-cell until a stable surface is formed. When trypsin digestion is complete on flow-cell 2, 60 μl of 50 μg/ml endoproteinase Glu-C in the same buffer as trypsin is injected into flow-cell 3. Again, the same dose of enzyme is repetitively injected into the same flow-cell until a stable surface is formed. In a similar manner, 60 μl of 50 μg/mlendoproteinase Asp-N in the same buffer is injected into flow-cell 4 to create a stable endo-Asp-N modified surface. At the end of the enzyme treatments, the Biacore 2000 is set to all flow-cell mode. A regeneration buffer is run across all the four Antigen C surfaces to generate stable final working surfaces.

Binding proteins specific for Antigen C generated in non-human animals having modified immunoglobulin loci and control animals as described in Example 2, as well as pre-characterized commercially available antibodies specific for Antigen C, are transferred into a new 96-well microtiter plate and mixed with 75 μl of 2× dilution buffer (20 mM Hepes, pH 7.4, 300 mM NaCl, 0.01% P-20, 40 mg/ml CMDX). Appropriate control medium mixed with 2× dilution buffer is used as a negative control.

Each binding protein sample is injected into all four flow-cells and binding signals (RU) from each flow-cell are recorded at the end of the injection and the surfaces are regenerated. The binding/regeneration cycle for each antibody sample is controlled by the Automation Wizard Program provided by the Biacore manufacturer.

Flow cells 2, 3, and 4 from a second chip containing an identical amount of Antigen C is digested with chymotrypsin, endoproteinase Lys-C, and endoproteinase Arg-C, respectively, in a similar manner as described supra in the preparation of the first chip. The same set of binding protein samples is injected into all four flow-cells and their binding signals (RU) are collected in the same manner as the first chip.

Identical amounts of Antigen C are coupled to all four flow-cells of a third CMS chip by a standard aldehyde coupling protocol (BIA Applications Handbook, 4.5). The amount of Antigen C coupled to each flow-cell surface is between 3000 to 10,000 RU, with the preferred coupling amount at around 5000 RU to minimize any crowding effect. To modify any E amine of lysine in Antigen C without denaturing its structure, 5 mM sulfo-NHS-acetate dissolved in phosphate buffered saline (PBS) is injected at 5 μl/min into flow-cell 2 for 20 minutes. To modify any carboxylic acid groups of any glutamic acid and aspartic acid residues in Antigen C without denaturing its structure, 200 mM EDC dissolved in $H_2O$ is injected into flow-cell 3 at the same flow rate for 7 minutes followed by an injection of 50 mM hydrazine dissolved in $H_2O$ for 7 minutes. For denaturing treatment of Antigen C, 100 mM TCEP dissolved in 0.1M Tris-HCl, pH 8.0 is injected into flow-cell 4 at the same flow rate for 20 minutes followed by injection of 100 mM iodoacetamide dissolved in 0.1M Tris-HCl, pH 8.0. At the end of the treatments, the Biacore 2000 is set to all flow-cell mode. A regeneration buffer is injected into all four Antigen C surfaces three times to generate a stable final working surfaces.

When the binding data of the three separate chips which contain the nine modified Antigen C surfaces and three unmodified Antigen C control surfaces are collected, all of the nine response RU values of each binding protein to the nine modified Antigen C surfaces are converted into response ratios to that of the unmodified controls. The response data of all the tested binding protein preparations are subjected to bioinformatic data analyses as described above.

The results of the epitope cluster distributions are shown by typical pattern recognition (non supervised) display methods. One of such display methods is hierarchical trees (Dendrograms) which outline the cluster relationships of the binding proteins in a tree-like arrangement. In the hierarchical tree, binding proteins that likely share epitopes will be linked together by relatively shorter "arms", where those that unlikely share epitopes will be linked by relatively longer "arms".

Verification of Binding Protein Clusters by Epitope Mapping

Binding proteins from two different functional groups (or clusters or bins) as determined by DAD can be verified by other methods such as ELISA, competition assay, etc. An epitope mapping assay is typically performed by Biacore or Octet instruments. Antibodies from two different functional groups should not interact with the same epitope. Therefore, the binding of a first antibody from one cluster to the immobilized antigen should not preclude binding of a second antibody from a different cluster to any significant extent Conversely, antibodies from the same cluster should exhibit near complete competition with each other when binding to their antigen.

Functional groups identified using DAD are also verified using an Antigen C primary sequence-derived peptide array. Peptides derived from Antigen C or overlapping peptides to cover the entire Antigen C sequence are prepared as dot arrays on a PVDF membrane or printed on typical protein microarray slides. Binding proteins representing different functional groups or binding proteins from the same functional group are incubated with the peptide arrays followed by a standard dot blotting or protein array binding and staining procedures. Binding proteins from the same functional group, which recognize the same epitope, should display identical or nearly identical binding patterns on the peptide array sheets or slides. Conversely, binding proteins from different functional groups, which recognize a different epitope on Antigen C, should display a different binding pattern to the peptide array.

Example 4

Figure 7:
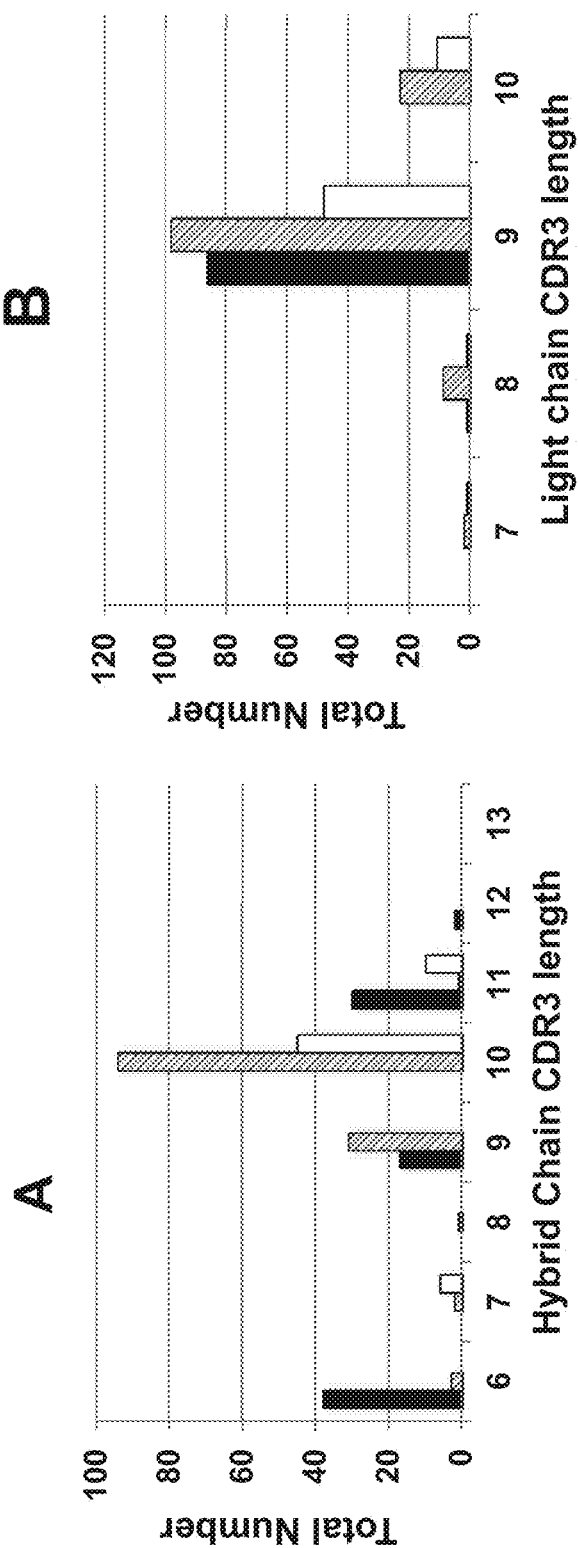
FIG. 7 provides the number of $V_L$ binding pro stated reference value. In certain embodiments, the term "approximately" or "about" includes a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Evaluation of $V_L$ Binding Proteins Specific for Small Molecules $V_L$ binding proteins generated against Antigen A, Antigen B, and Antigen C as disclosed in Examples 1-3 were evaluated for structural characteristics. In particular, the CDR3 length of hybrid and light chains of $V_L$ binding proteins specific for Antigen A (an alkaloid small molecule; n=132), Antigen B (a steroidal small molecule; n=87), or Antigen C (a glycoprotein macromolecule, n=61) was determined. Table 7 shows the number of hybrid chains having a CDR3 amino acid length of 6, 7, 8, 9, 10, 11 or 12 from $V_L$ binding proteins specific for Antigen A, Antigen B, or Antigen C. Table 8 shows the number of light chains having a CDR3 amino acid length of 7, 8, 9 or 10 from these same $V_L$ binding proteins. FIG. 7 provides this data in bar graph format

TABLE 7

| CDR3 Length | Antigen A | Antigen B | Antigen C | Total |
| --- | --- | --- | --- | --- |
| 6 | 3 | 38 | | 41 |
| 7 | 2 | | 6 | 8 |
| 8 | 1 | | | 1 |
| 9 | 31 | 17 | | 48 |
| 10 | 94 | | 45 | 139 |
| 11 | 1 | 30 | 10 | 41 |
| 12 | | 2 | | 2 |

TABLE 8

| CDR3 Length | Antigen A | Antigen B | Antigen C | Total |
| --- | --- | --- | --- | --- |
| 7 | 2 | | 1 | 3 |
| 8 | 9 | 1 | 1 | 11 |
| 9 | 98 | 86 | 48 | 232 |
| 10 | 23 | | 11 | 34 |

The length of the CDR3 in light chains of $V_L$ binding proteins was consistently about 9 amino acids regardless of the antigen specificity. In contrast, the length of the CDR3 in hybrid chains of the evaluated $V_L$ binding proteins was more variable, particularly for $V_L$ binding proteins specific to small molecules. The hybrid chains of $V_L$ binding proteins specific for Antigen C, a glycoprotein, had CDR3 lengths of about 10 to 11 amino acids in length, with a few having less than 10 amino acids. In contrast, the CDR3 of hybrid chains from $V_L$ binding proteins specific to small molecules, e.g., Antigen A or Antigen B, are likely to be less than 10 amino acids in length. Just under half (about 40%) of the $V_L$ binding proteins specific to Antigen B had a CDR3 length of 6 amino acids.

Taken together, these examples demonstrate that non-human animals, e.g., rodents and mice in particular, genetically modified to produce the $V_L$ antigen binding proteins as described herein, provide a robust in vivo system for the efficient generation of antigen-specific $V_L$ antigen binding proteins that exhibit binding characteristics not exhibited by typical antibodies, e.g., an ability to binding small molecules with a high affinity, possibly through the use of a novel paratope or binding surface on the small molecule not well-suited for binding by conventional antibodies.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

The invention claimed is:

1. A method of producing a $V_L$ antigen-binding protein that specifically binds a steroid comprising the steps of:
   (a) immunizing a genetically modified mouse with the steroid or the steroid linked to a carrier, wherein the genetically modified mouse comprises
      (i) a first nucleotide sequence comprising
         (A) at least an unrearranged human immunoglobulin light chain variable kappa (Vκ) 4-1 gene segment, an unrearranged human Vκ1-5 gene segment, and/or an unrearranged human Vκ3-15 gene segment, and
         (B) all five unrearranged human light chain joining kappa (Jκ1, Jκ2, Jκ3, Jκ4, and Jκ5) gene segments, and
         operably linked to a mouse immunoglobulin heavy chain constant region nucleic acid sequence, and
      (ii) a second nucleotide sequence comprising
         (A) at least an unrearranged human immunoglobulin light chain Vκ3-20 gene segment and/or an unrearranged human Vκ1-39 gene segment, and
         (B) all five unrearranged human Jκ1, Jκ2, Jκ3, Jκ4, and Jκ5 gene segments, and
         operably linked to a mouse immunoglobulin light chain constant region nucleic acid sequence; and (b) isolating a Vκ antigen-binding protein, or a cell expressing the Vκ antigen-binding protein, from the immunized mouse, wherein the Vκ antigen-binding protein comprises a first and a second immunoglobulin light chain κ variable domain, wherein the first immunoglobulin light chain κ variable domain is operably linked to an immunoglobulin heavy chain constant domain, wherein the second immunoglobulin light chain κ variable domain is operably linked to an immunoglobulin light chain constant domain, and wherein the first and the second immunoglobulin light chain κ variable domains have heterogeneous sequences and are associated to form a binding pocket of the $V_L$ antigen-binding protein that specifically binds the steroid with a $K_D$ of about 4.4 nM to 1.93 μM.

2. The method of claim 1, further comprising the steps of
(c) collecting a Vκ antigen-binding protein from supernatant of a culture of a hybridoma, wherein the hybridoma is produced from the cell isolated in step (b).

3. The method of claim 1, further comprising
(c) identifying the first and the second immunoglobulin light chain κ variable region nucleic acid sequences that encode the first and second immunoglobulin light chain κ variable domains; and
(d) expressing the nucleic acid sequences of (c) in an expression system suitable for expressing the antigen-binding protein so as to form an antigen-binding protein comprising a dimer of the first immunoglobulin light chain variable domain fused with a human $C_H$ domain and the second immunoglobulin light chain variable domain fused with a human $C_L$ domain, wherein the first immunoglobulin light chain variable domain and second immunoglobulin light chain variable domain bind the steroid.

4. The method of claim 3, wherein the expression system comprises
(i) a first nucleic acid that encodes the first immunoglobulin light chain κ variable domain fused with a human $C_H$ domain, and
(ii) a second nucleic acid that encodes the second immunoglobulin light chain κ variable domain fused with a human CL domain.

5. The method of claim 1, wherein the steroid is a hormone, an alkaloid or a cardiotonic steroid.

6. The method of claim 2, wherein the steroid is a hormone, an alkaloid or a cardiotonic steroid.

7. The method of claim 3, wherein the steroid is a hormone, an alkaloid or a cardiotonic steroid.

8. The method of claim 4, wherein the steroid is a hormone, an alkaloid or a cardiotonic steroid.

9. The method of claim 1, wherein the steroid linked to a carrier is a hapten.

10. The method of claim 2, wherein the steroid linked to a carrier is a hapten.

11. The method of claim 3, wherein the steroid linked to a carrier is a hapten.

12. The method of claim 4, wherein the steroid linked to a carrier is a hapten.

13. The method of claim 1, wherein the binding pocket of the $V_L$ antigen-binding protein specifically binds the steroid with a $K_D$ of 10 nM or less.

14. The method of claim 2, wherein the binding pocket of the $V_L$ antigen-binding protein specifically binds the steroid with a $K_D$ of 10 nM or less.

15. The method of claim 3, wherein the binding pocket of the $V_L$ antigen-binding protein specifically binds the steroid with a $K_D$ of 10 nM or less.

16. The method of claim 4, wherein the binding pocket of the $V_L$ antigen-binding protein specifically binds the steroid with a $K_D$ of 10 nM or less.

17. The method of claim 1, wherein the first nucleotide sequence comprises an unrearranged human Vκ 4-1 gene segment, an unrearranged human Vκ 5-2 gene segment, an unrearranged human Vκ 7-3 gene segment, an unrearranged human Vκ 2-4 gene segment, an unrearranged human Vκ 1-5 gene segment, an unrearranged human Vκ 1-6 gene segment, an unrearranged human Vκ 3-7 gene segment, an unrearranged human Vκ 1-8 gene segment, an unrearranged human Vκ 1-9 gene segment, an unrearranged human Vκ 2-10 gene segment, an unrearranged human Vκ 3-11 gene segment, an unrearranged human Vκ 1-12 gene segment, an unrearranged human Vκ 1-13 gene segment, an unrearranged human Vκ 2-14 gene segment, an unrearranged human Vκ 3-15 gene segment, an unrearranged human Vκ 1-16 gene segment, an unrearranged human Vκ 1-17 gene segment, an unrearranged human Vκ 2-18 gene segment, an unrearranged human Vκ 2-19 gene segment, an unrearranged human Vκ 3-20 gene segment, an unrearranged human Vκ 6-21 gene segment, an unrearranged human Vκ 1-22 gene segment, an unrearranged human Vκ 1-23 gene segment, an unrearranged human Vκ 2-24 gene segment, an unrearranged human Vκ 3-25 gene segment, an unrearranged human Vκ 2-26 gene segment, an unrearranged human Vκ 1-27 gene segment, an unrearranged human Vκ 2-28 gene segment, an unrearranged human Vκ 2-29 gene segment, an unrearranged human Vκ 2-30 gene segment, an unrearranged human Vκ 3-31 gene segment, an unrearranged human Vκ 1-32, gene segment an unrearranged human Vκ 1-33 gene segment, an unrearranged human Vκ 3-34 gene segment, an unrearranged human Vκ 1-35 gene segment, an unrearranged human Vκ 2-36 gene segment, an unrearranged human Vκ 1-37 gene segment, an unrearranged human Vκ 2-38 gene segment, an unrearranged human Vκ 1-39 gene segment, and an unrearranged human Vκ 2-40 gene segment.

18. The method of claim 2, wherein the first nucleotide sequence comprises an unrearranged human Vκ 4-1 gene segment, an unrearranged human Vκ 5-2 gene segment, an unrearranged human Vκ 7-3 gene segment, an unrearranged human Vκ 2-4 gene segment, an unrearranged human Vκ 1-5 gene segment, an unrearranged human Vκ 1-6 gene segment, an unrearranged human Vκ 3-7 gene segment, an unrearranged human Vκ 1-8 gene segment, an unrearranged human Vκ 1-9 gene segment, an unrearranged human Vκ 2-10 gene segment, an unrearranged human Vκ 3-11 gene segment, an unrearranged human Vκ 1-12 gene segment, an unrearranged human Vκ 1-13 gene segment, an unrearranged human Vκ 2-14 gene segment, an unrearranged human Vκ 3-15 gene segment, an unrearranged human Vκ 1-16 gene segment, an unrearranged human Vκ 1-17 gene segment, an unrearranged human Vκ 2-18 gene segment, an unrearranged human Vκ 2-19 gene segment, an unrearranged human Vκ 3-20 gene segment, an unrearranged human Vκ 6-21 gene segment, an unrearranged human Vκ 1-22 gene segment, an unrearranged human Vκ 1-23 gene segment, an unrearranged human Vκ 2-24 gene segment, an unrearranged human Vκ 3-25 gene segment, an unrearranged human Vκ 2-26 gene segment, an unrearranged human Vκ 1-27 gene segment, an unrearranged human Vκ 2-28 gene segment, an unrearranged human Vκ 2-29 gene segment, an unrearranged human Vκ 2-30 gene segment, an unrearranged human Vκ 3-31 gene segment, an unrearranged human Vκ 1-32, gene segment an unrearranged human Vκ 1-33 gene segment, an unrearranged human Vκ 3-34 gene segment, an unrearranged human Vκ 1-35 gene segment, an unrearranged human Vκ 2-36 gene segment, an unrearranged human Vκ 1-37 gene segment, an unrearranged human Vκ 2-38 gene segment, an unrearranged human Vκ 1-39 gene segment, and an unrearranged human Vκ 2-40 gene segment.

19. The method of claim 3, wherein the first nucleotide sequence comprises an unrearranged human Vκ 4-1 gene segment, an unrearranged human Vκ 5-2 gene segment, an unrearranged human Vκ 7-3 gene segment, an unrearranged human Vκ 2-4 gene segment, an unrearranged human Vκ 1-5 gene segment, an unrearranged human Vκ 1-6 gene segment, an unrearranged human Vκ 3-7 gene segment, an unrearranged human Vκ 1-8 gene segment, an unrearranged human Vκ 1-9 gene segment, an unrearranged human Vκ 2-10 gene segment, an unrearranged human Vκ 3-11 gene segment, an unrearranged human Vκ 1-12 gene segment, an unrearranged human Vκ 1-13 gene segment, an unrearranged human Vκ 2-14 gene segment, an unrearranged human Vκ 3-15 gene segment, an unrearranged human Vκ 1-16 gene segment, an unrearranged human Vκ 1-17 gene segment, an unrearranged human Vκ 2-18 gene segment, an unrearranged human Vκ 2-19 gene segment, an unrearranged human Vκ 3-20 gene segment, an unrearranged human Vκ 6-21 gene segment, an unrearranged human Vκ 1-22 gene segment, an unrearranged human Vκ 1-23 gene segment, an unrearranged human Vκ 2-24 gene segment, an unrearranged human Vκ 3-25 gene segment, an unrearranged human Vκ 2-26 gene segment, an unrearranged human Vκ 1-27 gene segment, an unrearranged human Vκ 2-28 gene segment, an unrearranged human Vκ 2-29 gene segment, an unrearranged human Vκ 2-30 gene segment, an unrearranged human Vκ 3-31 gene segment, an unrearranged human Vκ 1-32, gene segment an unrearranged human Vκ 1-33 gene segment, an unrearranged human Vκ 3-34 gene segment, an unrearranged human Vκ 1-35 gene segment, an unrearranged human Vκ 2-36 gene segment, an unrearranged human Vκ 1-37 gene segment, an unrearranged human Vκ 2-38 gene segment, an unrearranged human Vκ 1-39 gene segment, and an unrearranged human Vκ 2-40 gene segment.

20. The method of claim 4, wherein the first nucleotide sequence comprises an unrearranged human Vκ 4-1 gene segment, an unrearranged human Vκ 5-2 gene segment, an unrearranged human Vκ 7-3 gene segment, an unrearranged human Vκ 2-4 gene segment, an unrearranged human Vκ 1-5 gene segment, an unrearranged human Vκ 1-6 gene segment, an unrearranged human Vκ 3-7 gene segment, an unrearranged human Vκ 1-8 gene segment, an unrearranged human Vκ 1-9 gene segment, an unrearranged human Vκ 2-10 gene segment, an unrearranged human Vκ 3-11 gene segment, an unrearranged human Vκ 1-12 gene segment, an unrearranged human Vκ 1-13 gene segment, an unrearranged human Vκ 2-14 gene segment, an unrearranged human Vκ 3-15 gene segment, an unrearranged human Vκ 1-16 gene segment, an unrearranged human Vκ 1-17 gene segment, an unrearranged human Vκ 2-18 gene segment, an unrearranged human Vκ 2-19 gene segment, an unrearranged human Vκ 3-20 gene segment, an unrearranged human Vκ 6-21 gene segment, an unrearranged human Vκ 1-22 gene segment, an unrearranged human Vκ 1-23 gene segment, an unrearranged human Vκ 2-24 gene segment, an unrearranged human Vκ 3-25 gene segment, an unrearranged human Vκ 2-26 gene segment, an unrearranged human Vκ 1-27 gene segment, an unrearranged human Vκ 2-28 gene segment, an unrearranged human Vκ 2-29 gene segment, an unrearranged human Vκ 2-30 gene segment, an unrearranged human Vκ 3-31 gene segment, an unrearranged human Vκ 1-32, gene segment an unrearranged human Vκ 1-33 gene segment, an unrearranged human Vκ 3-34 gene segment, an unrearranged human Vκ 1-35 gene segment, an unrearranged human Vκ 2-36 gene segment, an unrearranged human Vκ 1-37 gene segment, an unrearranged human Vκ 2-38 gene segment, an unrearranged human Vκ 1-39 gene segment, and an unrearranged human Vκ 2-40 gene segment.

* * * * *